US009993425B2

(12) United States Patent
Costantino et al.

(10) Patent No.: US 9,993,425 B2
(45) Date of Patent: Jun. 12, 2018

(54) COMPOSITIONS FOR INTRANASAL DELIVERY OF HUMAN INSULIN AND USES THEREOF

(75) Inventors: Henry R. Costantino, Woodinville, WA (US); Annemarie Stoudt Cohen, Kirkland, WA (US); Anthony P. Sileno, Brookhaven Hamlet, NY (US)

(73) Assignee: Marina Biotech, Inc., City of Industry, CA (US)

( * ) Notice: Subject to any disclaimer, the term of this patent is extended or adjusted under 35 U.S.C. 154(b) by 0 days. days.

(21) Appl. No.: 13/314,080

(22) Filed: Dec. 7, 2011

(65) Prior Publication Data

US 2012/0094903 A1  Apr. 19, 2012

Related U.S. Application Data

(63) Continuation of application No. 12/376,205, filed as application No. PCT/US2007/067007 on Apr. 19, 2007.

(60) Provisional application No. 60/894,130, filed on Mar. 9, 2007, provisional application No. 60/868,703, filed on Dec. 5, 2006, provisional application No. 60/825,876, filed on Sep. 15, 2006, provisional application No. 60/821,515, filed on Aug. 4, 2006.

(51) Int. Cl.
*A61K 38/28* (2006.01)
*A61K 9/00* (2006.01)
*A61K 47/40* (2006.01)

(52) U.S. Cl.
CPC ............ *A61K 9/0043* (2013.01); *A61K 38/28* (2013.01); *A61K 47/40* (2013.01)

(58) Field of Classification Search
CPC ...................................................... A61K 38/28
See application file for complete search history.

(56) References Cited

U.S. PATENT DOCUMENTS

| 5,888,477 | A | 3/1999 | Gonda | |
|---|---|---|---|---|
| 7,244,709 | B2 * | 7/2007 | Quay | A61K 9/0043 424/450 |
| 2003/0211972 | A1 | 11/2003 | Backstrom | |
| 2004/0014797 | A1 * | 1/2004 | Moinet | A61K 31/425 514/369 |
| 2007/0077283 | A1 * | 4/2007 | Quay | A61K 9/0014 424/448 |

FOREIGN PATENT DOCUMENTS

| EP | 1031347 B1 | 4/2002 |
|---|---|---|
| WO | WO92/16196 A | 10/1992 |
| WO | WO94/22461 A1 | 10/1994 |

OTHER PUBLICATIONS

Heinemann, Curr Pharm Design (2001) 7:1327-51.
Jonassen, Ph arm Res (2006) 23:49-55.
Nolte, Hormone Metabol Res (1990) 22;170-74.
Oh, Meth Find Exp Clin Pharmacol (1990) 12:205-12.
Melberg, Proteins (1990) 8:280-86.
Brange, Acta Pharm Nord (1992) 3:149-58.
Home, Eur J Clin Pharmacol (1999) 55:199-203.
Aungst, J Pharmacol Exp Ther (1988) 244:23-27.
Cefalu, Diabetes Care (2004) 27:239-46.
Shao, Pharm Res (1992) 9:1157-63.
Souza, Diabetes Obesity Metabol (2001) 3:85-95.
Valensi, Pathol Biol (Apr. 1996) 235-40.
Hirai, IntJ Pharmaceutics(1981)9:165-72.
Basu, J Clin Invest (1996) 97:2351-61.
Frauman, Diabetes Res Clin Practice (1987) 3:197-202.
Lalej-Bennis, Diabetes (2001) 18:614-18.
Lovatt, Eur Biophys J (1996) 24:354-57.
Fernandez-Urrusuno, Pharm Res (1999) 16:1576-81.
Watanabe, Chem Pharm Bull (1992) 40:3100-04.
Home, Diabetes Care (1998) 21 :1904-09.
Krauland, J Pharm Sci (2006) 95:2463-72.
Dondeti, Int J Pharmaceutics (1995) 122:91-105.
Pringels, Int J Pharmaceutics (2006) Influence of deposition and spray pattern of nasal powders on insulin bioavailability, pp. 1-7.
Callens, Int J Pharmaceutics (2003) 250:415-22.
Zoete, J Molec Biol (2004) 342:913-29.
Perera, Diabetes Care (2002) 25:2276-81.
Duerloo, Pharm Res (1989) 6:853-56.
Matsuzawa, Bio Pharm Bull (1995) 18:1718-23.
Clauson, Diabetes Care (1995) 18:986-91.
Shaikh, Curr Pharm Biotechnol (2005) 6:387-95.
Brange, Adv Drug Delivery Rev (1999) 35:307-35.
Drejer, Diabetic Med (1992) 9:335-40.
Callens, J Controlled Release (2000) 66:215-20.
Lee, J Pharm Sci (1991) 80:725-29.
Reger, Drugs of Today (2006) 42:729-39.
Dotsikas, J Pharm Biomed Analysis (2002) 29:487-94.
Mitra, Int J Pharmaceutics (2000) 205:127-34.
Sluzky, Biotechnol. Bioengineer. (1992) 40:895-903.
Brange, Diabetes Care (1990) 13:923-54.
Yi Zhang, Acta Pharmacol Sin (2001) 22:1051-56.
Varshosaz, Drug Delivery (2006) 13:31-38.
Dyer, Pharm Res (2002) 19:998-1008.
Schipper, Pharm Res (1993) 10:682-86.
Gizurarsom, Chem Pharm Bull (1991) 39:2155-57.
Merkus, J Controlled Release (1996)41:69-75.
Kadima, Biopolymers (1993) 83:1643-57.
Jacobs, Diabetes (1993) 42:1649-54.
Kobayashi, J Immunology (2007) 2082-88.
Merkus et al., Cyclodextrins in nasal drug delivery, 1999, Adv. Drug Delivery Reviews, vol. 36, pp. 41-57.
Kapitza et al., Time-Action Profile of a New Pulmonary Insulin Applied with a Metered-Dose Inhaler, 2003, Diabetes, vol. 52, Suppl. 1, Abstract 449-P, pp. A105.

\* cited by examiner

*Primary Examiner* — Gyan Chandra
(74) *Attorney, Agent, or Firm* — Eckman Law Group

(57) ABSTRACT

What is described is a pharmaceutical formulation for intranasal delivery of insulin to a patient, comprising an aqueous mixture of human insulin, a solubilizing agent, a surface active agent, and a thickening agent, wherein said formulation provides a ultra-rapid acting profile to regular human insulin.

8 Claims, 7 Drawing Sheets

COMPOSITIONS FOR INTRANASAL DELIVERY OF HUMAN INSULIN AND USES THEREOF

CROSS REFERENCE TO RELATED APPLICATIONS

This application is a continuation of prior U.S. application Ser. No. 12/376,205, filed Feb. 3, 2009, which is the National Stage application under 35 U.S.C. § 371(c) of PCT International Application PCT/US2007/067007, filed Apr. 19, 2007, which claims the benefit of U.S. Provisional Application No. 60/894,130, filed Mar. 9, 2007, U.S. Provisional Application No. 60/868,703, filed Dec. 5, 2006, U.S. Provisional Application No. 60/825,876, filed Sep. 15, 2006, and U.S. Provisional Application No. 60/821,525, filed Aug. 4, 2006, each of which is hereby incorporated by reference in its entirety.

BACKGROUND

Insulin is an important glucose-regulating protein. Insulin is a naturally-occurring polypeptide hormone secreted by the pancreas. Insulin is required by the cells of the body to remove and use glucose from the blood. Glucose allows the cells to produce the energy needed to carry out cellular functions. In addition to being the primary effector in carbohydrate homeostasis, it has effects on fat metabolism. It can change the liver's ability to release fat stores. Insulin has various pharmacodynamic effects throughout the body. In healthy individuals, in response to a glucose injection, insulin is rapidly secreted reaching an initial peak within 5-7 minutes and lasting no more than 10-15 minutes (first-phase), followed by a sustained secretion lasting hours (second-phase), see FIG. 1. In Type 2 diabetes, patients experience a loss of first-phase insulin release, despite the enhancement of second-phase insulin secretion. Human data support a critical role for first-phase insulin secretion in postprandial glucose homeostasis (PPG), and evidence supports that increased incidence of cardiovascular disease is associated with PPG.

Researchers first gave an active extract of the pancreas containing insulin to a young diabetic patient in 1922, and the FDA first approved insulin in 1939. The first recombinant human insulin was approved by the FDA in 1982. Recombinant human insulin, insulin lispro, insulin aspart, and insulin glargine are the commonly-used insulins. Beef and pork insulin are infrequently used.

Insulin is used medically when treating some forms of diabetes mellitus. Patients with diabetes mellitus have an inability to take up and use glucose from the blood, and, as a result, the glucose level in the blood rises. In type 1 diabetes, the pancreas cannot produce enough insulin. Therefore, insulin therapy is needed. In type 2 diabetes, patients produce insulin, but cells throughout the body do not respond normally to the insulin. Nevertheless, administration of insulin may also be used in the treatment of type 2 diabetes in order to overcome cellular resistance to insulin. By increasing the uptake of glucose by cells and reducing the concentration of glucose in the blood, insulin prevents or reduces the long-term complications of diabetes, including, for example, damage to the blood vessels, eyes, kidneys, and nerves. Insulin is usually administered by injection under the skin (subcutaneously). The subcutaneous tissue of the abdomen is preferred because absorption of the insulin is more consistent from this location than subcutaneous tissues in other locations.

Insulin can be injected manually, or can be infused into the body with the help of a small electronic infusion device called an insulin pump. Syringes are probably the most common and cost-effective choice for insulin injection, and are useful for patients who take two types of insulin mixed together. An alternative to syringes is an insulin pen, which comes prefilled with insulin and may either be disposable or reusable (with disposable insulin cartridges). The device resembles a large pen, with a fine needle under the cap and a plunger at the other end. A dial allows the user to regulate the dose. Insulin pens are also available in the most frequently-prescribed mixtures of insulin types, such as 70/30 (NPH and regular insulin).

Another device known as an insulin jet injector works by using a high-pressure blast of air to send a fine spray of insulin through the skin. This may be a good option for those patients that are needle-shy. However, jet injectors require a significant financial investment and are not always covered by insurance.

An insulin pump may be a more effective way to control type 1 diabetes for some people because it more closely mimics the insulin production of a pancreas. An insulin pump is a compact electronic device with an attached infusion set (or tube) that administers a small, steady flow of insulin to a patient throughout the day, known as a "basal rate." Before eating, a pump user programs the pump to deliver a "bolus" of fast-acting insulin to cover the corresponding rise in blood glucose levels from the meal. Pump flow can also be manually adjusted by a user throughout the day as needed.

Disadvantages to patient administration of insulin by injection include discomfort due to multiple daily injections, reaction and infection at the injection site, variation in absorption of subcutaneous insulin, and difficulty in simulating the fast release of endogenous insulin at meal times. Thus, there is a need to develop modes of administration of insulin other than by injection.

When insulin was first discovered and made available for people with diabetes there was only one kind of short-acting insulin. This required several injections a day. As time went on, new insulins were developed that lasted longer, requiring fewer injections, but requiring strict attention to timing of meals. Presently, there are different types of insulin available. This gives more flexibility in the number and timing of administration, making it easier to maintain target blood glucose levels based on a patient's lifestyle. Insulin is available in various forms, for example, rapid-, medium-, and long-acting. Insulin is typically delivered by SC injections. However, other options such as pump delivery, and more recently pulmonary delivery are available. A dry powder formulation of a rapid acting insulin has been described for lung delivery that comprises a human crystalline zinc insulin having the amino acid sequence of natural human insulin (U.S. Pat. No. 6,737,045).

Regular human insulin (e.g., Novolin R, Humulin R) is available in vials, cartridges, and prefilled syringes. Regular human insulin is a molecule known to form molecular complexes via non-covalent interactions (i.e., dimers and hexamers).

Several insulin analogs that are prepared with recombinant DNA technology are available for clinical use. Among these agents is insulin aspart (NovoLog™; Novo Nordisk Pharmaceuticals), which is homologous with regular human insulin except for a single substitution of aspartic acid for proline at position B28. This single substitution reduces the molecule's tendency to form hexamers. Therefore, insulin aspart is absorbed more rapidly after subcutaneous injection and has both a faster onset of action and a shorter duration of action than short-acting insulins.

Insulin mixtures are also used, especially for people with type 2 diabetes. Insulin mixtures allow treatment with different types of insulins in one combined administration.

NPH human insulin (Novolin N, Humulin N) is available in vials, cartridges and prefilled syringes. A mixture of 70% NPH human insulin and 30% regular human insulin (Novolin 70/30, Humulin 70/30) is available in vials, cartridges and pre-filled syringes.

A mixture of 50% NPH human insulin and 50% regular human insulin (Humulin 50/50) is available in vials. Lente human insulin (Novolin L, Humulin L) is available in vials. Ultralente human insulin (Humulin U) is available in vials. Insulin lispro (Humalog) is available in vials and cartridges. Insulin aspart (NovoLog) is available in vials and cartridges. Insulin glargine (Lantus) is available in vials and cartridges.

Insulin is stabilized in the monomeric state to create a rapid-acting form of insulin. When the insulin is stabilized in the hexameric form the time to pharmacodynamic effect (i.e., glucose reduction) is dramatically increased, as compared to monomeric insulin, because the insulin molecules must disassociate before producing the desired biological effect. The injectable insulin treatments that are characterized as rapid acting are chemically modified to maintain the monomer, thereby imparting the rapid pharmacodynamic activity upon injection. Monomeric forms of insulin include insulin analogs and are known to be rapid acting, e.g., insulin glulisine (LysB3, GluB29), HMR-1153 (LysB3, IleB28), HMR-1423 (GlyA21, HisB31, HisB32), insulin aspart (AspB28) or (AspB10), and lispro (LysB28, ProB29). In every instance above, the nomenclature of the analogs is based on a description of the amino acid substitution at specific positions on the A or B chain of insulin, numbered from the N-terminus of the chain, in which the remainder of the sequence is that of natural human insulin.

There is a need to develop pharmaceutical formulations comprising ultra-rapid acting insulin, i.e., insulin which are able to provide peak serum levels in less than 60 minutes and glucose troughs in less than 90 minutes.

DESCRIPTION OF THIS DISCLOSURE

Figure 1:
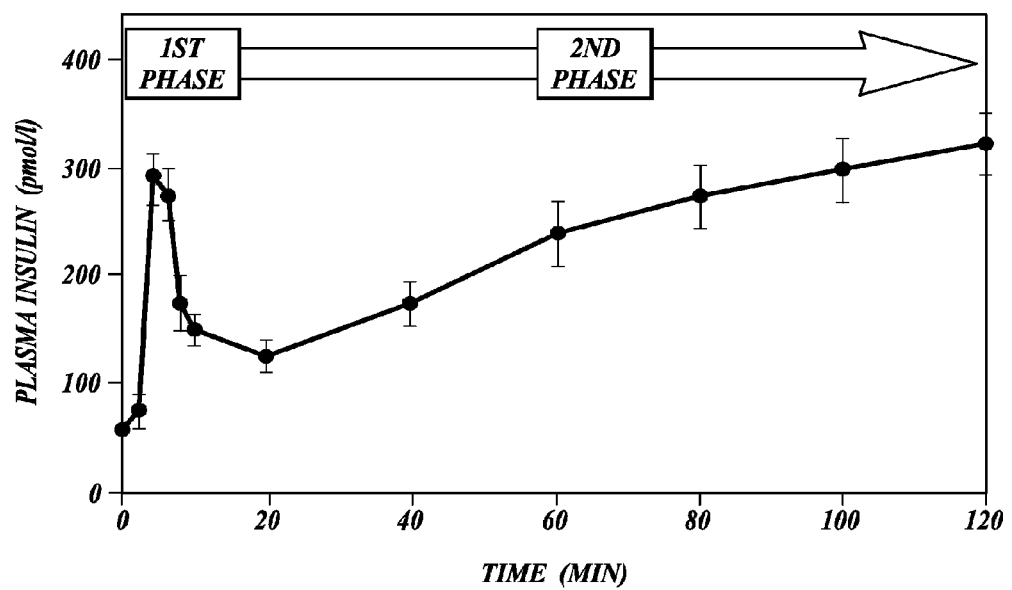
FIG. 1: Phases of insulin secretion.

In order to provide better understanding of the present disclosure, the following definitions are provided:

As used herein, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. As used herein, the terms "include" and "comprise" are used synonymously. It should be understood that the terms "a" and "an" as used herein refer to "one or more" of the enumerated components. The use of the alternative (e.g., "or") should be understood to mean either one, both or any combination thereof of the alternatives.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

"Analog" or "analogue" as used herein refers to a chemical compound that is structurally similar to a parent compound (e.g., a peptide, protein or a mucosal delivery enhancing agent), but differs slightly in composition (e.g., one atom or functional group is different, added, or removed). The analog may or may not have different chemical or physical properties than the original compound and may or may not have improved biological or chemical activity. For example, the analog may be more hydrophilic or it may have altered activity as compared to a parent compound. The analog may mimic the chemical or biological activity of the parent compound (i.e., it may have similar or identical activity), or, in some cases, may have increased or decreased activity. The analog may be a naturally or non-naturally occurring (e.g., chemically-modified, synthetic or recombinant) variant of the original compound. An example of an analog is a mutein (i.e., a protein analogue in which at least one amino acid is deleted, added, or substituted with another amino acid). Other types of analogs include isomers (enantiomers, diastereomers, and the like) and other types of chiral variants of a compound, as well as structural isomers.

"Derivative" as used herein refers to a chemically or biologically modified version of a chemical compound (including an analog) that is structurally similar to a parent compound and (actually or theoretically) derivable from that parent compound. Generally, a "derivative" differs from an "analog" in that a parent compound may be the starting material to generate a "derivative," whereas the parent compound may not necessarily be used as the starting material to generate an "analog."

As used herein, a thickening agent or thickener includes but is not limited to a viscosity enhancer, a viscosity enhancing agent, and a viscosity increasing agent. Within formulations and/or compositions of the present disclosure, a thickening agent is used to increase the viscosity of such formulation or composition.

Insulin and Insulin Homologs, Analogs and Derivatives

As used herein, insulin includes, but is not limited to, homologs, analogs, and derivatives thereof. Insulin, as used herein encompasses human insulin (e.g., natural, synthetic or recombinant), insulin glulisine (LysB3, GluB29), HMR-1153 (LysB3, IlcB28), HMR-1423 (GlyA21, HisB31, HisB32), insulin aspart (AspB28) or (AspB10), and lispro (LysB28, ProB29). Further examples of insulin according to the present disclosure may be found in Vajo and Duckworth, *Endocrine Reviews* 22(5):706-17, 2001; Vajo and Duckworth *Pharmocologic Reviews* 52(1):1-9, 2000, and Bhatnagar et al., *Progress in Biophysics and Molecular Biology* 91(3):199-228, 2006. The current disclosure focuses primarily on intranasal administration of insulins, pharmaceutical formulations, and ultra-rapid acting pharmaceutical formulations comprising insulin which are able to provide peak insulin serum levels in less than 60 minutes and glucose troughs in less than 90 minutes of administration. According to the present disclosure insulin also includes the free bases, acid addition salts or metal salts, such as potassium or sodium salts of insulin, and peptides or proteins that have been modified by such processes as amidation, glycosylation, acylation, sulfation, phosphorylation, acetylation, cyclization and other well known covalent modification methods. Thus, according to the present disclosure, the above-described peptides are incorporated into pharmaceutical formulations suitable for transmucosal delivery, especially intranasal delivery.

Mucosal Delivery Enhancing Agents

"Mucosal delivery enhancing agents" are defined as chemicals and other excipients that, when added to a formulation comprising water, salts and/or common buffers and insulin (the control formulation) produce a formulation that results in a significant increase in transport of a insulin across a mucosa as measured by the maximum blood, serum, or cerebral spinal fluid concentration ($C_{max}$) or by the area under the curve (AUC) in a plot of concentration versus time. A mucosa includes the nasal, oral, intestinal, buccal, bronchopulmonary, vaginal, and rectal mucosal surfaces and includes all mucus-secreting membranes lining all body cavities or passages that communicate with the exterior. Mucosal delivery enhancing agents are sometimes called carriers, excipients, additives, enhancing agents or enhancers (including, for example, a thickening agent).

"Endotoxin-free formulation" means a formulation comprising n insulin and one or more mucosal delivery enhancing agents that is substantially free of endotoxins and/or related pyrogenic substances. Endotoxins include toxins that are confined inside a microorganism and are released only when the microorganisms are broken down or die. Pyrogenic substances include fever-inducing, thermostable substances (glycoproteins) from the outer membrane of bacteria and other microorganisms. These substances can cause fever, hypotension and shock if administered to humans. Producing formulations that are endotoxin-free can require special equipment, expert artisans, and can be significantly more expensive than making formulations that are not endotoxin-free. Because intravenous administration of the glucose-regulating peptides, glucogon-like peptide (GLP) or amylin, simultaneously with infusion of endotoxin in rodents has been shown to prevent the hypotension and even death associated with the administration of endotoxin alone (U.S. Pat. No. 4,839,343), producing endotoxin-free formulations of insulin would not be expected to be necessary for non-parental (non-injected) administration.

Non-Infused Administration

"Non-infused administration" means any method of delivery that does not involve an injection directly into an artery or vein, a method which forces or drives (typically a fluid) into something and especially to introduce into a body part by means of a needle, syringe or other invasive method. Non-infused administration includes subcutaneous injection, intramuscular injection, intraparitoneal injection and the non-injection methods of delivery to a mucosa.

Methods and Compositions of Delivery

Improved methods and compositions for mucosal administration of insulin to mammalian subjects optimize insulin dosing schedules. The present disclosure describes mucosal delivery of insulin formulated with one or more mucosal delivery-enhancing agents wherein insulin dosage release is substantially normalized and/or sustained for an effective delivery period ranging from about 0.1 to about 2.0 hours; from about 0.4 to about 1.5 hours; from about 0.7 to about 1.5 hours; or from about 0.8 to about 1.0 hours; following mucosal administration. The sustained release of insulin achieved may be facilitated by repeated administration of exogenous insulin utilizing methods and compositions of the present disclosure.

Compositions and Methods of Sustained Release

Improved compositions and methods for mucosal administration of insulin to mammalian subjects allow for the optimization of insulin dosing schedules. The present disclosure provides improved mucosal (e.g., nasal) delivery of a formulation comprising insulin in combination with one or more mucosal delivery-enhancing agents and an optional sustained release-enhancing agent or agents. Mucosal delivery-enhancing agents of the present disclosure yield an effective increase in delivery, e.g., an increase in the maximal plasma concentration ($C_{max}$) to enhance the therapeutic activity of mucosally-administered insulin. Another factor affecting therapeutic activity of insulin in the blood plasma and CNS is residence time (RT). Sustained release-enhancing agents, in combination with intranasal delivery-enhancing agents, increase $C_{max}$ and increase residence time (RT) of insulin. An increase in residence time at the mucosal delivery site (e.g., nasal mucosa) and/or systemic circulation are contemplated herein. Polymeric delivery vehicles and other agents and methods of the present disclosure that yield sustained release-enhancing formulations, for example, polyethylene glycol (PEG), are disclosed herein. The present disclosure describes an improved insulin delivery method and dosage form for treatment of symptoms related to metabolic disease in mammalian subjects.

Within the mucosal delivery formulations and methods of this disclosure, the insulin is frequently combined or coordinately administered with a suitable carrier or vehicle for mucosal delivery. As used herein, the term "carrier" includes pharmaceutically acceptable solid or liquid filler, diluent or encapsulating material. As used herein, a carrier may be a mucosal delivery enhancing agent. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents (e.g., a thickener), tonicity agents, wetting agents or other biocompatible materials. As disclosed herein, humectants include, but are not limited to, propylene glycol, glycerine, glyceryl triacetate, a polyol, a polymeric polyol, lactic acid, and urea. Within this disclosure, pharmaceutical formulations may contain one humectant or any combination or mixture of more than one humectant. A tabulation of ingredients listed by the above categories can be found in the *U.S. Pharmacopeia National Formulary,* 1990, 1857-1859. Solubilizing agents as disclosed herein include, but are not limited to, cyclodextrin, hydroxypropyl-β-cyclodextrin, sulfobutylether-β-cyclodextrin and methyl-β-cyclodextrin. Such solubilizing agents may be used in a pharmaceutical formulation alone or in any mixture or combination of more than one solubilizing agent. Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline, acetate, glycine, histidine, arginine, glutamate, lysine, methionine, lactate, formate, and glycolate; Ringer's solution, ethyl alcohol and phosphate buffer solutions, as well as other non toxic compatible substances used in pharmaceutical formulations. Pharmaceutical formulations set forth herein may include any one buffering agent or any combination or mixture of more than one buffering agent. A buffering agent may have a $pK_a$ ranging from about 5 to about 9, or from about 6 to about 8. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), ethylene glycol tetraacetic acid, (EGTA), sorbitol, tartaric acid, phosphoric acid and the like. In accordance with the present disclosure, any one or any mixture or combination of chelating agents may be contained in a pharmaceutical formulation. The amount of active ingredient that can be combined with the carrier materials to produce a single dosage form will vary depending upon the particular mode of administration.

Within the mucosal delivery compositions and methods of this disclosure, various mucosal delivery-enhancing agents are employed which enhance delivery of insulin into or across a mucosal surface. In this regard, delivery of insulin across the mucosal epithelium can occur "transcellularly" or "paracellularly." The extent to which these pathways contribute to the overall flux and bioavailability of the insulin depends upon the environment of the mucosa, the physicochemical properties the active agent, and the properties of the mucosal epithelium. Paracellular transport involves only passive diffusion, whereas transcellular transport can occur by passive, facilitated or active processes. Generally, hydrophilic, passively transported, polar solutes diffuse across a mucosal surface through the paracellular route, while more lipophilic solutes use the transcellular route. Absorption and bioavailability (e.g., as reflected by a permeability coefficient or physiological assay), for diverse, passively and actively absorbed solutes, can be readily evaluated, in terms of both paracellular and transcellular delivery components, for any selected insulin within this disclosure. For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The paracellular route represents a relatively small fraction of accessible surface area of the nasal mucosal epithelium. In general terms, it has been reported that cell membranes occupy a mucosal surface area that is a thousand times greater than the area occupied by the paracellular spaces. Thus, the smaller accessible area, and the size- and charge-based discrimination against macromolecular permeation would suggest that the paracellular route would be a generally less favorable route than transcellular delivery for drug transport. Surprisingly, the methods and compositions of this disclosure provide for significantly enhanced transport of biotherapeutics into and across mucosal epithelia via the paracellular route. Therefore, the methods and compositions of this disclosure successfully target both paracellular and transcellular routes, alternatively or within a single method or composition.

As used herein, mucosal delivery-enhancing agents include agents which enhance or otherwise modulate the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of insulin or other biologically active compound(s). Enhancement of mucosal delivery can thus occur by any one or more of a variety of mechanisms, for example by increasing the diffusion, transport, persistence or stability of insulin, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

As used herein, a "mucosally effective amount of insulin" contemplates effective mucosal delivery of insulin to a target site for drug activity in a subject in need thereof that may involve a variety of delivery or transfer routes. For example, a given active agent may find its way through clearances (e.g., spaces) between cells of the mucosa and reach an adjacent vascular wall, while by another route the agent may, either passively or actively, be taken up (i.e., internalized) into mucosal cells to act within the cells or be discharged (e.g., released) or transported out of the cells to reach a secondary target site, such as the systemic circulation. The methods and compositions of this disclosure may promote the translocation of active agents along one or more such alternate (transcellular or paracellular) routes, or may act directly on the mucosal tissue or proximal vascular tissue to promote absorption or penetration of the active agent(s). The promotion of absorption or penetration in this context is not limited to these mechanisms.

As used herein "peak concentration ($C_{max}$) of insulin in a blood plasma", "area under concentration vs. time curve (AUC) of insulin in a blood plasma", "time to maximal plasma concentration ($t_{max}$) of insulin in a blood plasma" are pharmacokinetic parameters known to one skilled in the art. Laursen et al., *Eur. J. Endocrinology* 135:309-315, 1996. The "concentration vs. time curve" measures the concentration of insulin in a blood serum of a subject vs. time after administration of a dosage of insulin to the subject either by intranasal, intramuscular, subcutaneous, or other parenteral route of administration. "$C_{max}$" is the maximum concentration of insulin in the blood serum of a subject following a single dosage of insulin to the subject. "$t_{max}$" is the time to reach maximum concentration of insulin in a blood serum of a subject following administration of a single dosage of insulin to the subject.

As used herein, "area under concentration vs. time curve (AUC) of insulin in a blood plasma" is calculated according to the linear trapezoidal rule and with addition of the residual areas. A decrease of 23% or an increase of 30% between two dosages would be detected with a probability of 90% (type II error $\beta$=10%). The "delivery rate" or "rate of absorption" is estimated by comparison of the time ($t_{max}$) to reach the maximum concentration ($C_{max}$). Both $C_{max}$ and $t_{max}$ are analyzed using non-parametric methods. Comparisons of the pharmacokinetics of intramuscular, subcutaneous, intravenous and intranasal insulin administrations were performed by analysis of variance (ANOVA). For pair wise comparisons a Bonferroni-Holmes sequential procedure is used to evaluate significance. The dose-response relationship between the three nasal doses is estimated by regression analysis. $P<0.05$ is considered significant. Results are given as mean values+/−SEM.

While the mechanism of absorption promotion may vary with different mucosal delivery-enhancing agents of this disclosure, useful reagents in this context will not substantially adversely affect the mucosal tissue and will be selected according to the physicochemical characteristics of the particular insulin or other active or delivery-enhancing agent. In this context, delivery-enhancing agents that increase penetration or permeability of mucosal tissues will often result in some alteration of the protective permeability barrier of the mucosa. For such delivery-enhancing agents to be of value within this disclosure, it is generally desired that any significant changes in permeability of the mucosa may be reversible within a time frame appropriate to the desired duration of drug delivery. Furthermore, there should be no substantial, cumulative toxicity, nor any permanent deleterious changes induced in the barrier properties of the mucosa with long-term use.

Within certain aspects of this disclosure, absorption-promoting agents for coordinate administration or combinatorial formulation with insulin are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the insulin. In additional aspects, surfactants (e.g., polysorbates) are employed as adjunct compounds, processing agents, or formulation additives to enhance intranasal delivery of the insulin. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the insulin from the vehicle (e.g., the therapeutic or pharmaceutical formulation) into the mucosa.

Additional mucosal delivery-enhancing agents that are useful within the coordinate administration and processing methods and combinatorial formulations include, but are not limited to, mixed micelles; enamines; nitric oxide donors (e.g., S-nitroso-N-acetyl-DL-penicillamine, NOR1, NOR4—which are preferably co-administered with an NO scavenger such as carboxy-PITO or doclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for mucosal delivery.

Other absorption-promoting agents are selected from a variety of carriers, bases and excipients that enhance mucosal delivery, stability, activity or trans-epithelial penetration of the insulin. These include, inter alia, cyclodextrins (e.g., cyclodextrin) and β-cyclodextrin derivatives (e.g., hydroxypropyl-β-cyclodextrin, sulfobutylether-β-cyclodextrin, methyl-β-cyclodextrin and heptakis(2,6-di-O-methyl-β-cyclodextrin)). These compounds, optionally conjugated with one or more of the active ingredients and further optionally formulated in an oleaginous base, enhance bioavailability of a glucose regulating peptide contained in the mucosal formulations of this disclosure. Yet additional absorption-enhancing agents adapted for mucosal delivery include medium-chain fatty acids, including mono- and diglycerides (e.g., sodium caprate—extracts of coconut oil, Capmul), and triglycerides (e.g., amylodextrin, Estaram 299, Miglyol 810).

The mucosal therapeutic and prophylactic compositions of the present disclosure may be supplemented with any suitable penetration-promoting agent that facilitates absorption, diffusion, or penetration of insulin across mucosal barriers. The penetration promoting agent may be any such agent that is pharmaceutically acceptable. Thus, in more detailed aspects of this disclosure compositions are provided that incorporate one or more of the penetration-promoting agents selected from sodium salicylate and salicylic acid derivatives (acetyl salicylate, choline salicylate, salicylamide, etc.); amino acids and salts thereof (e.g., monoaminocarboxlic acids such as glycine, alanine, phenylalanine, proline, hydroxyproline, etc.; hydroxyamino acids such as serine; acidic amino acids such as aspartic acid, glutamic acid, etc.; and basic amino acids such as lysine etc.—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts). Also provided as penetration-promoting agents within the methods and compositions of this disclosure are substances which are generally used as emulsifiers (e.g., sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like.

Within various aspects of this disclosure, improved nasal mucosal delivery formulations and methods are provided that allow for the delivery of an insulin and/or other therapeutic agents across a mucosal barriers (e.g., mucosal surface) between administration and one or more selected target sites. Certain formulations may be specifically adapted for a selected target cell, tissue or organ, or even a particular disease state. In other aspects of the instant disclosure, improved nasal delivery formulations and methods provide for efficient, selective endo- or transcytosis of insulin specifically routed along a defined intracellular or intercellular pathway. As appreciated herein, the insulin may be efficiently loaded at an effective concentration in a carrier or other delivery vehicle, which is then administered and maintained in a stabilized format when, for example, administered to the nasal mucosa and/or during passage through one or more intracellular compartments and/or membranes to a target site for drug action (e.g., the blood stream or a defined tissue, organ, or extracellular compartment). The insulin may be provided in a delivery vehicle or otherwise modified (e.g., in the form of a prodrug), wherein release or activation of the insulin is triggered by a physiological stimulus (e.g., pH change, lysosomal enzymes, etc.) In certain aspects, the insulin may be pharmacologically inactive until it reaches its target site for activity. The insulin and other formulation components are non-toxic (or reduce toxicity to an acceptable amount) and non-immunogenic. In this context, carriers and other formulation components are generally selected for their ability to be rapidly degraded and/or excreted under physiological conditions. At the same time, formulations are chemically and physically stable in dosage form for effective storage.

Peptide and Protein Derivatives, Analogs and Mimetics

Included within the definition of biologically active peptides and proteins for use within the context of this disclosure are natural or synthetic, therapeutically or prophylactically active, peptides (comprised of two or more covalently linked amino acids), proteins, peptide or protein fragments, peptide or protein analogs, and chemically modified derivatives or salts of active peptides or proteins. A wide variety of useful analogs, derivatives and/or mimetics of insulin are therefore contemplated for use within this disclosure and can be produced and tested for biological activity according to known methods. Often, the peptides or proteins of an insulin or other biologically active peptides or proteins for use within this disclosure are muteins that are readily obtainable by partial substitution, addition, or deletion of amino acids within a naturally occurring or native (e.g., wild-type, naturally occurring mutant, or allelic variant) peptide or protein sequence. Additionally, biologically active fragments of native or non-native peptides or proteins are included within the context of a biologically active peptide and/or protein described herein. Such mutant derivatives and fragments substantially retain the desired biological activity of the native peptide or proteins. In the case of peptides or proteins having a carbohydrate modification (native or non-native), biologically active variants identified by alterations to such carbohydrate species are also included within this disclosure.

As used herein, "derivative" refers to a chemically or biologically modified version of a chemical compound (e.g., a peptide or protein) that is structurally similar to a parent compound and is (actually or theoretically) derivable from that parent compound. Generally, a "derivative" differs from an "analogue" in that a parent compound may be the starting material to generate a "derivative," whereas the parent compound may not necessarily be used as the starting material to generate an "analogue." An analogue (or a derivative) may have different chemical or physical properties of the parent compound. For example, a derivative may be more hydrophilic or it may have altered reactivity as compared to the parent compound.

As used herein and as appreciated by one of skill in the art, the term "conservative amino acid substitution" refers to the general interchangeability of amino acid residues having similar side chains. For example, a commonly interchangeable group of amino acids having an aliphatic side chain is alanine, valine, leucine, and isoleucine; a group of amino acids having an aliphatic-hydroxyl side chain is serine and threonine; a group of amino acids having an amide-containing side chain is asparagine and glutamine; a group of amino acids having an aromatic side chain is phenylalanine, tyrosine, and tryptophan; a group of amino acids having a basic side chain is lysine, arginine, and histidine; and a group of amino acids having a sulfur-containing side chain is cysteine and methionine. Examples of conservative substitutions include the substitution of a non-polar (hydrophobic) residue such as isoleucine, valine, leucine or methionine for another. Likewise, the present disclosure contemplates the substitution of a polar (hydrophilic) residue such as between arginine and lysine, or between glutamine and asparagine, or between threonine and serine. Additionally, the substitution of a basic residue such as lysine, arginine or histidine for another or the substitution of an acidic residue such as aspartic acid or glutamic acid for another is also contemplated. Exemplary conservative amino acids substitution groups are: valine-leucine-isoleucine, phenylalanine-tyrosine, lysine-arginine, alanine-valine, and asparagine-glutamine. By aligning a peptide or protein analog optimally with a corresponding native peptide or protein, and by using appropriate assays, e.g., adhesion protein or receptor binding assays, to determine a selected biological activity, one can readily identify operable peptide and protein analogs for use within the methods and compositions of this disclosure. Operable peptide and protein analogs as set forth in this disclosure may be specifically cross-reactive (e.g., immunoreactive) with antibodies raised to the corresponding native peptide or protein.

An approach for stabilizing certain peptide and/or protein formulations of this disclosure is to increase the physical stability by using a solid, e.g., lyophilized peptide or protein formulation. Such stabilization will inhibit peptide or protein aggregation via hydrophobic interactions as well as via covalent modification(s) that may increase as a peptide or protein unfolds or is otherwise denatured. Stabilizing formulations in this context may include a polymer-based formulation, for example a biodegradable hydrogel formulation/delivery system. As noted herein, the critical role of water in protein structure, function, and stability is well known to one of skill in the relevant art. Typically, proteins are relatively stable in the solid state with bulk water removed. However, solid therapeutic protein formulations may become hydrated upon storage at elevated humidities or during delivery from a sustained release composition or device. The stability of proteins may drop with increasing hydration. Water can also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

Solid (e.g., lyophilized) protein preparations containing from about 6% to about 28% water (hydration) are the most unstable. Below this level, the mobility of bound water and the internal motion of a protein are low. Above this level, water mobility and protein motion approach those of full hydration. Increased susceptibility toward solid-phase aggregation with increasing hydration has been observed in several systems. However, at higher water content, less aggregation may be less obvious because of the dilution effect.

In accordance with these principles, an effective method for stabilizing peptides and proteins against solid-state aggregation for mucosal delivery is to control the water content in a solid formulation and maintain the water activity in the formulation at optimal levels. This level depends on the nature of the protein, but in general, proteins maintained below their "monolayer" water coverage will exhibit superior solid-state stability.

Within this disclosure, a variety of additives, diluents, bases and delivery vehicles are provided which effectively control water content and consequently improve protein stability. Such reagents and carrier materials effective as anti-aggregation agents include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of a peptide or protein can also be enhanced by various additives to aqueous solutions comprising the peptide or protein drugs. For example, additives, such as polyols (including sugars), amino acids, proteins such as collagen and gelatin, and various salts may be used.

Certain additives, in particular sugars and other polyols, also impart significant physical stability to dry (e.g., lyophilized) peptides or proteins. These additives can also be used within the context of this disclosure in order to protect a peptide or protein against aggregation not only during the lyophilization process but also during storage of the lyophilized product in the dry state. For example, sucrose and Ficoll 70 (a polymer with sucrose units) exhibit significant protection against peptide or protein aggregation during solid-phase incubation under various conditions. These additives may also enhance the stability of a solid protein embedded within polymer matrices.

Yet additional additives, for example sucrose, stabilize peptides or proteins against solid-state aggregation in humid atmospheres at elevated temperatures, as may occur in certain sustained-release formulations of this disclosure. Proteins such as gelatin and collagen also serve as stabilizing or bulking agents to reduce denaturation and/or aggregation of unstable proteins in this context. These additives can be incorporated into polymeric melt processes and compositions within the disclosure. For example, polypeptide microparticles can be prepared by simply lyophilizing or spray drying a solution containing various stabilizing additives described herein. Sustained release of unaggregated peptides and proteins can thereby be obtained over an extended period of time.

Various additional preparative components and methods, as well as specific formulation additives, are provided herein which yield formulations for mucosal delivery of a therapeutically effective amount of aggregation-prone peptides and proteins, wherein the peptide or protein is stabilized in a substantially pure, unaggregated form as a consequence of using a solubilization agent. As used herein, a "therapeutically effective amount" means an amount of an active pharmaceutical ingredient or agent (e.g., a mucosal delivery-enhancing agent) that is sufficient, in the subject (e.g., mammal) in need thereof and to which it is administered, to treat or prevent or otherwise modulate the stated disease, disorder or condition. A range of components and additives are contemplated for use within the methods and formulations of the present disclosure. Exemplary of such solubilization agents are cyclodextrins (CDs) and derivatives thereof, which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation provides additional advantages within the intranasal delivery methods and compositions of the disclosure. Additional agents for use in this context include CD dimers, trimers and tetramers with varying geometries controlled by linkers that specifically block aggregation of peptides and/or protein. Yet solubilization agents and methods for incorporation within this disclosure may involve the use of peptides, peptide derivatives, analogues, and peptide mimetics to selectively block protein-protein interactions. In one aspect, the specific binding of hydrophobic side chains reported for CD multimers is extended to proteins via the use of peptides and peptide mimetics that similarly block protein aggregation. A wide range of suitable methods and anti-aggregation agents are available for incorporation within the compositions and procedures contemplated herein.

Charge Modifying and pH Control Agents and Methods

To improve the transport characteristics of biologically active agents (including a insulin, or other active peptides and proteins, and macromolecular and small molecule drugs) for enhanced delivery across hydrophobic mucosal membrane barriers, this disclosure also provides techniques and reagents for the "charge modification" of selected biologically active agents or delivery-enhancing agents described herein. In this regard, the relative permeability of a macromolecule is generally related to its partition coefficient. A molecules degree of ionization, which is dependent on the $pK_a$ of the molecule and the pH at the mucosal membrane surface, also affects its permeability. As set forth herein, the permeation and partitioning of biologically active agents, including insulin and analogs thereof, for mucosal delivery may be facilitated by charge alteration or charge spreading of the active agent or permeabilizing agent, which may be achieved, for example, by alteration of charged functional groups, by modifying the pH of the delivery vehicle or solution in which the active agent (or precursor thereto) is delivered, or by coordinate administration of a charge- or pH-altering reagent with the active agent (or precursor).

Consistent with these general teachings, mucosal delivery of charged macromolecular species, including insulin and other biologically active peptides and proteins, within the methods and compositions of this disclosure is substantially improved when the active agent is delivered to the mucosal surface in a substantially un-ionized, or neutral, electrical charge state.

Certain insulin(s) and other biologically active peptide and protein components of one or more mucosal formulations within this disclosure may be charge modified in order to provide an increase in the positive charge density of the peptide or protein. These modifications extend also to cationization of peptide and protein conjugates, carriers and other delivery forms disclosed herein. Cationization offers a convenient means of altering the biodistribution and transport properties of proteins and macromolecules within this disclosure. Cationization is undertaken in a manner that substantially preserves the biological activity of the active agent and limits potentially adverse side effects, including tissue damage and toxicity.

A "buffer" is generally used to maintain the pH of a solution at a nearly constant value. A buffer maintains the pH of a solution, even when small amounts of strong acid or strong base are added to the solution, by preventing or neutralizing large changes in concentrations of hydrogen and hydroxide ions. A buffer generally consists of a weak acid and its appropriate salt (or a weak base and its appropriate salt). The appropriate salt for a weak acid contains the same negative ion as present in the weak acid (see Lagowski, *Macmillan Encyclopedia of Chemistry* 1:273-4, 1997, Simon & Schuster, New York. The Henderson-Hasselbach Equation, pH=pKa+log 10 [A−]/[HA], is used to describe a buffer, and is based on the standard equation for weak acid dissociation, HA⇌[H+]+[A−]. Examples of commonly used buffer salts include the following: glutamate, acetate, citrate, glycine, histidine, arginine, lysine, methionine, lactate, formate, glycolate, tartrate, phosphate and mixtures thereof.

The "buffer capacity" means the amount of acid or base that can be added to a buffer solution before a significant pH change will occur. If the pH lies within the range of pK−1 and pK+1 of the weak acid the buffer capacity is appreciable, but outside this range it falls off to such an extent as to be of little value. Therefore, a given system only has a useful buffer action in a range of one pH unit on either side of the pK of the weak acid (or weak base) (see Dawson, *Data for Biochemical Research*, Third Edition, Oxford Science Publications, 1986, p. 419). Generally, suitable concentrations are chosen so that the pH of the solution is close to the pKa of the weak acid (or weak base) (see Lide, *CRC Handbook of Chemistry and Physics*, 86th Edition, Taylor & Francis Group, 2005-2006, p. 2-41). Further, solutions of strong acids and bases are not normally classified as buffer solutions, and they do not display buffer capacity between pH values 2.4 to 11.6.

Degradative Enzyme Inhibitory Agents and Methods

Another excipient that may be included in a trans-mucosal delivery formulation is a degradative enzyme inhibitor. Exemplary mucoadhesive polymer-enzyme inhibitor complexes that are useful within the mucosal delivery formulations and methods of this disclosure include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil-elastatinal (anti-elastase); Chitosan-antipain (anti-trypsin); Poly(acrylic acid)-bacitracin (anti-aminopeptidase N); Chitosan-EDTA (anti-aminopeptidase N, anti-carboxypeptidase A); Chitosan-EDTA-antipain (anti-trypsin, anti-chymotrypsin, anti-elastase). As described in further detail below, certain embodiments of this disclosure incorporate a novel chitosan derivative or chemically modified form of chitosan. One such novel derivative within this disclosure is denoted as a β-[1→4]-2-guanidino-2-deoxy-D-glucose polymer (poly-GuD).

Any inhibitor that inhibits the activity of an enzyme (e.g., a protease) to protect the biologically active agent(s) may be usefully employed in the compositions and methods of this disclosure. Useful enzyme inhibitors for the protection of biologically active proteins and peptides include, for example, soybean trypsin inhibitor, exendin trypsin inhibitor, chymotrypsin inhibitor and trypsin and chrymotrypsin inhibitor isolated from potato (*solanum tuberosum* L.) tubers. A combination or mixtures of inhibitors may be employed. Additional inhibitors of proteolytic enzymes within this disclosure include ovomucoid-enzyme, gabaxate mesylate, alpha1-antitrypsin, aprotinin, amastatin, bestatin, puromycin, bacitracin, leupepsin, alpha2-macroglobulin, pepstatin and egg white or soybean trypsin inhibitor. These and other inhibitors can be used alone or in any combination. The inhibitor(s) may be incorporated in or bound to a carrier, e.g., a hydrophilic polymer, coated on the surface of the dosage form which is to contact the nasal mucosa, or incorporated in the superficial phase of the surface, in combination with the biologically active agent or in a separately administered (e.g., pre-administered) formulation.

The amount of the inhibitor, e.g., of a proteolytic enzyme inhibitor that is optionally incorporated in the compositions of this disclosure will vary depending on (a) the properties of the specific inhibitor, (b) the number of functional groups present in the molecule (which may be reacted to introduce ethylenic unsaturation necessary for copolymerization with hydrogel forming monomers), and (c) the number of lectin groups, such as glycosides, which are present in the inhibitor molecule. It may also depend on the specific therapeutic agent that is intended to be administered. A useful amount of an enzyme inhibitor may be from about 0.1 mg/ml to about 50 mg/ml, often from about 0.2 mg/ml to about 25 mg/ml, and more commonly from about 0.5 mg/ml to about 5 mg/ml of the of the formulation (i.e., a separate protease inhibitor formulation or combined formulation with the inhibitor and biologically active agent).

In the case of trypsin inhibition, suitable inhibitors may be selected from, e.g., aprotinin, BBI, soybean trypsin inhibitor, chicken ovomucoid, chicken ovoinhibitor, human exendin trypsin inhibitor, camostat mesilate, flavonoid inhibitors, antipain, leupeptin, p-aminobenzamidine, AEBSF, TLCK (tosyllysine chloromethylketone), APMSF, DFP, PMSF, and poly(acrylate) derivatives. In the case of chymotrypsin inhibition, suitable inhibitors may be selected from, e.g., aprotinin, BBI, soybean trypsin inhibitor, chymostatin, benzyloxycarbonyl-Pro-Phe-CHO, FK-448, chicken ovoinhibitor, sugar biphenylboronic acids complexes, DFP, PMSF, β-phenylpropionate, and poly(acrylate) derivatives. In the case of elastase inhibition, suitable inhibitors may be selected from, e.g., elastatinal, methoxysuccinyl-Ala-Ala-Pro-Val-chloromethylketone (MPCMK), BBI, soybean trypsin inhibitor, chicken ovoinhibitor, DFP, and PMSF.

Additional enzyme inhibitors within this disclosure are selected from a wide range of non-protein inhibitors that vary in their degree of potency and toxicity. As described in further detail below, immobilization of these adjunct agents to matrices or other delivery vehicles, or development of chemically modified analogues, may be readily implemented to reduce or even eliminate toxic effects, when they are encountered. Among this broad group of candidate enzyme inhibitors within this disclosure are organophosphorous inhibitors, such as diisopropylfluorophosphate (DFP) and phenylmethylsulfonyl fluoride (PMSF), which are potent, irreversible inhibitors of serine proteases (e.g., trypsin and chymotrypsin). The additional inhibition of acetylcholinesterase by these compounds makes them highly toxic in uncontrolled delivery settings. Another candidate inhibitor, 4-(2-Aminoethyl)-benzenesulfonyl fluoride (AEBSF), has an inhibitory activity comparable to DFP and PMSF, but it is markedly less toxic. (4-Aminophenyl)-methanesulfonyl fluoride hydrochloride (APMSF) is another potent inhibitor of trypsin, but is toxic in uncontrolled settings. In contrast to these inhibitors, 4-(4-isopropylpiperadinocarbonyl)phenyl 1,2,3,4,-tetrahydro-1-naphthoate methanesulphonate (FK-448) is a low toxic substance, representing a potent and specific inhibitor of chymotrypsin. Further representatives of this non-protein group of inhibitor candidates, and also exhibiting low toxic risk, are camostat mesilate (N,N'-dimethyl carbamoylmethyl-p-(p'-guanidino-benzoyloxy)phenylacetate methane-sulphonate).

Yet another type of enzyme inhibitory agent within the methods and compositions of this disclosure are amino acids and modified amino acids that interfere with enzymatic degradation of specific therapeutic compounds. For use in this context, amino acids and modified amino acids are substantially non-toxic and can be produced at a low cost. However, due to their low molecular size and good solubility, they are readily diluted and absorbed in mucosal environments. Nevertheless, under proper conditions, amino acids can act as reversible, competitive inhibitors of protease enzymes. Certain modified amino acids can display a much stronger inhibitory activity. A desired modified amino acid in this context is known as a 'transition-state' inhibitor. The strong inhibitory activity of these compounds is based on their structural similarity to a substrate in its transition-state geometry, while they are generally selected to have a much higher affinity for the active site of an enzyme than the substrate itself. Transition-state inhibitors are reversible, competitive inhibitors. Examples of this type of inhibitor are α-aminoboronic acid derivatives, such as boro-leucine, boro-valine and boro-alanine. The boron atom in these derivatives can form a tetrahedral boronate ion that is believed to resemble the transition state of peptides during their hydrolysis by aminopeptidases. Such amino acid derivatives are potent and reversible inhibitors of aminopeptidases and it is reported that boro-leucine is more than 100-times more effective in enzyme inhibition than bestatin and more than 1000-times more effective than puromycin. Another modified amino acid for which a strong protease inhibitory activity has been reported is N-acetylcysteine, which inhibits enzymatic activity of aminopeptidase N. This adjunct agent also displays mucolytic properties that can be employed within the methods and compositions of this disclosure to reduce the effects of the mucus diffusion barrier.

Still other useful enzyme inhibitors for use within the coordinate administration methods and combinatorial formulations of this disclosure may be selected from peptides and modified peptide enzyme inhibitors. An important representative of this class of inhibitors is the cyclic dodecapeptide, bacitracin, obtained from *Bacillus licheniformis*. In addition to these types of peptides, certain dipeptides and tripeptides display weak, non-specific inhibitory activity towards some protease. By analogy with amino acids, their inhibitory activity can be improved by chemical modifications. For example, phosphinic acid dipeptide analogues are also 'transition-state' inhibitors with a strong inhibitory activity towards aminopeptidases. They have reportedly been used to stabilize nasally administered leucine enkephalin. Another example of a transition-state analogue is the modified pentapeptide pepstatin, which is a very potent inhibitor of pepsin. Structural analysis of pepstatin, by testing the inhibitory activity of several synthetic analogues, demonstrated the major structure-function characteristics of the molecule responsible for the inhibitory activity. Another special type of modified peptide includes inhibitors with a terminally located aldehyde function in their structure. For example, the sequence benzyloxycarbonyl-Pro-Phe-CHO, which fulfills the known primary and secondary specificity requirements of chymotrypsin, has been found to be a potent reversible inhibitor of this target proteinase. The chemical structures of further inhibitors with a terminally located aldehyde function, e.g., antipain, leupeptin, chymostatin and elastatinal, are also known in the art, as are the structures of other known, reversible, modified peptide inhibitors, such as phosphoramidon, bestatin, puromycin and amastatin.

Due to their comparably high molecular mass, polypeptide protease inhibitors are more amenable than smaller compounds to concentrated delivery in a drug-carrier matrix. Additional agents for protease inhibition within the formulations and methods of this disclosure involve the use of complexing agents. These agents mediate enzyme inhibition by depriving the intranasal environment (or preparative or therapeutic composition) of divalent cations, which are co-factors for many proteases. For instance, the complexing agents EDTA and DTPA as coordinately administered or combinatorially formulated adjunct agents, in suitable concentration, will be sufficient to inhibit selected proteases to thereby enhance intranasal delivery of biologically active agents according to this disclosure. Further representatives of this class of inhibitory agents are EGTA, 1,10-phenanthroline and hydroxychinoline. In addition, due to their propensity to chelate divalent cations, these and other complexing agents are useful within this disclosure as direct absorption-promoting agents.

As noted in more detail elsewhere herein, it is also contemplated to use various polymers, particularly mucoadhesive polymers, as enzyme inhibiting agents within the coordinate administration, multi-processing and/or combinatorial formulation methods and compositions of this disclosure. For example, poly(acrylate) derivatives, such as poly(acrylic acid) and polycarbophil, can affect the activity of various proteases, including trypsin, chymotrypsin. The inhibitory effect of these polymers may also be based on the complexation of divalent cations such as $Ca^{2+}$ and $Zn^{2+}$. It is further contemplated that these polymers may serve as conjugate partners or carriers for additional enzyme inhibitory agents, as described above. For example, a chitosan-EDTA conjugate has been developed and is useful within this disclosure that exhibits a strong inhibitory effect towards the enzymatic activity of zinc-dependent proteases. The mucoadhesive properties of polymers following covalent attachment of other enzyme inhibitors in this context are not expected to be substantially compromised, nor is the general utility of such polymers as a delivery vehicle for biologically active agents within this disclosure expected to be diminished. On the contrary, the reduced distance between the delivery vehicle and mucosal surface afforded by the mucoadhesive mechanism will minimize presystemic metabolism of the active agent, while the covalently bound enzyme inhibitors remain concentrated at the site of drug delivery, minimizing undesired dilution effects of inhibitors as well as toxic and other side effects caused thereby. In this manner, the effective amount of a coordinately administered enzyme inhibitor can be reduced due to the exclusion of dilution effects.

Exemplary mucoadhesive polymer-enzyme inhibitor complexes that are useful within the mucosal formulations and methods of this disclosure include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil-elastatinal (anti-elastase); Chitosan-antipain (anti-trypsin); Poly(acrylic acid)-bacitracin (anti-aminopeptidase N); Chitosan-EDTA (anti-aminopeptidase N, anti-carboxypeptidase A); Chitosan-EDTA-antipain (anti-trypsin, anti-chymotrypsin, anti-elastase).

Mucolytic and Mucus-Clearing Agents and Methods

Effective delivery of biotherapeutic agents via intranasal administration must take into account the decreased drug transport rate across the protective mucus lining of the nasal mucosa, in addition to drug loss due to binding to glycoproteins of the mucus layer. Normal mucus is a viscoelastic, gel-like substance consisting of water, electrolytes, mucins, macromolecules, and sloughed epithelial cells. It serves primarily as a cytoprotective and lubricative covering for the underlying mucosal tissues. Mucus is secreted by randomly distributed secretory cells located in the nasal epithelium and in other mucosal epithelia. The structural unit of mucus is mucin. This glycoprotein is mainly responsible for the viscoelastic nature of mucus, although other macromolecules may also contribute to this property. In airway mucus, such macromolecules include locally produced secretory IgA, IgM, IgE, lysozyme, and bronchotransferrin, which also play an important role in host defense mechanisms.

The coordinate administration methods of the instant disclosure optionally incorporate effective mucolytic or mucus-clearing agents, which serve to degrade, thin or clear mucus from intranasal mucosal surfaces to facilitate absorption of intranasally administered biotherapeutic agents. Within these methods, a mucolytic or mucus-clearing agent is coordinately administered as an adjunct compound to enhance intranasal delivery of the biologically active agent. Alternatively, an effective amount of a mucolytic or mucus-clearing agent is incorporated as a processing agent within a multi-processing method of this disclosure, or as an additive within a combinatorial formulation of this disclosure, to provide an improved formulation that enhances intranasal delivery of biotherapeutic compounds by reducing the barrier effects of intranasal mucus.

A variety of mucolytic or mucus-clearing agents are available for incorporation within the methods and compositions of this disclosure. Based on their mechanisms of action, mucolytic and mucus clearing agents can often be classified into the following groups: proteases (e.g., pronase, papain) that cleave the protein core of mucin glycoproteins; sulfhydryl compounds that split mucoprotein disulfide linkages; and detergents (e.g., Triton X-100, Tween 20) that break non-covalent bonds within the mucus. Additional compounds in this context include, but are not limited to, bile salts and surfactants, for example, sodium deoxycholate, sodium taurodeoxycholate, sodium glycocholate, and lysophosphatidylcholine.

The effectiveness of bile salts in causing structural breakdown of mucus is in the order deoxycholate>taurocholate>glycocholate. Other effective agents that reduce mucus viscosity or adhesion to enhance intranasal delivery according to the methods of this disclosure include, e.g., short-chain fatty acids, and mucolytic agents that work by chelation, such as N-acylcollagen peptides, bile acids, and saponins (the latter function in part by chelating $Ca^{2+}$ and/or $Mg^{2+}$ which play an important role in maintaining mucus layer structure).

Additional mucolytic agents for use within the methods and compositions of this disclosure include N-acetyl-L-cysteine (ACS), a potent mucolytic agent that reduces both the viscosity and adherence of bronchopulmonary mucus and is reported to modestly increase nasal bioavailability of human growth hormone in anesthetized rats (from 7.5 to 12.2%). These and other mucolytic or mucus-clearing agents are contacted with the nasal mucosa, typically in a concentration range from about 0.2 to about 20 mM, coordinately with administration of the biologically active agent, to reduce the polar viscosity and/or elasticity of intranasal mucus.

Still other mucolytic or mucus-clearing agents may be selected from a range of glycosidase enzymes, which are able to cleave glycosidic bonds within the mucus glycoprotein. α-amylase and β-amylase are representative of this class of enzymes, although their mucolytic effect may be limited. In contrast, bacterial glycosidases allow these microorganisms to permeate mucus layers of their hosts.

For combinatorial use with most biologically active agents within this disclosure, including peptide and protein therapeutics, non-ionogenic detergents are generally also useful as mucolytic or mucus-clearing agents. These agents typically will not modify or substantially impair the activity of therapeutic polypeptides.

Ciliostatic Agents and Methods

Because the self-cleaning capacity of certain mucosal tissues (e.g., nasal mucosal tissues) by mucociliary clearance is necessary as a protective function (e.g., to remove dust, allergens, and bacteria), it is appreciated that this function should not be substantially impaired by mucosally administered medications. Mucociliary transport in the respiratory tract is a particularly important defense mechanism against infections. To achieve this function, ciliary beating in the nasal and airway passages moves a layer of mucus along the mucosa to removing inhaled particles and microorganisms.

Ciliostatic agents find use within the methods and compositions of this disclosure to increase the residence time of a mucosally (e.g., intranasally) administered formulation comprising an insulin, analog and mimetic, and other biologically active agent disclosed herein. In particular, the delivery of such agents within the methods and compositions of this disclosure is significantly enhanced in certain aspects by the coordinate administration or combinatorial formulation of one or more ciliostatic agents that function to reversibly inhibit the ciliary activity of mucosal cells, and thereby to provide for a temporary, reversible increase in the residence time of the mucosally administered pharmaceutically active agent(s). For use within these aspects of this disclosure, the ciliostatic factors set forth herein, either specific or indirect in their activity, are all candidates for successful employment as a ciliostatic agent in appropriate amounts (depending on concentration, duration and mode of delivery) such that they yield a transient (i.e., reversible) reduction or cessation of mucociliary clearance at a mucosal site of administration to enhance delivery of an insulin, analogs and/or mimetics, and other biologically active agents disclosed herein, without unacceptable adverse side effects.

Within more detailed aspects, a specific ciliostatic factor may be employed in a combined formulation or coordinate administration protocol with one or more insulin protein, analog and mimetic, and/or one or more other biologically active agent disclosed herein. Various bacterial ciliostatic factors isolated and characterized in the literature may be employed within certain embodiments of this disclosure. For example, ciliostatic factors from the bacterium *Pseudomonas aeruginosa* include a phenazine derivative, a pyo compound (2-alkyl-4-hydroxyquinolines), and a rhamnolipid (also known as a hemolysin). The pyo compound produced ciliostasis at concentrations of 50 μg/ml and without obvious ultrastructural lesions. The phenazine derivative also inhibited ciliary motility but caused some membrane disruption, although at substantially greater concentrations of 400 μg/ml. Limited exposure of tracheal explants to the rhamnolipid resulted in ciliostasis, which is associated with altered ciliary membranes. More extensive exposure to rhamnolipid is associated with removal of dynein arms from axonemes.

Surface Active Agents and Methods

Within more detailed aspects of this disclosure, one or more membrane penetration-enhancing agents may be employed within a mucosal delivery method or formulation of this disclosure to enhance mucosal delivery of insulin proteins, analogs and mimetics, and other biologically active agents disclosed herein. Membrane penetration enhancing agents in this context can be selected from: (i) a surfactant; (ii) a bile salt; (iii) a phospholipid additive, mixed micelle, liposome, or carrier; (iv) an alcohol; (v) an enamine; (vi) an NO donor compound; (vii) a long-chain amphipathic molecule; (viii) a small hydrophobic penetration enhancer; (ix) sodium or a salicylic acid derivative; (x) a glycerol ester of acetoacetic acid; (xi) a cyclodextrin or beta-cyclodextrin derivative; (xii) a medium-chain fatty acid; (xiii) a chelating agent; (xiv) an amino acid or salt thereof; (xv) an N-acetylamino acid or salt thereof; (xvi) an enzyme degradative to a selected membrane component; (xvii) an inhibitor of fatty acid synthesis; (xviii) an inhibitor of cholesterol synthesis; or (xix) any combination of the membrane penetration enhancing agents recited in (i)-(xviii).

Certain surface-active agents, also called surfactants, are readily incorporated within the mucosal delivery formulations and methods of this disclosure as mucosal absorption enhancing agents. These agents, which may be coordinately administered or combinatorially formulated with insulin proteins, analogs and mimetics, and other biologically active agents disclosed herein, may be selected from a broad assemblage of known surfactants. Surfactants, which generally fall into three classes: (1) nonionic polyoxyethylene ethers; (2) bile salts such as sodium glycocholate (SGC) and deoxycholate (DOC); and (3) fusidic acid and derivatives of fusidic acid such as sodium taurodihydrofusidate (STDHF). The mechanisms of action of these various classes of surface-active agents typically include solubilization of the biologically active agent. For proteins and peptides which often form aggregates, the surface active properties of these absorption promoters can allow interactions with proteins such that smaller units such as surfactant coated monomers may be more readily maintained in solution. These monomers are presumably more transportable units than aggregates. Examples of other surface-active agents are L-α-Phosphatidylcholine Didecanoyl (DDPC), polysorbate 80 and polysorbate 20. Additional surface-acting agents include polyethylene glycol, cetyl alcohol, polyvinylpyrolidone, polyvinyl alcohol, lanolin alcohol, sorbitan monooleate. All surface-acting agents of the instant disclosure may be present in a pharmaceutical formulation alone or in any mixture or combination. A second potential mechanism is the protection of the peptide or protein from proteolytic degradation by proteases in the mucosal environment. Both bile salts and some fusidic acid derivatives reportedly inhibit proteolytic degradation of proteins by nasal homogenates at concentrations less than or equivalent to those required to enhance protein absorption. This protease inhibition may be especially important for peptides with short biological half-lives.

Thickening Agents

Thickening or suspending agents may affect the rate of release of a drug from the dosage formulation and/or absorption. Some examples of the materials which can serve as pharmaceutically acceptable thickening agents are gelatin; methylcellulose (MC); hydroxypropylmethylcellulose (HPMC) and derivatives thereof; carboxymethylcellulose (CMC); cellulose; starch; heta starch; poloxamers; pluronics; sodium CMC; sorbitol; acacia; povidone; carbopol (as used herein, carbopol is a carbomer; carbopol is also known as Carbomer Homopolymer Type B, or Carbopol® 974P NF Polymer); polycarbophil; chitosan; chitosan microspheres; alginate microspheres; chitosan glutamate; amberlite resin; hyaluronan; ethyl cellulose; maltodextrin DE; drum-dried way maize starch (DDWM); degradable starch microspheres (DSM); deoxyglycocholate (GDC); hydroxyethyl cellulose (HEC); hydroxypropyl cellulose (HPC); microcrystalline cellulose (MCC); polymethacrylic acid and polyethylene glycol; sulfobutylether B cyclodextrin; cross-linked eldexomer starch biospheres; sodiumtaurodihydrofusidate (STDHF); N-trimethyl chitosan chloride (TMC); degraded starch microspheres; amberlite resin; chistosan nanoparticles; spray-dried crospovidone; spray-dried dextran microspheres; spray-dried microcrystalline cellulose; and cross-linked eldexomer starch microspheres.

As used herein, a carbomer thickening agent also includes, but is not limited to, the following: Acrylic acid homopolymer, Acrylic acid resin, Acrylic acid, polymer, Acrylic polymer, Acrylic resin, Acrysol A 1, Acrysol A 3, Acrysol A 5, Acrysol AC 5, Acrysol WS-24, Acrysol ase-75, Antiprex 461, Antiprex A, Arasorb 750, Arasorb S100F, Arolon, Aron, Aron A 10H, Atactic poly(acrylic acid), CCRIS 3234, Carbomer 1342, Carbomer 910, Carbopol 1342, Carbopol 910, Carbopol 934, Carbopol 934P, Carbopol 940, Carbopol 941, Carbopol 960, Carbopol 961, Carbopol 971P, Carbopol 974P, Carbopol 980, Carbopol 981, Carboset 515, Carboset Resin No. 515, Carboxy vinyl polymer, Carboxypolymethylene, Carpolene, Colloids 119/50, Cyguard 266, Dispex C40, Dow Latex 354, G-Cure, Good-rite K 37, Good-rite K 702, Good-rite K 732, Good-rite K-700, Good-rite K727, Good-rite WS 801, Haloflex 202, Haloflex 208, Joncryl 678, Junlon 110, Jurimer AC 10H, Jurimer AC 10P, NSC 106034, NSC 106035, NSC 106036, NSC 106037, NSC 112122, NSC 112123, NSC 114472, NSC 165257, Nalfloc 636, Neocryl A-1038, OLD 01, P 11H, P 11H, P-11H, PA 11M, PAA-25, Pemulen TR-1, Pemulen TR-2, Poly(acrylic acid), Polyacrylate, Polyacrylate elastomers, Polymer of acrylic acid, cross-linked with allyl ethers of pentaerythritol, Polymer of acrylic acid, cross-linked with allyl ethers of pentaerythritol. Those where the molecular weight is approximately 1,250,000 such as Polymer of acrylic acid, cross-linked with allyl ethers of pentaerythritol. Those where the molecular weight is approximately 750,000 such as Polymer of acrylic acid, cross-linked with allyl ethers of sucrose or pentaerythritol, Polymer of acrylic acid, cross-linked with allyl ethers of sucrose or pentaerythritol. Those where the molecular weight is approximately 3,000,000 such as Polymer of acrylic acid, cross-linked with allyl ethers of sucrose. Those where the molecular weight is approximately 3,000,000 Polymer, carboxy vinyl Polymerized acrylic acid, Polytex 973, Primal ASE 60, Propenoic acid polymer, R968, Racryl, Revacryl A 191, Rohagit SD 15, Sokalan PAS, Solidokoll N, Synthemul 90-588, TB 1131, Tecpol, Texcryl, Versicol E 7, Versicol E15, Versicol E9, Versicol K 11, Versicol S 25, Viscalex HV 30, Viscon 103, WS 24, WS 801, XPA and the like.

Other thickening agents in Ugwoke et al., *Adv. Drug Deliv. Rev.* 29:1656-57, 1998, are incorporated by reference. Any one thickening agent or any combination or mixture of thickening increasing agents may be contained in a pharmaceutical formulation disclosed herein.

Degradation Enzymes and Inhibitors of Fatty Acid and Cholesterol Synthesis

In related aspects of this disclosure, insulin proteins, analogs and mimetics, and other biologically active agents for mucosal administration are formulated or coordinately administered with a penetration enhancing agent selected from a degradation enzyme, or a metabolic stimulatory agent or inhibitor of synthesis of fatty acids, sterols or other selected epithelial barrier components, U.S. Pat. No. 6,190,894. For example, degradative enzymes such as phospholipase, hyaluronidase, neuraminidase, and chondroitinase may be employed to enhance mucosal penetration of insulin proteins, analogs and mimetics, and other biologically active agent without causing irreversible damage to the mucosal barrier. In one embodiment, chondroitinase is employed within a method or composition as provided herein to alter glycoprotein or glycolipid constituents of the permeability barrier of the mucosa, thereby enhancing mucosal absorption of insulin proteins, analogs and mimetics, and other biologically active agents disclosed herein.

With regard to inhibitors of synthesis of mucosal barrier constituents, it is noted that free fatty acids account for 20-25% of epithelial lipids by weight. Two rate-limiting enzymes in the biosynthesis of free fatty acids are acetyl CoA carboxylase and fatty acid synthetase. Through a series of steps, free fatty acids are metabolized into phospholipids. Thus, inhibitors of free fatty acid synthesis and metabolism for use within the methods and compositions of this disclosure include, but are not limited to, inhibitors of acetyl CoA carboxylase such as 5-tetradecyloxy-2-furancarboxylic acid (TOFA); inhibitors of fatty acid synthetase; inhibitors of phospholipase A such as gomisin A, 2-(p-amylcinnamyl) amino-4-chlorobenzoic acid, bromophenacyl bromide, monoalide, 7,7-dimethyl-5,8-eicosadienoic acid, nicergoline, cepharanthine, nicardipine, quercetin, dibutyryl-cyclic AMP, R-24571, N-oleoylethanolamine, N-(7-nitro-2,1,3-benzoxadiazol-4-yl)phosphostidyl serine, cyclosporine A, topical anesthetics, including dibucaine, prenylamine, retinoids, such as all-trans and 13-cis-retinoic acid, W-7, trifluoperazine, R-24571 (calmidazolium), 1-hexadocyl-3-trifluoroethyl glycero-sn-2-phosphomenthol (MJ33); calcium channel blockers including nicardipine, verapamil, diltiazem, nifedipine, and nimodipine; antimalarials including quinacrine, mepacrine, chloroquine and hydroxychloroquine; beta blockers including propanalol and labetalol; calmodulin antagonists; EGTA; thimersol; glucocorticosteroids including dexamethasone and prednisolone; and non-steroidal antiinflammatory agents including indomethacin and naproxen.

Free sterols, primarily cholesterol, account for 20-25% of the epithelial lipids by weight. The rate limiting enzyme in the biosynthesis of cholesterol is 3-hydroxy-3-methylglutaryl (HMG) CoA reductase Inhibitors of cholesterol synthesis for use within the methods and compositions of this disclosure include, but are not limited to, competitive inhibitors of (HMG) CoA reductase, such as simvastatin, lovastatin, fluindostatin (fluvastatin), pravastatin, mevastatin, as well as other HMG CoA reductase inhibitors, such as cholesterol oleate, cholesterol sulfate and phosphate, and oxygenated sterols, such as 25-OH— and 26-OH— cholesterol; inhibitors of squalene synthetase; inhibitors of squalene epoxidase; inhibitors of DELTA7 or DELTA24 reductases such as 22,25-diazacholesterol, 20,25-diazacholestenol, AY9944, and triparanol.

Each of the inhibitors of fatty acid synthesis or the sterol synthesis inhibitors may be coordinately administered or combinatorially formulated with one or more insulin proteins, analogs and mimetics, and other biologically active agents disclosed herein to achieve enhanced epithelial penetration of the active agent(s). An effective concentration range for the sterol inhibitor in a therapeutic or adjunct formulation for mucosal delivery is generally from about 0.0001% to about 20% by weight of the total, more typically from about 0.01% to about 5%.

Nitric Oxide Donor Agents and Methods

Within other related aspects of this disclosure, a nitric oxide (NO) donor is selected as a membrane penetration-enhancing agent to enhance mucosal delivery of one or more insulin proteins, analogs and mimetics, and other biologically active agents disclosed herein. Various NO donors are known in the art and are useful in effective concentrations within the methods and formulations of this disclosure. Exemplary NO donors include, but are not limited to, nitroglycerine, nitropruside, NOC5 [3-(2-hydroxy-1-(methyl-ethyl)-2-nitrosohydrazino)-1-propanamine], NOC12 [N-ethyl-2-(1-ethyl-hydroxy-2-nitrosohydrazino)-ethanamine], SNAP [S-nitroso-N-acetyl-DL-penicillamine], NORI and NOR4. Within the methods and compositions of this disclosure, an effective amount of a selected NO donor is coordinately administered or combinatorially formulated with one or more insulin proteins, analogs and mimetics, and/or other biologically active agents disclosed herein, into or through the mucosal epithelium.

Agents for Modulating Epithelial Junction Structure and/or Physiology

The present disclosure provides pharmaceutical compositions that contain one or more insulin protein, analog or mimetic, and/or other biologically active agents in combination with one or more mucosal delivery enhancing agent disclosed herein formulated in such pharmaceutical preparation for mucosal delivery.

The permeabilizing agent reversibly enhances mucosal epithelial paracellular transport, typically by modulating epithelial junctional structure and/or physiology at a mucosal epithelial surface in the subject. This effect typically involves inhibition by the permeabilizing agent of homotypic or heterotypic binding between epithelial membrane adhesive proteins of neighboring epithelial cells. Target proteins for this blockade of homotypic or heterotypic binding can be selected from various related junctional adhesion molecules (JAMs), occludins, or claudins. Examples of this are antibodies, antibody fragments or single-chain antibodies that bind to the extracellular domains of these proteins.

In yet additional detailed embodiments, this disclosure provides permeabilizing peptides and peptide analogs and mimetics for enhancing mucosal epithelial paracellular transport. The subject peptides and peptide analogs and mimetics typically work within the compositions and methods of this disclosure by modulating epithelial junctional structure and/or physiology in a mammalian subject. In certain embodiments, the peptides and peptide analogs and mimetics effectively inhibit homotypic and/or heterotypic binding of an epithelial membrane adhesive protein selected from a junctional adhesion molecule (JAM), occludin, or claudin.

One such agent that has been extensively studied is the bacterial toxin from *Vibrio cholerae* known as the "zonula occludens toxin" (ZOT). This toxin mediates increased intestinal mucosal permeability and causes disease symptoms including diarrhea in infected subjects. Fasano et al., *Proc. Nat. Acad. Sci., U.S.A.* 8:5242-5246, 1991. When tested on rabbit ileal mucosa, ZOT increased the intestinal permeability by modulating the structure of intercellular tight junctions. More recently, it has been found that ZOT is capable of reversibly opening tight junctions in the intestinal mucosa. It has also been reported that ZOT is capable of reversibly opening tight junctions in the nasal mucosa. U.S. Pat. No. 5,908,825.

Within the methods and compositions of this disclosure, ZOT, as well as various analogs and mimetics of ZOT that function as agonists or antagonists of ZOT activity, are useful for enhancing intranasal delivery of biologically active agents—by increasing paracellular absorption into and across the nasal mucosa. In this context, ZOT typically acts by causing a structural reorganization of tight junctions marked by altered localization of the junctional protein ZO1. Within these aspects of this disclosure, ZOT is coordinately administered or combinatorially formulated with the biologically active agent in an effective amount to yield significantly enhanced absorption of the active agent, by reversibly increasing nasal mucosal permeability without substantial adverse side effects.

Vasodilator Agents and Methods

Yet another class of absorption-promoting agents that shows beneficial utility within the coordinate administration and combinatorial formulation methods and compositions of this disclosure are vasoactive compounds, more specifically vasodilators. These compounds function within the present disclosure to modulate the structure and physiology of the submucosal vasculature, increasing the transport rate of insulin, analogs and mimetics thereof, and other biologically active agents into or through the mucosal epithelium and/or to specific target tissues or compartments (e.g., the systemic circulation or central nervous system).

Vasodilator agents for use within this disclosure typically cause submucosal blood vessel relaxation by either a decrease in cytoplasmic calcium, an increase in nitric oxide (NO) or by inhibiting myosin light chain kinase. They are generally divided into 9 classes: calcium antagonists, potassium channel openers, ACE inhibitors, angiotensin-II receptor antagonists, α-adrenergic and imidazole receptor antagonists, β1-adrenergic agonists, phosphodiesterase inhibitors, eicosanoids and NO donors.

Despite chemical differences, the pharmacokinetic properties of calcium antagonists are similar. Absorption into the systemic circulation is high, and these agents therefore undergo considerable first-pass metabolism by the liver, resulting in individual variation in pharmacokinetics. Except for the newer drugs of the dihydropyridine type (amlodipine, felodipine, isradipine, nilvadipine, nisoldipine and nitrendipine), the half-life of calcium antagonists is short. Therefore, to maintain an effective drug concentration for many of these may require delivery by multiple dosing, or controlled release formulations, as described elsewhere herein. Treatment with the potassium channel opener minoxidil may also be limited in manner and level of administration due to potential adverse side effects.

ACE inhibitors prevent conversion of angiotensin-I to angiotensin-II, and are most effective when renin production is increased. Since ACE is identical to kininase-II, which inactivates the potent endogenous vasodilator bradykinin, ACE inhibition causes a reduction in bradykinin degradation. ACE inhibitors provide the added advantage of cardioprotective and cardioreparative effects, by preventing and reversing cardiac fibrosis and ventricular hypertrophy in animal models. The predominant elimination pathway of most ACE inhibitors is via renal excretion. Therefore, renal impairment is associated with reduced elimination and a dosage reduction of 25 to 50% is recommended in patients with moderate to severe renal impairment.

With regard to NO donors, these compounds are particularly useful within this disclosure for their additional effects on mucosal permeability. In addition to the above-noted NO donors, complexes of NO with nucleophiles called NO/nucleophiles, or NONOates, spontaneously and nonenzymatically release NO when dissolved in aqueous solution at physiologic pH. In contrast, nitro vasodilators such as nitroglycerin require specific enzyme activity for NO release. NONOates release NO with a defined stoichiometry and at predictable rates ranging from <3 minutes for diethylamine/NO to approximately 20 hours for diethylenetriamine/NO (DETANO).

Within certain methods and compositions of this disclosure, a selected vasodilator agent is coordinately administered (e.g., systemically or intranasally, simultaneously or in combinatorially effective temporal association) or combinatorially formulated with one or more insulin, analogs and mimetics, and other biologically active agent(s) in an amount effective to enhance the mucosal absorption of the active agent(s) to reach a target tissue or compartment in the subject (e.g., the liver, hepatic portal vein, CNS tissue or fluid, or blood plasma).

Selective Transport-Enhancing Agents and Methods

The compositions and delivery methods of this disclosure optionally incorporate a selective transport-enhancing agent that facilitates transport of one or more biologically active agents. These transport-enhancing agents may be employed in a combinatorial formulation or coordinate administration protocol with one or more of the insulin proteins, analogs and mimetics disclosed herein, to coordinately enhance delivery of one or more additional biologically active agent(s) across mucosal transport barriers, to enhance mucosal delivery of the active agent(s) to reach a target tissue or compartment in the subject (e.g., the mucosal epithelium, liver, CNS tissue or fluid, or blood plasma). Alternatively, the transport-enhancing agents may be employed in a combinatorial formulation or coordinate administration protocol to directly enhance mucosal delivery of one or more of the insulin proteins, analogs and mimetics, with or without enhanced delivery of an additional biologically active agent.

Exemplary selective transport-enhancing agents for use within this aspect of this disclosure include, but are not limited to, glycosides, sugar-containing molecules, and binding agents such as lectin binding agents, which are known to interact specifically with epithelial transport barrier components. For example, specific "bioadhesive" ligands, including various plant and bacterial lectins, which bind to cell surface sugar moieties by receptor-mediated interactions can be employed as carriers or conjugated transport mediators for enhancing mucosal, e.g., nasal delivery of biologically active agents within this disclosure. Certain bioadhesive ligands within this disclosure will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of one or more insulin proteins, analogs and mimetics, and other biologically active agent(s) into and/or through mucosal epithelia. These and other selective transport-enhancing agents significantly enhance mucosal delivery of macromolecular biopharmaceuticals (particularly peptides, proteins, oligonucleotides and polynucleotide vectors) within this disclosure. Lectins are plant proteins that bind to specific sugars found on the surface of glycoproteins and glycolipids of eukaryotic cells. Concentrated solutions of lectins have a 'mucotractive' effect, and various studies have demonstrated rapid receptor mediated endocytocis (RME) of lectins and lectin conjugates (e.g., concanavalin A conjugated with colloidal gold particles) across mucosal surfaces. Additional studies have reported that the uptake mechanisms for lectins can be utilized for intestinal drug targeting in vivo. In certain of these studies, polystyrene nanoparticles (500 nm) were covalently coupled to tomato lectin and reported yielded improved systemic uptake after oral administration to rats.

In addition to plant lectins, microbial adhesion and invasion factors provide a rich source of candidates for use as adhesive/selective transport carriers within the mucosal delivery methods and compositions of this disclosure. Two components are necessary for bacterial adherence processes, a bacterial 'adhesin' (adherence or colonization factor) and a receptor on the host cell surface. Bacteria causing mucosal infections need to penetrate the mucus layer before attaching themselves to the epithelial surface. This attachment is usually mediated by bacterial fimbriae or pilus structures, although other cell surface components may also take part in the process. Adherent bacteria colonize mucosal epithelia by multiplication and initiation of a series of biochemical reactions inside the target cell through signal transduction mechanisms (with or without the help of toxins). Associated with these invasive mechanisms, a wide diversity of bioadhesive proteins (e.g., invasin, internalin) originally produced by various bacteria and viruses are known. These allow for extracellular attachment of such microorganisms with an impressive selectivity for host species and even particular target tissues. Signals transmitted by such receptor-ligand interactions trigger the transport of intact, living microorganisms into, and eventually through, epithelial cells by endo- and transcytotic processes. Such naturally occurring phenomena may be harnessed (e.g., by complexing biologically active agents such as insulin with an adhesin) according to the teachings herein for enhanced delivery of biologically active compounds into or across mucosal epithelia and/or to other designated target sites of drug action.

Various bacterial and plant toxins that bind epithelial surfaces in a specific, lectin-like manner are also useful within the methods and compositions of this disclosure. For example, diphtheria toxin (DT) enters host cells rapidly by RME. Likewise, the B subunit of the *E. coli* heat labile toxin binds to the brush border of intestinal epithelial cells in a highly specific, lectin-like manner. Uptake of this toxin and transcytosis to the basolateral side of the enterocytes has been reported in vivo and in vitro. Other researches have expressed the transmembrane domain of diphtheria toxin in *E. coli* as a maltose-binding fusion protein and coupled it chemically to high-Mw poly-L-lysine. The resulting complex is successfully used to mediate internalization of a reporter gene in vitro. In addition to these examples, *Staphylococcus aureus* produces a set of proteins (e.g., staphylococcal enterotoxin A (SEA), SEB, toxic shock syndrome toxin 1 (TSST-1) which act both as superantigens and toxins. Studies relating to these proteins have reported dose-dependent, facilitated transcytosis of SEB and TSST-1 in Caco-2 cells.

Viral haemagglutinins comprise another type of transport agent to facilitate mucosal delivery of biologically active agents within the methods and compositions of this disclosure. The initial step in many viral infections is the binding of surface proteins (haemagglutinins) to mucosal cells. These binding proteins have been identified for most viruses, including rotaviruses, varicella zoster virus, semliki forest virus, adenoviruses, potato leafroll virus, and reovirus. These and other exemplary viral hemagglutinins can be employed in a combinatorial formulation (e.g., a mixture or conjugate formulation) or coordinate administration protocol with one or more of the insulin, analogs and mimetics disclosed herein, to coordinately enhance mucosal delivery of one or more additional biologically active agent(s). Alternatively, viral hemagglutinins can be employed in a combinatorial formulation or coordinate administration protocol to directly enhance mucosal delivery of one or more of the insulin proteins, analogs and mimetics, with or without enhanced delivery of an additional biologically active agent.

A variety of endogenous, selective transport-mediating factors are also available for use within this disclosure. Mammalian cells have developed an assortment of mechanisms to facilitate the internalization of specific substrates and target these to defined compartments. Collectively, these processes of membrane deformations are termed 'endocytosis' and comprise phagocytosis, pinocytosis, receptor-mediated endocytosis (clathrin-mediated RME), and potocytosis (non-clathrin-mediated RME). RME is a highly specific cellular biologic process by which, as its name implies, various ligands bind to cell surface receptors and are subsequently internalized and trafficked within the cell. In many cells the process of endocytosis is so active that the entire membrane surface is internalized and replaced in less than a half hour. Two classes of receptors are proposed based on their orientation in the cell membrane; the amino terminus of Type I receptors is located on the extracellular side of the membrane, whereas Type II receptors have this same protein tail in the intracellular milieu.

Still other embodiments of this disclosure utilize transferrin as a carrier or stimulant of RME of mucosally delivered biologically active agents. Transferrin, an 80 kDa iron-transporting glycoprotein, is efficiently taken up into cells by RME. Transferrin receptors are found on the surface of most proliferating cells, in elevated numbers on erythroblasts and on many kinds of tumors. The transcytosis of transferrin (Tf) and transferrin conjugates is reportedly enhanced in the presence of Brefeldin A (BFA), a fungal metabolite. In other studies, BFA treatment has been reported to rapidly increase apical endocytosis of both ricin and HRP in MDCK cells. Thus, BFA and other agents that stimulate receptor-mediated transport can be employed within the methods of this disclosure as combinatorially formulated (e.g., conjugated) and/or coordinately administered agents to enhance receptor-mediated transport of biologically active agents, including insulin proteins, analogs and mimetics.

Polymeric Delivery Vehicles and Methods

Within certain aspects of the disclosure, insulin proteins, analogs and mimetics, other biologically active agents disclosed herein, and delivery-enhancing agents as described herein, are, individually or combinatorially, incorporated within a mucosally (e.g., nasally) administered formulation that includes a biocompatible polymer functioning as a carrier or base. Such polymer carriers include polymeric powders, matrices or microparticulate delivery vehicles, among other polymer forms. The polymer can be of plant, animal, or synthetic origin. Often the polymer is crosslinked. Additionally, in these delivery systems the insulin, analog or mimetic, can be functionalized in a manner where it can be covalently bound to the polymer and rendered inseparable from the polymer by simple ishing. In other embodiments, the polymer is chemically modified with an inhibitor of enzymes or other agents which may degrade or inactivate the biologically active agent(s) and/or delivery enhancing agent(s). In certain formulations, the polymer is a partially or completely water insoluble but water swellable polymer, e.g., a hydrogel. Polymers in this aspect of this disclosure are desirably water interactive and/or hydrophilic in nature to absorb significant quantities of water, and they often form hydrogels when placed in contact with water or aqueous media for a period of time sufficient to reach equilibrium with water. In more detailed embodiments, the polymer is a hydrogel which, when placed in contact with excess water, absorbs at least two times its weight of water at equilibrium when exposed to water at room temperature, U.S. Pat. No. 6,004,583.

Drug delivery systems based on biodegradable polymers are preferred in many biomedical applications because such systems are broken down either by hydrolysis or by enzymatic reaction into non-toxic molecules. The rate of degradation is controlled by manipulating the composition of the biodegradable polymer matrix. These types of systems can therefore be employed in certain settings for long-term release of biologically active agents. Biodegradable polymers such as poly(glycolic acid) (PGA), poly-(lactic acid) (PLA), and poly(D,L-lactic-co-glycolic acid) (PLGA), have received considerable attention as possible drug delivery carriers, since the degradation products of these polymers have been found to have low toxicity. During the normal metabolic function of the body these polymers degrade into carbon dioxide and water. These polymers have also exhibited excellent biocompatibility.

For prolonging the biological activity of insulin, analogs and mimetics, and other biologically active agents disclosed herein, as well as optional delivery-enhancing agents, these agents may be incorporated into polymeric matrices, e.g., polyorthoesters, polyanhydrides, or polyesters. This yields sustained activity and release of the active agent(s), e.g., as determined by the degradation of the polymer matrix. Although the encapsulation of biotherapeutic molecules inside synthetic polymers may stabilize them during storage and delivery, the largest obstacle of polymer-based release technology is the activity loss of the therapeutic molecules during the formulation processes that often involve heat, sonication or organic solvents.

Absorption-promoting polymers contemplated for use within this disclosure may include derivatives and chemically or physically modified versions of the foregoing types of polymers, in addition to other naturally occurring or synthetic polymers, gums, resins, and other agents, as well as blends of these materials with each other or other polymers, so long as the alterations, modifications or blending do not adversely affect the desired properties, such as water absorption, hydrogel formation, and/or chemical stability for useful application. In more detailed aspects of this disclosure, polymers such as nylon, acrylan and other normally hydrophobic synthetic polymers may be sufficiently modified by reaction to become water swellable and/or form stable gels in aqueous media.

Absorption-promoting polymers of this disclosure may include polymers from the group of homo- and copolymers based on various combinations of the following vinyl monomers: acrylic and methacrylic acids, acrylamide, methacrylamide, hydroxyethylacrylate or methacrylate, vinylpyrrolidones, as well as polyvinylalcohol and its co- and terpolymers, polyvinylacetate, its co- and terpolymers with the above listed monomers and 2-acrylamido-2-methyl-propanesulfonic acid (AMPS®). Very useful are copolymers of the above listed monomers with copolymerizable functional monomers such as acryl or methacryl amide acrylate or methacrylate esters where the ester groups are derived from straight or branched chain alkyl, aryl having up to four aromatic rings which may contain alkyl substituents of 1 to 6 carbons; steroidal, sulfates, phosphates or cationic monomers such as N,N-dimethylaminoalkyl(meth)acrylamide, dimethylaminoalkyl(meth)acrylate, (meth)acryloxyalkyltrimethylammonium chloride, (meth)acryloxyalkyldimethylbenzyl ammonium chloride.

Additional absorption-promoting polymers within this disclosure are those classified as dextrans, dextrins, and from the class of materials classified as natural gums and resins, or from the class of natural polymers such as processed collagen, chitin, chitosan, pullalan, zooglan, alginates and modified alginates such as "Kelcoloid" (a polypropylene glycol modified alginate) gellan gums such as "Kelocogel," Xanathan gums such as "Keltrol," estastin, alpha hydroxy butyrate and its copolymers, hyaluronic acid and its derivatives, polylactic and glycolic acids.

A very useful class of polymers applicable within the instant disclosure are olefinically-unsaturated carboxylic acids containing at least one activated carbon-to-carbon olefinic double bond, and at least one carboxyl group; that is, an acid or functional group readily converted to an acid containing an olefinic double bond which readily functions in polymerization because of its presence in the monomer molecule, either in the alpha-beta position with respect to a carboxyl group, or as part of a terminal methylene grouping. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule.

Representative acrylates useful as absorption-promoting agents within this disclosure include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate and methacrylate versions thereof. Mixtures of two or three or more long chain acrylic esters may be successfully polymerized with one of the carboxylic monomers. Other comonomers include olefins, including alpha olefins, vinyl ethers, vinyl esters, and mixtures thereof.

Other vinylidene monomers, including the acrylic nitriles, may also be used as absorption-promoting agents within the methods and compositions of this disclosure to enhance delivery and absorption of one or more insulin proteins, analogs and mimetics, and other biologically active agent(s), including to enhance delivery of the active agent(s) to a target tissue or compartment in the subject (e.g., the liver, hepatic portal vein, CNS tissue or fluid, or blood plasma). Useful alpha, beta-olefinically unsaturated nitriles are preferably monoolefinically unsaturated nitriles having from 3 to 10 carbon atoms such as acrylonitrile, methacrylonitrile, and the like. Most preferred are acrylonitrile and methacrylonitrile. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha, beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like.

Yet additional useful absorption promoting materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chloro-styrene; vinyl and allyl ethers and ketones such as vinyl methyl ether and methyl vinyl ketone; chloroacrylates; cyanoalkyl acrylates such as alpha-cyanomethyl acrylate, and the alpha-, beta-, and gamma-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, methylene-bis-acrylamide, allylpentaerythritol, and the like; and bis(beta-haloalkyl)alkenyl phosphonates such as bis(beta-chloroethyl) vinyl phosphonate and the like as are known to those skilled in the art. Copolymers wherein the carboxy containing monomer is a minor constituent, and the other vinylidene monomers present as major components are readily prepared in accordance with the methods disclosed herein.

When hydrogels are employed as absorption promoting agents within this disclosure, these may be composed of synthetic copolymers from the group of acrylic and methacrylic acids, acrylamide, methacrylamide, hydroxyethylacrylate (HEA) or methacrylate (HEMA), and vinylpyrrolidones which are water interactive and swellable. Specific illustrative examples of useful polymers, especially for the delivery of peptides or proteins, are the following types of polymers: (meth)acrylamide and 0.1 to 99 wt. % (meth)acrylic acid; (meth)acrylamides and 0.1-75 wt % (meth)acryloxyethyl trimethyammonium chloride; (meth)acrylamide and 0.1-75 wt % (meth)acrylamide; acrylic acid and 0.1-75 wt % alkyl(meth)acrylates; (meth)acrylamide and 0.1-75 wt % AMPS® (trademark of Lubrizol Corp.); (meth)acrylamide and 0 to 30 wt % alkyl(meth)acrylamides and 0.1-75 wt % AMPS®; (meth)acrylamide and 0.1-99 wt % HEMA; (meth)acrylamide and 0.1 to 75 wt % HEMA and 0.1 to 99% (meth)acrylic acid; (meth)acrylic acid and 0.1-99 wt % HEMA; 50 mole % vinyl ether and 50 mole % maleic anhydride; (meth)acrylamide and 0.1 to 75 wt % (meth)acryloxyalky dimethyl benzylammonium chloride; (meth)acrylamide and 0.1 to 99 wt % vinyl pyrrolidone; (meth)acrylamide and 50 wt % vinyl pyrrolidone and 0.1-99.9 wt % (meth)acrylic acid; (meth)acrylic acid and 0.1 to 75 wt % AMPS® and 0.1-75 wt % alkyl(meth)acrylamide. In the above examples, alkyl means $C_1$ to $C_{30}$, preferably $C_1$ to $C_{22}$, linear and branched and $C_4$ to $C_{16}$ cyclic; where (meth) is used, it means that the monomers with and without the methyl group are included. Other very useful hydrogel polymers are swellable, but insoluble versions of poly(vinyl pyrrolidone) starch, carboxymethyl cellulose and polyvinyl alcohol.

Additional polymeric hydrogel materials within this disclosure include (poly) hydroxyalkyl (meth)acrylate: anionic and cationic hydrogels: poly(electrolyte) complexes; poly (vinyl alcohols) having a low acetate residual: a swellable mixture of crosslinked agar and crosslinked carboxymethyl cellulose: a swellable composition comprising methyl cellulose mixed with a sparingly crosslinked agar; a water swellable copolymer produced by a dispersion of finely divided copolymer of maleic anhydride with styrene, ethylene, propylene, or isobutylene; a water swellable polymer of N-vinyl lactams; swellable sodium salts of carboxymethyl cellulose; and the like.

Other gelable, fluid imbibing and retaining polymers useful for forming the hydrophilic hydrogel for mucosal delivery of biologically active agents include pectin; polysaccharides such as agar, acacia, karaya, tragacenth, algins and guar and their crosslinked versions; acrylic acid polymers, copolymers and salt derivatives, polyacrylamides; water swellable indene maleic anhydride polymers; starch graft copolymers; acrylate type polymers and copolymers with water absorbability of about 2 to 400 times its original weight; diesters of polyglucan; a mixture of crosslinked poly(vinyl alcohol) and poly(N-vinyl-2-pyrrolidone); polyoxybutylene-polyethylene block copolymer gels; carob gum; polyester gels; poly urea gels; polyether gels; polyamide gels; polyimide gels; polypeptide gels; polyamino acid gels; poly cellulosic gels; crosslinked indene-maleic anhydride acrylate polymers; and polysaccharides.

Synthetic hydrogel polymers for use within this disclosure may be made by an infinite combination of several monomers in several ratios. The hydrogel can be crosslinked and generally possesses the ability to imbibe and absorb fluid and swell or expand to an enlarged equilibrium state. The hydrogel typically swells or expands upon delivery to the nasal mucosal surface, absorbing about 2-5, 5-10, 10-50, up to 50-100 or more times fold its weight of water. The optimum degree of swellability for a given hydrogel will be determined for different biologically active agents depending upon such factors as molecular weight, size, solubility and diffusion characteristics of the active agent carried by or entrapped or encapsulated within the polymer, and the specific spacing and cooperative chain motion associated with each individual polymer.

Hydrophilic polymers within this disclosure are water insoluble but water swellable. Such water-swollen polymers as typically referred to as hydrogels or gels. Such gels may be conveniently produced from water-soluble polymer by the process of cross-linking the polymers by a suitable cross-linking agent. However, stable hydrogels may also be formed from specific polymers under defined conditions of pH, temperature and/or ionic concentration, according to know methods in the art. Typically the polymers are cross-linked, that is, cross-linked to the extent that the polymers possess good hydrophilic properties, have improved physical integrity (as compared to non cross-linked polymers of the same or similar type) and exhibit improved ability to retain within the gel network both the biologically active agent of interest and additional compounds for coadministration therewith such as a cytokine or enzyme inhibitor, while retaining the ability to release the active agent(s) at the appropriate location and time.

Generally hydrogel polymers within this disclosure are cross-linked with a difunctional cross-linking in the amount of from 0.01 to 25 weight percent, based on the weight of the monomers forming the copolymer, and more preferably from 0.1 to 20 weight percent and more often from 0.1 to 15 weight percent of the cross-linking agent. Another useful amount of a cross-linking agent is 0.1 to 10 weight percent. Tri, tetra or higher multifunctional cross-linking agents may also be employed. When such reagents are utilized, lower amounts may be required to attain equivalent crosslinking density, i.e., the degree of cross-linking, or network properties that are sufficient to contain effectively the biologically active agent(s).

The cross-links can be covalent, ionic or hydrogen bonds with the polymer possessing the ability to swell in the presence of water containing fluids. Such crosslinkers and cross-linking reactions are known to those skilled in the art and in many cases are dependent upon the polymer system.

Thus a crosslinked network may be formed by free radical copolymerization of unsaturated monomers. Polymeric hydrogels may also be formed by cross-linking preformed polymers by reacting functional groups found on the polymers such as alcohols, acids, amines with such groups as glyoxal, formaldehyde or glutaraldehyde, bis anhydrides and the like.

The polymers also may be cross-linked with any polyene, e.g., decadiene or trivinyl cyclohexane; acrylamides, such as N,N-methylene-bis(acrylamide); polyfunctional acrylates, such as trimethylol propane triacrylate; or polyfunctional vinylidene monomer containing at least 2 terminal $CH_2$<groups, including, for example, divinyl benzene, divinyl naphthlene, allyl acrylates and the like. In certain embodiments, cross-linking monomers for use in preparing the copolymers are polyalkenyl polyethers having more than one alkenyl ether grouping per molecule, which may optionally possess alkenyl groups in which an olefinic double bond is present attached to a terminal methylene grouping (e.g., made by the etherification of a polyhydric alcohol containing at least 2 carbon atoms and at least 2 hydroxyl groups). Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Efficiency of the polyether cross-linking agent increases with the number of potentially polymerizable groups on the molecule. Typically, polyethers containing an average of two or more alkenyl ether groupings per molecule are used. Other cross-linking monomers include for example, diallyl esters, dimethallyl ethers, allyl or methallyl acrylates and acrylamides, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide suitable polymers. When the cross-linking agent is present, the polymeric mixtures usually contain from about 0.01 to about 20 weight percent, e.g., 1%, 5%, or 10% or more by weight of cross-linking monomer based on the total of carboxylic acid monomer, plus other monomers.

In more detailed aspects of this disclosure, mucosal delivery of insulin, analogs and mimetics, and other biologically active agents disclosed herein, is enhanced by retaining the active agent(s) in a slow-release or enzymatically or physiologically protective carrier or vehicle, for example a hydrogel that shields the active agent from the action of the degradative enzymes. In certain embodiments, the active agent is bound by chemical means to the carrier or vehicle, to which may also be admixed or bound additional agents such as enzyme inhibitors, cytokines, etc. The active agent may alternately be immobilized through sufficient physical entrapment within the carrier or vehicle, e.g., a polymer matrix.

Polymers such as hydrogels within this disclosure may incorporate functional linked agents such as glycosides chemically incorporated into the polymer for enhancing intranasal bioavailability of active agents formulated therewith. Examples of such glycosides are glucosides, fructosides, galactosides, arabinosides, mannosides and their alkyl substituted derivatives and natural glycosides such as arbutin, phlorizin, amygdalin, digitonin, saponin, and indican. There are several ways in which a typical glycoside may be bound to a polymer. For example, the hydrogen of the hydroxyl groups of a glycoside or other similar carbohydrate may be replaced by the alkyl group from a hydrogel polymer to form an ether. Also, the hydroxyl groups of the glycosides may be reacted to esterify the carboxyl groups of a polymeric hydrogel to form polymeric esters in situ. Another approach is to employ condensation of acetobromoglucose with cholest-5-en-3beta-ol on a copolymer of maleic acid. N-substituted polyacrylamides can be synthesized by the reaction of activated polymers with omega-aminoalkylglycosides: (1) (carbohydrate-spacer)(n)-polyacrylamide, 'pseudopolysaccharides'; (2) (carbohydrate spacer)(n)-phosphatidylethanolamine(m)-polyacrylamide, neoglycolipids, derivatives of phosphatidylethanolamine; and (3) (carbohydrate-spacer)(n)-biotin(m)-polyacrylamide. These biotinylated derivatives may attach to lectins on the mucosal surface to facilitate absorption of the biologically active agent(s), e.g., a polymer-encapsulated insulin.

Within more detailed aspects of this disclosure, one or more insulin, analogs and mimetics, and/or other biologically active agents, disclosed herein, optionally including secondary active agents such as protease inhibitor(s), cytokine(s), additional modulator(s) of intercellular junctional physiology, etc., are modified and bound to a polymeric carrier or matrix. For example, this may be accomplished by chemically binding a peptide or protein active agent and other optional agent(s) within a crosslinked polymer network. It is also possible to chemically modify the polymer separately with an interactive agent such as a glycosidal containing molecule. In certain aspects, the biologically active agent(s), and optional secondary active agent(s), may be functionalized, i.e., wherein an appropriate reactive group is identified or is chemically added to the active agent(s). Most often an ethylenic polymerizable group is added, and the functionalized active agent is then copolymerized with monomers and a crosslinking agent using a standard polymerization method such as solution polymerization (usually in water), emulsion, suspension or dispersion polymerization. Often, the functionalizing agent is provided with a high enough concentration of functional or polymerizable groups to insure that several sites on the active agent(s) are functionalized. For example, in a polypeptide comprising 16 amine sites, it is generally desired to functionalize at least 2, 4, 5, 7, and up to 8 or more of the sites.

After functionalization, the functionalized active agent(s) is/are mixed with monomers and a crosslinking agent that comprise the reagents from which the polymer of interest is formed. Polymerization is then induced in this medium to create a polymer containing the bound active agent(s). The polymer is then washed with water or other appropriate solvents and otherwise purified to remove trace unreacted impurities and, if necessary, ground or broken up by physical means such as by stirring, forcing it through a mesh, ultrasonication or other suitable means to a desired particle size. The solvent, usually water, is then removed in such a manner as to not denature or otherwise degrade the active agent(s). One desired method is lyophilization (freeze drying) but other methods are available and may be used (e.g., vacuum drying, air drying, spray drying, etc.).

To introduce polymerizable groups in peptides, proteins and other active agents within this disclosure, it is possible to react available amino, hydroxyl, thiol and other reactive groups with electrophiles containing unsaturated groups. For example, unsaturated monomers containing N-hydroxy succinimidyl groups, active carbonates such as p-nitrophenyl carbonate, trichlorophenyl carbonates, tresylate, oxycarbonylimidazoles, epoxide, isocyanates and aldehyde, and unsaturated carboxymethyl azides and unsaturated orthopyridyl-disulfide belong to this category of reagents. Illustrative examples of unsaturated reagents are allyl glycidyl ether, allyl chloride, allylbromide, allyl iodide, acryloyl chloride, allyl isocyanate, allylsulfonyl chloride, maleic anhydride, copolymers of maleic anhydride and allyl ether, and the like.

All of the lysine active derivatives, except aldehyde, can generally react with other amino acids such as imidazole groups of histidine and hydroxyl groups of tyrosine and the thiol groups of cystine if the local environment enhances nucleophilicity of these groups. Aldehyde containing functionalizing reagents are specific to lysine. These types of reactions with available groups from lysines, cysteines, tyrosine have been extensively documented in the literature and are known to those skilled in the art.

In the case of biologically active agents that contain amine groups, it is convenient to react such groups with an acyloyl chloride, such as acryloyl chloride, and introduce the polymerizable acrylic group onto the reacted agent. Then during preparation of the polymer, such as during the crosslinking of the copolymer of acrylamide and acrylic acid, the functionalized active agent, through the acrylic groups, is attached to the polymer and becomes bound thereto.

In additional aspects of this disclosure, biologically active agents, including peptides, proteins, nucleosides, and other molecules which are bioactive in vivo, are conjugation-stabilized by covalently bonding one or more active agent(s) to a polymer incorporating as an integral part thereof both a hydrophilic moiety, e.g., a linear polyalkylene glycol, a lipophilic moiety (see, e.g., U.S. Pat. No. 5,681,811). In one aspect, a biologically active agent is covalently coupled with a polymer comprising (i) a linear polyalkylene glycol moiety, and (ii) a lipophilic moiety, wherein the active agent, linear polyalkylene glycol moiety, and the lipophilic moiety are conformationally arranged in relation to one another such that the active therapeutic agent has an enhanced in vivo resistance to enzymatic degradation (i.e., relative to its stability under similar conditions in an unconjugated form devoid of the polymer coupled thereto). In another aspect, the conjugation-stabilized formulation has a three-dimensional conformation comprising the biologically active agent covalently coupled with a polysorbate complex comprising (i) a linear polyalkylene glycol moiety, and (ii) a lipophilic moiety, wherein the active agent, the linear polyalkylene glycol moiety and the lipophilic moiety are conformationally arranged in relation to one another such that (a) the lipophilic moiety is exteriorly available in the three-dimensional conformation, and (b) the active agent in the composition has an enhanced in vivo resistance to enzymatic degradation.

In a further related aspect, a multiligand conjugated complex is provided which comprises a biologically active agent covalently coupled with a triglyceride backbone moiety through a polyalkylene glycol spacer group bonded at a carbon atom of the triglyceride backbone moiety, and at least one fatty acid moiety covalently attached either directly to a carbon atom of the triglyceride backbone moiety or covalently joined through a polyalkylene glycol spacer moiety (see, e.g., U.S. Pat. No. 5,681,811). In such a multiligand conjugated therapeutic agent complex, the alpha' and beta carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the alpha and alpha' carbons of the triglyceride backbone moiety, with the bioactive therapeutic agent being covalently coupled with the gamma-carbon of the triglyceride backbone moiety, either being directly covalently bonded thereto or indirectly bonded thereto through a polyalkylene spacer moiety. It will be recognized that a wide variety of structural, compositional, and conformational forms are possible for the multiligand conjugated therapeutic agent complex comprising the triglyceride backbone moiety, within the scope of this disclosure. It is further noted that in such a multiligand conjugated therapeutic agent complex, the biologically active agent(s) may advantageously be covalently coupled with the triglyceride modified backbone moiety through alkyl spacer groups, or alternatively other acceptable spacer groups, within the scope of this disclosure. As used in such context, acceptability of the spacer group refers to steric, compositional, and end use application specific acceptability characteristics.

In yet additional aspects of this disclosure, a conjugation-stabilized complex is provided which comprises a polysorbate complex comprising a polysorbate moiety including a triglyceride backbone having covalently coupled to alpha, alpha' and beta carbon atoms thereof functionalizing groups including (i) a fatty acid group; and (ii) a polyethylene glycol group having a biologically active agent or moiety covalently bonded thereto, e.g., bonded to an appropriate functionality of the polyethylene glycol group. Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the biologically active agent or moiety may be covalently bonded.

In yet additional aspects of this disclosure, a stable, aqueously soluble, conjugation-stabilized complex is provided which comprises one or more insulin proteins, analogs and mimetics, and/or other biologically active agent(s) disclosed herein covalently coupled to a physiologically compatible polyethylene glycol (PEG) modified glycolipid moiety. In such complex, the biologically active agent(s) may be covalently coupled to the physiologically compatible PEG modified glycolipid moiety by a labile covalent bond at a free amino acid group of the active agent, wherein the labile covalent bond is scissionable in vivo by biochemical hydrolysis and/or proteolysis. The physiologically compatible PEG modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monoleate, dioleate, triolcate, monostearate, distearate, and tristearate. In such complex, the physiologically compatible PEG modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids.

Storage of Material

In certain aspects of this disclosure, the combinatorial formulations and/or coordinate administration methods herein incorporate an effective amount of peptides and proteins which may adhere to charged glass thereby reducing the effective concentration in the container. Silanized containers, for example, silanized glass containers, are used to store the finished product to reduce adsorption of the polypeptide or protein to a glass container. In other aspects, non-silanized Type 1 glass containers may be used herein.

In yet additional aspects of this disclosure, a kit for treatment of a mammalian subject comprises a stable pharmaceutical composition of one or more insulin compound(s) formulated for mucosal delivery to the mammalian subject wherein the composition is effective to alleviate one or more symptom(s) of obesity, cancer, or malnutrition or wasting related to cancer in said subject without unacceptable adverse side effects. The kit further comprises a pharmaceutical reagent vial to contain the one or more insulin compounds. The pharmaceutical reagent vial is composed of pharmaceutical grade polymer, glass or other suitable material. The pharmaceutical reagent vial is, for example, a silanized glass vial. The kit further comprises an aperture for delivery of the composition to a nasal mucosal surface of the subject. The delivery aperture is composed of a pharmaceutical grade polymer, glass or other suitable material. The delivery aperture is, for example, a silanized glass.

A silanization technique combines a special cleaning technique for the surfaces to be silanized with a silanization process at low pressure. The silane is in the gas phase and at an enhanced temperature of the surfaces to be silanized. The method provides reproducible surfaces with stable, homogeneous and functional silane layers having characteristics of a monolayer. The silanized surfaces prevent binding to the glass of polypeptides or mucosal delivery enhancing agents of the present disclosure.

The procedure is useful to prepare silanized pharmaceutical reagent vials to hold insulin compositions of the present disclosure. Glass trays are cleaned by rinsing with double distilled water (ddH$_2$O) before using. The silane tray is then be rinsed with 95% EtOH, and the acetone tray is rinsed with acetone. Pharmaceutical reagent vials are sonicated in acetone for 10 minutes. After the acetone sonication, reagent vials are washed in ddH$_2$O tray at least twice. Reagent vials are sonicated in 0.1M NaOH for 10 minutes. While the reagent vials are sonicating in NaOH, the silane solution is made under a hood. (Silane solution: 800 mL of 95% ethanol; 96 L of glacial acetic acid; 25 mL of glycidoxypropyltrimethoxy silane). After the NaOH sonication, reagent vials are washed in ddH$_2$O tray at least twice. The reagent vials are sonicated in silane solution for 3 to 5 minutes. The reagent vials are ished in 100% EtOH tray. The reagent vials are dried with prepurified N$_2$ gas and stored in a 100° C. oven for at least 2 hours before using.

Bioadhesive Delivery Vehicles and Methods

In certain aspects of the disclosure, the combinatorial formulations and/or coordinate administration methods herein incorporate an effective amount of a nontoxic bioadhesive as an adjunct compound or carrier to enhance mucosal delivery of one or more biologically active agent(s). Bioadhesive agents in this context exhibit general or specific adhesion to one or more components or surfaces of the targeted mucosa. The bioadhesive maintains a desired concentration gradient of the biologically active agent into or across the mucosa to ensure penetration of even large molecules (e.g., peptides and proteins) into or through the mucosal epithelium. Use of a bioadhesive within the methods and compositions of this disclosure yields from about a two- to about five-fold, often from about a five- to about a ten-fold increase in permeability for peptides and proteins into or through the mucosal epithelium. This enhancement of epithelial permeation often permits effective transmucosal delivery of large macromolecules, for example to the basal portion of the nasal epithelium or into the adjacent extracellular compartments or a blood plasma or CNS tissue or fluid.

This enhanced delivery provides for greatly improved effectiveness of delivery of bioactive peptides, proteins and other macromolecular therapeutic species. These results will depend in part on the hydrophilicity of the compound, whereby greater penetration will be achieved with hydrophilic species compared to water insoluble compounds. In addition to these effects, employment of bioadhesives to enhance drug persistence at the mucosal surface can elicit a reservoir mechanism for protracted drug delivery, whereby compounds not only penetrate across the mucosal tissue but also back-diffuse toward the mucosal surface once the material at the surface is depleted.

A variety of suitable bioadhesives are disclosed in the art for oral administration, U.S. Pat. Nos. 3,972,995; 4,259,314; 4,680,323; 4,740,365; 4,573,996; 4,292,299; 4,715,369; 4,876,092; 4,855,142; 4,250,163; 4,226,848; 4,948,580; and U.S. Pat. Reissue No. 33,093, which find use within the novel methods and compositions of this disclosure. The potential of various bioadhesive polymers as a mucosal, e.g., nasal, delivery platform within the methods and compositions of this disclosure can be readily assessed by determining their ability to retain and release insulin, as well as by their capacity to interact with the mucosal surfaces following incorporation of the active agent therein. In addition, well known methods are applied to determine the biocompatibility of selected polymers with the tissue at the site of mucosal administration. When the target mucosa is covered by mucus (i.e., in the absence of mucolytic or mucus-clearing treatment), it can serve as a connecting link to the underlying mucosal epithelium. Therefore, the term "bioadhesive" as used herein also covers mucoadhesive compounds useful for enhancing mucosal delivery of biologically active agents within this disclosure. However, adhesive contact to mucosal tissue mediated through adhesion to a mucus gel layer may be limited by incomplete or transient attachment between the mucus layer and the underlying tissue, particularly at nasal surfaces where rapid mucus clearance occurs. In this regard, mucin glycoproteins are continuously secreted and, immediately after their release from cells or glands, form a viscoelastic gel. The luminal surface of the adherent gel layer, however, is continuously eroded by mechanical, enzymatic and/or ciliary action. Where such activities are more prominent or where longer adhesion times are desired, the coordinate administration methods and combinatorial formulation methods of this disclosure may further incorporate mucolytic and/or ciliostatic methods or agents as disclosed herein above.

Typically, mucoadhesive polymers for use within the present disclosure are natural or synthetic macromolecules which adhere to wet mucosal tissue surfaces by complex, but non-specific, mechanisms. In addition to these mucoadhesive polymers, this disclosure also describes methods and compositions incorporating bioadhesives that adhere directly to a cell surface, rather than to mucus, by means of specific, including receptor-mediated, interactions. One example of bioadhesives that function in this specific manner is the group of compounds known as lectins. These are glycoproteins with an ability to specifically recognize and bind to sugar molecules, e.g., glycoproteins or glycolipids, which form part of intranasal epithelial cell membranes and can be considered as "lectin receptors."

In certain aspects of this disclosure, bioadhesive materials for enhancing intranasal delivery of biologically active agents comprise a matrix of a hydrophilic, e.g., water soluble or swellable, polymer or a mixture of polymers that can adhere to a wet mucous surface. These adhesives may be formulated as ointments, hydrogels (see above) thin films, and other application forms. Often, these adhesives have the biologically active agent mixed therewith to effectuate slow release or local delivery of the active agent. Some are formulated with additional ingredients to facilitate penetration of the active agent through the nasal mucosa, e.g., into the circulatory system of the individual.

Various polymers, both natural and synthetic ones, show significant binding to mucus and/or mucosal epithelial surfaces under physiological conditions. The strength of this interaction can readily be measured by mechanical peel or shear tests. When applied to a humid mucosal surface, many dry materials will spontaneously adhere, at least slightly. After such an initial contact, some hydrophilic materials start to attract water by adsorption, swelling or capillary forces, and if this water is absorbed from the underlying substrate or from the polymer-tissue interface, the adhesion may be sufficient to achieve the goal of enhancing mucosal absorption of biologically active agents. Such 'adhesion by hydration' can be quite strong, but formulations adapted to employ this mechanism must account for swelling which continues as the dosage transforms into a hydrated mucilage. This is projected for many hydrocolloids useful within this disclosure, especially some cellulose-derivatives, which are generally non-adhesive when applied in pre-hydrated state. Nevertheless, bioadhesive drug delivery systems for mucosal administration are effective within this disclosure when such materials are applied in the form of a dry polymeric powder, microsphere, or film-type delivery form.

Other polymers adhere to mucosal surfaces not only when applied in dry, but also in fully hydrated state, and in the presence of excess amounts of water. The selection of a mucoadhesive thus requires due consideration of the conditions, physiological as well as physico-chemical, under which the contact to the tissue will be formed and maintained. In particular, the amount of water or humidity usually present at the intended site of adhesion, and the prevailing pH, are known to largely affect the mucoadhesive binding strength of different polymers.

Several polymeric bioadhesive drug delivery systems have been fabricated and studied in the past 20 years, not always with success. A variety of such carriers are, however, currently used in clinical applications involving dental, orthopedic, ophthalmological, and surgical uses. For example, acrylic-based hydrogels have been used extensively for bioadhesive devices. Acrylic-based hydrogels are well suited for bioadhesion due to their flexibility and nonabrasive characteristics in the partially swollen state, which reduce damage-causing attrition to the tissues in contact. Furthermore, their high permeability in the swollen state allows unreacted monomer, un-crosslinked polymer chains, and the initiator to be ished out of the matrix after polymerization, which is an important feature for selection of bioadhesive materials within this disclosure. Acrylic-based polymer devices exhibit very high adhesive bond strength. For controlled mucosal delivery of peptide and protein drugs, the methods and compositions of this disclosure optionally include the use of carriers, e.g., polymeric delivery vehicles that function in part to shield the biologically active agent from proteolytic breakdown, while at the same time providing for enhanced penetration of the peptide or protein into or through the nasal mucosa. In this context, bioadhesive polymers have demonstrated considerable potential for enhancing oral drug delivery. As an example, the bioavailability of 9-desglycinamide, 8-arginine vasopressin (DGAVP) intraduodenally administered to rats together with a 1% (w/v) saline dispersion of the mucoadhesive poly(acrylic acid) derivative polycarbophil, is 3-5-fold increased compared to an aqueous solution of the peptide drug without this polymer.

Mucoadhesive polymers of the poly(acrylic acid)-type are potent inhibitors of some intestinal proteases. The mechanism of enzyme inhibition is explained by the strong affinity of this class of polymers for divalent cations, such as calcium or zinc, which are essential cofactors of metalloproteinases, such as trypsin and chymotrypsin. Depriving the proteases of their cofactors by poly(acrylic acid) is reported to induce irreversible structural changes of the enzyme proteins which were accompanied by a loss of enzyme activity. At the same time, other mucoadhesive polymers (e.g., some cellulose derivatives and chitosan) may not inhibit proteolytic enzymes under certain conditions. In contrast to other enzyme inhibitors contemplated within this disclosure (e.g., aprotinin, bestatin), which are relatively small molecules, the trans-nasal absorption of inhibitory polymers is likely to be minimal in light of the size of these molecules, and thereby eliminate possible adverse side effects. Thus, mucoadhesive polymers, particularly of the poly(acrylic acid)-type, may serve both as an absorption-promoting adhesive and enzyme-protective agent to enhance controlled delivery of peptide and protein drugs, especially when safety concerns are considered.

In addition to protecting against enzymatic degradation, bioadhesives and other polymeric or non-polymeric absorption-promoting agents within this disclosure may directly increase mucosal permeability to biologically active agents. To facilitate the transport of large and hydrophilic molecules, such as peptides and proteins, across the nasal epithelial barrier, mucoadhesive polymers and other agents have been postulated to yield enhanced permeation effects beyond what is accounted for by prolonged premucosal residence time of the delivery system. The time course of drug plasma concentrations reportedly suggested that the bioadhesive microspheres caused an acute, but transient increase of insulin permeability across the nasal mucosa. Other mucoadhesive polymers within this disclosure, for example chitosan, reportedly enhance the permeability of certain mucosal epithelia even when they are applied as an aqueous solution or gel. Another mucoadhesive polymer reported to directly affect epithelial permeability is hyaluronic acid and ester derivatives thereof. A particularly useful bioadhesive agent within the coordinate administration, and/or combinatorial formulation methods and compositions of this disclosure is chitosan, as well as its analogs and derivatives. Chitosan is a non-toxic, biocompatible and biodegradable polymer that is widely used for pharmaceutical and medical applications because of its favorable properties of low toxicity and good biocompatibility. It is a natural polyaminosaccharide prepared from chitin by N-deacetylation with alkali. As used within the methods and compositions of this disclosure, chitosan increases the retention (i.e., residence time) of insulin proteins, analogs and mimetics, and other biologically active agents disclosed herein at a mucosal site of application. This mode of administration can also improve patient compliance and acceptance. As further provided herein, the methods and compositions of this disclosure will optionally include a novel chitosan derivative or chemically modified form of chitosan. One such novel derivative within this disclosure is denoted as a β-[1→4]-2-guanidino-2-deoxy-D-glucose polymer (poly-GuD). Chitosan is the N-deacetylated product of chitin, a naturally occurring polymer that has been used extensively to prepare microspheres for oral and intranasal formulations. The chitosan polymer has also been proposed as a soluble carrier for parenteral drug delivery. Within one aspect of this disclosure, o-methylisourea is used to convert a chitosan amine to its guanidinium moiety. The guanidinium compound is prepared, for example, by the reaction between equi-normal solutions of chitosan and o-methylisourea at pH above 8.0.

Additional compounds classified as bioadhesive agents within the present disclosure act by mediating specific interactions, typically classified as "receptor-ligand interactions" between complementary structures of the bioadhesive compound and a component of the mucosal epithelial surface. Many natural examples illustrate this form of specific binding bioadhesion, as exemplified by lectin-sugar interactions. Lectins are (glyco) proteins of non-immune origin which bind to polysaccharides or glycoconjugates.

Several plant lectins have been investigated as possible pharmaceutical absorption-promoting agents. One plant lectin, *Phaseolus vulgaris* hemagglutinin (PHA), exhibits high oral bioavailability of more than 10% after feeding to rats. Tomato (*Lycopersicon esculeutum*) lectin (TL) appears safe for various modes of administration.

In summary, the bioadhesive agents herein disclosed are useful in the combinatorial formulations and coordinate administration methods of the instant disclosure, which optionally incorporate an effective amount and form of a bioadhesive agent to prolong persistence or otherwise increase mucosal absorption of one or more insulin proteins, analogs and mimetics, and other biologically active agents. The bioadhesive agents may be coordinately administered as adjunct compounds or as additives within the combinatorial formulations of this disclosure. In certain embodiments, the bioadhesive agent acts as a 'pharmaceutical glue,' whereas in other embodiments adjunct delivery or combinatorial formulation of the bioadhesive agent serves to intensify contact of the biologically active agent with the nasal mucosa, in some cases by promoting specific receptor-ligand interactions with epithelial cell "receptors," and in others by increasing epithelial permeability to significantly increase the drug concentration gradient measured at a target site (e.g., liver, blood plasma, or CNS tissue or fluid). Yet additional bioadhesive agents within this disclosure act as enzyme (e.g., protease) inhibitors to enhance the stability of mucosally administered biotherapeutic agents delivered coordinately or in a combinatorial formulation with the bioadhesive agent.

Liposomes and Micellar Delivery Vehicles

The coordinate administration methods and combinatorial formulations of the instant disclosure optionally incorporate effective lipid or fatty acid based carriers, processing agents, or delivery vehicles, to provide improved formulations for mucosal delivery of insulin proteins, analogs and mimetics, and other biologically active agents. For example, a variety of formulations and methods are provided for mucosal delivery which comprise one or more of these active agents, such as a peptide or protein, admixed or encapsulated by, or coordinately administered with, a liposome, mixed micellar carrier, or emulsion, to enhance chemical and physical stability and increase the half life of the biologically active agents (e.g., by reducing susceptibility to proteolysis, chemical modification and/or denaturation) upon mucosal delivery.

Within certain aspects of this disclosure, specialized delivery systems for biologically active agents comprise small lipid vesicles known as liposomes. These may be made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within this disclosure is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

A variety of methods are available for preparing liposomes within this disclosure, U.S. Pat. Nos. 4,235,871; 4,501,728; and 4,837,028. For use with liposome delivery, the biologically active agent is typically entrapped within the liposome, or lipid vesicle, or is bound to (i.e., associated with) the outside of the vesicle.

Like liposomes, unsaturated long chain fatty acids, which also have enhancing activity for mucosal absorption, can form closed vesicles with bilayer-like structures (so-called "ufasomes"). These can be formed, for example, using oleic acid to entrap biologically active peptides and proteins for mucosal, e.g., intranasal, delivery within this disclosure.

Other delivery systems within this disclosure combine the use of polymers and liposomes to ally the advantageous properties of both vehicles such as encapsulation inside the natural polymer fibrin. In addition, release of biotherapeutic compounds from this delivery system is controllable through the use of covalent crosslinking and the addition of antifibrinolytic agents to the fibrin polymer.

More simplified delivery systems within this disclosure include the use of cationic lipids as delivery vehicles or carriers, which can be effectively employed to provide an electrostatic interaction between the lipid carrier and such charged biologically active agents as proteins and polyanionic nucleic acids. This allows efficient packaging of the drugs into a form suitable for mucosal administration and/or subsequent delivery to systemic compartments.

Additional delivery vehicles within this disclosure include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of this disclosure, long chain fatty acids, especially fusogenic lipids (unsaturated fatty acids and monoglycerides such as oleic acid, linoleic acid, linoleic acid, monoolein, etc.) provide useful carriers to enhance mucosal delivery of insulin, analogs and mimetics, and other biologically active agents disclosed herein. Medium chain fatty acids (C6 to C12) and monoglycerides have also been shown to have enhancing activity in intestinal drug absorption and can be adapted for use within the mucosal delivery formulations and methods of this disclosure. In addition, sodium salts of medium and long chain fatty acids are effective delivery vehicles and absorption-enhancing agents for mucosal delivery of biologically active agents within this disclosure. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are within this disclosure include, but are not limited to, Na caprylate (C8), Na caprate (C10), Na laurate (C12) or Na oleate (C18), optionally combined with bile salts, such as glycocholate and taurocholate.

Pegylation

Additional methods and compositions provided within this disclosure involve chemical modification of biologically active peptides and proteins by covalent attachment of polymeric materials, for example dextrans, polyvinyl pyrrolidones, glycopeptides, polyethylene glycol and polyamino acids. The resulting conjugated peptides and proteins retain their biological activities and solubility for mucosal administration. In alternate embodiments, insulins, proteins, analogs and mimetics, and other biologically active peptides and proteins, are conjugated to polyalkylene oxide polymers, particularly polyethylene glycols (PEG). U.S. Pat. No. 4,179,337.

Amine-reactive PEG polymers within this disclosure include SC-PEG with molecular masses of 2000, 5000, 10000, 12000, and 20 000; U-PEG-10000; NHS-PEG-3400-biotin; T-PEG-5000; T-PEG-12000; and TPC-PEG-5000. PEGylation of biologically active peptides and proteins may be achieved by modification of carboxyl sites (e.g., aspartic acid or glutamic acid groups in addition to the carboxyl terminus). The utility of PEG-hydrazide in selective modification of carbodiimide-activated protein carboxyl groups under acidic conditions has been described. Alternatively, bifunctional PEG modification of biologically active peptides and proteins can be employed. In some procedures, charged amino acid residues, including lysine, aspartic acid, and glutamic acid, have a marked tendency to be solvent accessible on protein surfaces.

Other Stabilizing Modifications of Active Agents

In addition to PEGylation, biologically active agents such as peptides and proteins within this disclosure can be modified to enhance circulating half-life by shielding the active agent via conjugation to other known protecting or stabilizing compounds, for example by the creation of fusion proteins with an active peptide, protein, analog or mimetic linked to one or more carrier proteins, such as one or more immunoglobulin chains.

Formulation and Administration

Mucosal delivery formulations of the present disclosure comprise insulin, analogs and mimetics, which may be combined together with one or more pharmaceutically acceptable carriers and, optionally, other therapeutic ingredients. The carrier(s) must be "pharmaceutically acceptable" in the sense of being compatible with the other ingredients of the formulation and not eliciting an unacceptable deleterious effect in the subject. Such carriers are described herein or are otherwise well known to those skilled in the art of pharmacology. Desirably, the formulation should not include substances such as enzymes or oxidizing agents with which the biologically active agent to be administered is known to be incompatible. The formulations may be prepared by any of the methods well known in the art of pharmacy.

Within the compositions and methods of this disclosure, the insulin proteins, analogs and mimetics, and other biologically active agents disclosed herein may be administered to subjects by a variety of mucosal administration modes, including by oral, rectal, vaginal, intranasal, intrapulmonary, or transdermal delivery, or by topical delivery to the eyes, ears, skin or other mucosal surfaces. Optionally, insulin proteins, analogs and mimetics, and other biologically active agents disclosed herein can be coordinately or adjunctively administered by non-mucosal routes, including by intramuscular, subcutaneous, intravenous, intra-atrial, intra-articular, intraperitoneal, or parenteral routes. In other alternative embodiments, the biologically active agent(s) can be administered ex vivo by direct exposure to cells, tissues or organs originating from a mammalian subject, for example as a component of an ex vivo tissue or organ treatment formulation that contains the biologically active agent in a suitable, liquid or solid carrier.

Compositions according to the present disclosure are often administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. The formulations may be presented in multi-dose containers, for example in the sealed dispensing system disclosed in U.S. Pat. No. 4,511,069. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present disclosure typically comprise the drug or drug to be delivered, optionally formulated with a surface-active agent, such as a nonionic surfactant (e.g., polysorbate-80), and one or more buffers. In some embodiments of the present invention, the nasal spray solution further comprises a propellant. The pH of the nasal spray solution is optionally from about pH 2.0 to about 8, preferably 4.5±0.5. Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, propyl paraben, butyl paraben, paraben, m-cresol, ortho-cresol, meta-cresol, par-cresol, thiomersal, chlorobutanol, benzylalkonimum chloride, benzethonium chloride, sodium benzoate, sorbic acid, and the like. Pharmaceutical formulations within the context of this disclosure, may include any one preservative or any combination or mixture of more than one preservative. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5μ mass median equivalent aerodynamic diameter (MMEAD), commonly about 1μ MMEAD, and more typically about 2μ MMEAD. Maximum particle size appropriate for deposition within the nasal passages is often about 10μ MMEAD, commonly about 8μ MMEAD, and more typically about 4μ MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI), which rely on the patient's breath, upon pulmonary or nasal inhalation, to disperse the power into an aerosolized amount. Alternatively, the dry powder may be administered via air-assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

To formulate compositions for mucosal delivery within the present disclosure, the biologically active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, acetic acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione) can be included. When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to about 3, more typically about ½ to about 2, and most often about ¾ to about 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g., maleic anhydride) with other monomers (e.g., methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters, etc., can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, e.g., isobutyl 2-cyanoacrylate and dispersed in a biocompatible dispersing medium applied to the nasal mucosa, which yields sustained delivery and biological activity over a protracted time.

To further enhance mucosal delivery of pharmaceutical agents within this disclosure, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compound include polyol compounds, such as oligo-, di- and monosaccarides such as sucrose, mannitol, sorbitol, lactose, L-arabinose, D-erythrose, D-ribose, D-xylose, D-mannose, trehalose, D-galactose, lactulose, cellobiose, gentibiose, glycerin and polyethylene glycol. Other examples of hydrophilic low molecular weight compounds useful as carriers within this disclosure include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

The compositions of this disclosure may alternatively contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. A tabulation of ingredients listed by the above categories can be found in the *U.S. Pharmacopeia National Formulary,* 1990, 1857-1859, which is incorporated by reference. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

Therapeutic compositions for administering the biologically active agent can also be formulated as a solution, microemulsion, or other ordered structure suitable for high concentration of active ingredients. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols such as mannitol, sorbitol, or sodium chloride in the composition. Prolonged absorption of the biologically active agent can be brought about by including in the composition an agent which delays absorption, for example, monostearate salts and gelatin.

In certain embodiments of the instant disclosure, the biologically active agent is administered in a time-release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of this disclosure can be brought about by including in the composition agents that delay absorption, for example, aluminum monosterate hydrogels and gelatin. When controlled release formulations of the biologically active agent is desired, controlled release binders suitable for use in accordance with this disclosure include any biocompatible controlled-release material which is inert to the active agent and which is capable of incorporating the biologically active agent. Numerous such materials are known in the art. Useful controlled-release binders are materials that are metabolized slowly under physiological conditions following their intranasal delivery (e.g., at the nasal mucosal surface, or in the presence of bodily fluids following transmucosal delivery). Appropriate binders include but are not limited to biocompatible polymers and copolymers previously used in the art in sustained release formulations. Such biocompatible compounds are non-toxic and inert to surrounding tissues, and do not trigger significant adverse side effects such as nasal irritation, immune response, inflammation, or the like. They are metabolized into metabolic products that are also biocompatible and easily eliminated from the body.

Exemplary polymeric materials for use in this context include, but are not limited to, polymeric matrices derived from copolymeric and homopolymeric polyesters having hydrolysable ester linkages. A number of these are known in the art to be biodegradable and to lead to degradation products having no or low toxicity. Exemplary polymers include polyglycolic acids (PGA) and polylactic acids (PLA), poly(DL-lactic acid-co-glycolic acid) (DL PLGA), poly(D-lactic acid-coglycolic acid) (D PLGA) and poly(L-lactic acid-co-glycolic acid) (L PLGA). Other useful biodegradable or bioerodable polymers include but are not limited to such polymers as poly(epsilon-caprolactone), poly(epsilon-aprolactone-CO-lactic acid), poly($\epsilon$-aprolactone-CO-glycolic acid), poly(beta-hydroxy butyric acid), poly(alkyl-2-cyanoacrilate), hydrogels such as poly(hydroxyethyl methacrylate), polyamides, poly(amino acids) (i.e., L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof. Many methods for preparing such formulations are generally known to those skilled in the art. Other useful formulations include controlled-release compositions e.g., microcapsules, U.S. Pat. Nos. 4,652,441 and 4,917,893, lactic acid-glycolic acid copolymers useful in making microcapsules and other formulations, U.S. Pat. Nos. 4,677,191 and 4,728,721, and sustained-release compositions for water-soluble peptides, U.S. Pat. No. 4,675,189.

Sterile solutions can be prepared by incorporating the active compound in the required amount in an appropriate solvent with one or a combination of ingredients enumerated herein, as required, followed by filtered sterilization. Dispersions may be prepared by incorporating the active compound into a sterile vehicle that contains a basic dispersion medium and the required other ingredients from those enumerated above. In the case of sterile powders, methods of preparation include vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Mucosal administration according to the present disclosure allows effective self-administration of treatment by patients, provided that sufficient safeguards are in place to control and monitor dosing and side effects. Mucosal administration also overcomes certain drawbacks of other administration forms, such as injections, that are painful and expose the patient to possible infections and may present drug bioavailability problems. For nasal and pulmonary delivery, systems for controlled aerosol dispensing of therapeutic liquids as a spray are well known. In one embodiment, metered doses of active agent are delivered by means of a specially constructed mechanical pump valve, U.S. Pat. No. 4,511,069.

Dosage

For prophylactic and treatment purposes, the biologically active agent(s) disclosed herein may be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). In this context, a therapeutically effective amount (i.e., dosage) of a insulin may include repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by determining effective dosages and administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an alternative embodiment, this disclosure provides compositions and methods for intranasal delivery of insulin, wherein the insulin compound(s) is/are repeatedly administered through an intranasal effective dosage regimen that involves multiple administrations of the insulin to the subject during a daily or weekly schedule to maintain a therapeutically effective elevated and lowered pulsatile level of insulin during an extended dosing period. The compositions and method provide insulin compound(s) that are self-administered by the subject in a nasal formulation between one and six times daily to maintain a therapeutically effective elevated and lowered pulsatile level of insulin during an 8 hour to 24 hour extended dosing period.

Kits

The instant disclosure also includes kits, packages and multicontainer units containing the herein described pharmaceutical compositions, active ingredients, and/or means for administering the same for use in the prevention and treatment of diseases and other conditions in mammalian subjects. Briefly, these kits include a container or formulation that contains one or more insulin proteins, analogs or mimetics, and/or other biologically active agents in combination with mucosal delivery enhancing agents disclosed herein formulated in a pharmaceutical preparation for mucosal delivery.

The intranasal formulations of the present disclosure can be administered using any spray bottle or syringe, or by instillation. An example of a nasal spray bottle is the, "Nasal Spray Pump w/ Safety Clip," Pfeiffer SAP #60548, which delivers a dose of 0.1 mL per squirt and has a diptube length of 36.05 mm. It can be purchased from Pfeiffer of America of Princeton, N.J.

Aerosol Nasal Administration of an Insulin

We have discovered that one or more GRP can be administered intranasally using a nasal spray or aerosol. This is surprising because many proteins and peptides have been shown to be sheared or denatured due to the mechanical forces generated by the actuator in producing the spray or aerosol. In this area the following definitions are useful.

1. Aerosol—A product that is packaged under pressure and contains therapeutically active ingredients that are released upon activation of an appropriate valve system.

2. Metered aerosol—A pressurized dosage form comprised of metered dose valves, which allow for the delivery of a uniform quantity of spray upon each activation.

3. Powder aerosol—A product that is packaged under pressure and contains therapeutically active ingredients in the form of a powder, which are released upon activation of an appropriate valve system.

4. Spray aerosol—An aerosol product that utilizes a compressed gas as the propellant to provide the force necessary to expel the product as a wet spray; it generally applicable to solutions of medicinal agents in aqueous solvents.

5. Spray—A liquid minutely divided as by a jet of air or steam. Nasal spray drug products contain therapeutically active ingredients dissolved or suspended in solutions or mixtures of excipients in nonpressurized dispensers.

6. Metered spray—A non-pressurized dosage form consisting of valves that allow the dispensing of a specified quantity of spray upon each activation.

7. Suspension spray—A liquid preparation containing solid particles dispersed in a liquid vehicle and in the form of course droplets or as finely divided solids.

The fluid dynamic characterization of the aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps.

Definitions

Plume Height—the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study:

Major Axis—the largest chord that can be drawn within the fitted spray pattern that crosses the COMw in base units (mm).

Minor Axis—the smallest chord that can be drawn within the fitted spray pattern that crosses the COMw in base units (mm).

Ellipticity Ratio—the ratio of the major axis to the minor axis, preferably between 1.0 and 1.5, and most preferably between 1.0 and 1.3.

$D_{10}$—the diameter of droplet for which 10% of the total liquid volume of sample consists of droplets of a smaller diameter (μm).

$D_{50}$—the diameter of droplet for which 50% of the total liquid volume of sample consists of droplets of a smaller diameter (μm), also known as the mass median diameter.

$D_{90}$—the diameter of droplet for which 90% of the total liquid volume of sample consists of droplets of a smaller diameter (μm).

Span—measurement of the width of the distribution, the smaller the value, the narrower the distribution. Span is calculated as:

$$\frac{(D_{90} - D_{10})}{D_{50}}.$$

% RSD—percent relative standard deviation, the standard deviation divided by the mean of the series and multiplied by 100, also known as % CV.

Volume—the volume of liquid or powder discharged from the delivery device with each actuation, preferably between 0.01 mL and about 2.5 mL and most preferably between 0.02 mL and 0.25 mL.

EXAMPLES

The above disclosure generally describes the present invention, which is further exemplified by the following examples. These examples are described solely for purposes of illustration, and are not intended to limit the scope of the invention. Although specific terms and values have been employed herein, such terms and values will likewise be understood as exemplary and non-limiting to the scope of the invention.

Example 1

Intranasally Administered Insulin Pharmacokinetic Results in Rabbits

Pharmacokinetic (PK; e.g., insulin measurement) values were measured for insulin treated New Zealand White Rabbits at specified time-points up to 240 minutes following administration. All data calculations are dose normalized and the pharmacokinetic data was baseline corrected.

Intranasal peptide delivery formulations, "PDF" (shown in Table 1), were compared with a SC NovoLog rapid-acting formulation (NovoLog diluent consists of: 16 mg/mL glycerin, 1.5 mg/mL phenol, 1.72 mg/mL m-cresol, 19.6 mg/mL zinc, 1.25 mg/mL disodium hydrogen phosphate dihydrate, and 0.58 mg/mL NaCl, pH 7.2-7.6). "PDF" as used herein is a formulation consisting of 45 mg/mL Me-β-CD, 1 mg/mL DDPC, 1 mg/mL EDTA, 10 mM arginine pH 7.0 with NaCl added to achieve about 220 mOsm/kg, and with or without preservative. 2×PDF is a formulation consisting of 90 mg/mL Me-β-CD, 2 mg/mL DDPC, 2 mg/mL EDTA (other components remain same as in PDF). As used herein, -DDPC is a PDF without DDPC; Polysorbate 80 (Tween) was added to various PDF at 1%, 2%, 5% (10, 20, or 50 mg/mL) as indicated.

TABLE 1

PDF Components and Dosage in Rabbits

| Formulation (Group) | Insulin Dose (IU/kg) | Me-β-CD (mg/mL) | DDPC (mg/mL) | EDTA (mg/mL) | Tween 80 (mg/mL) | Arg Buffer (mM) | NaCl (mg/mL) | pH |
|---|---|---|---|---|---|---|---|---|
| IN/1X PDF 1% Tween | 6 | 45 | 1 | 1 | 10 | 10 | 4 | 7 |
| IN/1X PDF-DDPC | 6 | 45 | 0 | 1 | 10 | 10 | 4 | 7 |
| IN/1X PDF 2% Tween | 6 | 45 | 1 | 1 | 20 | 10 | 4 | 7 |
| IN/1X PDF 5% Tween | 6 | 45 | 1 | 1 | 50 | 10 | 4 | 7 |
| IN/2X PDF 1% Tween | 6 | 90 | 2 | 2 | 10 | 10 | 4 | 7 |
| IN 2X PDF 2% Tween | 6 | 90 | 2 | 2 | 20 | 10 | 4 | 7 |
| SC-PDF | 0.6 | 45 | 1 | 1 | 10 | 10 | 4 | 7 |
| SC-NovoLog | 0.6 IU/kg (3 U/mL) NovoLog in NovoLog Dilutent | | | | | | | 7.4 |

Shown in Table 2 are the $T_{max}$, % $C_{max}$, $AUC_{last}$, $AUC_{inf}$, and % bioavailability relative to SC-NovoLog results (with pharmacokinetic baseline subtracted); and results for the IN/1×PDF 1% Tween and SC-Regular formulations. The pharmacokinetic curves of these formulations are similar, showing that IN/1×PDF results in a unique pharmacokinetic profile for IN insulin.

TABLE 2

Pharmacokinetic Results after Intranasal Administration of Insulin PDF in Rabbits

| Formulation | $T_{max}$ (min) | % $C_{max}$ (μIU/mL) | $AUC_{last}$ (min*μIU/mL) | $AUC_{inf}$ (min*μIU/mL) | % BA (insulin) |
|---|---|---|---|---|---|
| IN/1X PDF 1% Tween | 30 | 73.84 | 1766.20 | 3445.22 | 2.2 |
| IN/1X PDF 1% Tween* | 18 | 81.00 | 2397.00 | 4192.93 | 2.9 |
| IN/1X PDF-DDPC | 19 | 56.32 | 1549.00 | 2868.44 | 1.9 |
| IN/1X PDF 2% Tween | 27 | 97.65 | 4106.48 | 2436.22 | 5.0 |
| IN/1X PDF 5% Tween | 24 | 65.30 | 1412.40 | 2253.16 | 1.7 |
| IN/2X PDF 1% Tween | 15 | 79.24 | 2744.00 | 4173.69 | 3.4 |
| IN 2X PDF 2% Tween | 22.5 | 73.28 | 2283.34 | 7819.15 | 2.8 |
| SC-Regular* | 30 | 128.38 | 7750.15 | 8982.12 | 95.0 |
| SC-PDF | 29 | 141.60 | 5830.50 | 8821.04 | 71.4 |
| SC NovoLog | 23 | 168.84 | 8160.70 | 12338.64 | |

*Results from separate data set

The results in Table 2 show that the IN/1×PDF 2% Tween had the highest % bioavailability, $C_{max}$, and $AUC_{last}$ of the intranasal formulations tested. The % bioavailability, $C_{max}$ and $AUC_{last}$ were decreased when DDPC was removed. Regular, SC-NovoLog, and SC-PDF insulin resulted in similar bioavailability. For the % bioavailability, intranasal formulations resulted in approximately 2-5% bioavailability. IN/1×PDF 2% Tween showed the highest bioavailability at 5%.

Table 3 shows another group of PDF dosed in rabbits. Some of the formulations in Table 3 contained a combination of preservatives: 10 mg/mL propylene glycol, 0.33 mg/mL methylparaben, and 0.17 mg/mL propylparaben. The formulations labeled "-Pre" are the PDF formulations without a preservative. Two SC groups were dosed, one with regular insulin in absence of enhancers, and one with regular insulin in presence of PDF.

TABLE 3

PDF Dosage in Rabbits

| Formulation | Regular Insulin Dose (IU/kg) |
|---|---|
| 1XPDF 1% Tween | 6 |
| 1XPDF 1% Tween (-DDPC) | 6 |
| 1XPDF 2% Tween | 6 |
| 1XPDF 2% Tween (-DDPC) | 6 |
| 1XPDF 1% Tween (-Pre) | 6 |
| 1XPDF 1% Tween (-PreDDPC) | 6 |
| SC-Regular PDF | 0.6 |
| SC-Regular Saline | 0.6 |

The pharmacokinetic data for the groups shown in Table 3 are shown in Table 4, Table 5 and Table 6. Within the % CV for the various pharmacokinetic parameters the pharmacokinetic data are similar for the various groups, with a bioavailability relative to SC regular insulin control about 2-6% and $T_{max}$ in the range of 12-36 minutes.

TABLE 4

PK Results after Intranasal Administration of Insulin PDF (Table 3) in Rabbits

| Formulation | Group # | Tmax (min) | Cmax (uIU/mL) | AUClast (min*uIU/mL) |
|---|---|---|---|---|
| 1XPDF 1% Tween | 1 | 29.0 | 108.4 | 2504.2 |
| 1XPDF 1% Tween (−DDPC) | 2 | 16.3 | 95.7 | 2284.8 |
| 1XPDF 2% Tween | 3 | 36.3 | 88.1 | 2122.7 |
| 1XPDF 2% Tween (−DDPC) | 4 | 12.0 | 138.5 | 3387.4 |
| 1XPDF 1% Tween (−Pre) | 5 | 29.0 | 79.0 | 1174.5 |
| 1XPDF 1% Tween (−PreDDPC) | 6 | 13.0 | 94.7 | 2453.3 |
| SC Regular PDF | 7 | 19.0 | 129.7 | 5014.3 |
| SC Regular Saline | 8 | 17.0 | 144.2 | 5885.5 |

TABLE 5

Bioavailability Results after Intranasal Administration of Insulin PDF (Table 3) in Rabbits

| Formulation | Group # | Bioavailability |
|---|---|---|
| 1XPDF 1% Tween | 1 | 4.3 |
| 1XPDF 1% Tween (−DDPC) | 2 | 3.9 |
| 1XPDF 2% Tween | 3 | 3.6 |
| 1XPDF 2% Tween (−DDPC) | 4 | 5.8 |
| 1XPDF 1% Tween (−Pre) | 5 | 2.0 |
| 1XPDF 1% Tween (−PreDDPC) | 6 | 4.2 |
| SC Regular PDF | 7 | 85.2 |
| SC Regular Saline | 8 | NA |

TABLE 6

% CV Results after Intranasal Administration of Insulin PDF (Table 3) in Rabbits

| Formulation | Group # | Tmax (min) | Cmax (uIU/mL) | AUClast (min*uIU/mL) |
|---|---|---|---|---|
| 1XPDF 1% Tween | 1 | 56.4 | 84.2 | 84.7 |
| 1XPDF 1% Tween (−DDPC) | 2 | 58.2 | 90.8 | 124.5 |
| 1XPDF 2% Tween | 3 | 75.9 | 81.4 | 105.9 |
| 1XPDF 2% Tween (−DDPC) | 4 | 22.8 | 87.9 | 105.2 |
| 1XPDF 1% Tween (−Pre) | 5 | 97.8 | 54.4 | 95.8 |
| 1XPDF 1% Tween (−PreDDPC) | 6 | 34.4 | 68.2 | 72.7 |
| SC Regular PDF | 7 | 57.1 | 58.3 | 64.2 |
| SC Regular Saline | 8 | 73.8 | 28.7 | 62.5 |

Pharmarmacodynamic (PD; e.g., glucose measurements) were measured for insulin treated New Zealand White Rabbits at specified time-points up to 240 minutes following administration of the formulations shown in Table 3. Glucose was measured at every time-point in duplicate with a Glucometer (One-Touch Ultra). The pharmacodynamic data, change in glucose, are shown in Table 7.

TABLE 7

PD Results after Intranasal Administration of Insulin PDF (Table 3) in Rabbits

| Formulation | Dose (IU/kg) | Tmin | % Cmin |
|---|---|---|---|
| 1XPDF 1% Tween | 6 | 30 | 49.8 |
| 1XPDF 1% Tween (−DDPC) | 6 | 30 | 54.6 |
| 1XPDF 2% Tween | 6 | 30 | 49.5 |
| 1XPDF 2% Tween (−DDPC) | 6 | 30 | 48.4 |
| 1XPDF 1% Tween (−Pre) | 6 | 30 | 55.6 |
| 1XPDF 1% Tween (−PreDDPC) | 6 | 30 | 57.3 |
| SC-Regular PDF | 0.6 | 45 | 36.4 |
| SC-Regular Saline | 0.6 | 60 | 38.4 |

The data in Table 7 shows that the time to onset of glucose fall (as indicated by $T_{min}$) is faster for regular insulin in the intranasal PDF (45 min for SC; 30 min for intranasal) compared to the control formulation (60 min for SC). All intranasal groups demonstrated about the same pharmacodynamic effect ($T_{min}$ and % $C_{min}$). Presence or absence of DDPC in the formulation did not affect the pharmacodynamic results. As used herein, $C_{min}$ means a pharmacodynamic measurement representing the minimum concentration of glucose (i.e., a glucose trough) occurring at time $T_{min}$, following the administration of insulin.

Table 8 describes intranasal, oral, and SC regular insulin formulations. TDM is a PDF further consisting of 2.5 mg/mL tetradecylmaltoside. Polysorbate 80 (Tween) was added to various formulations at 1% (10 mg/mL) as indicated. Propylene glycol (PG) was added to various formulations at 1% or 2.5% (10 or 25 mg/ml). The effect of gelatin at 0.2% was tested. Three oral groups were dosed, one with regular insulin in absence of enhancers (#8), one with regular insulin in presence of PDF (#9), and one with regular insulin in presence of PDF without DDPC (#7). An SC regular insulin group was dosed for comparison.

TABLE 8

Description of IN, Oral and SC Groups Dosed

| Group # | Formulation | Route | Dose Level (IU/kg) |
|---|---|---|---|
| 1 | IXPDF 1% Tween (−PG) | IN | 6 |
| 2 | 1XPDF 1% Tween (2.5% PG) | IN | 6 |
| 3 | TDM hypotonic | IN | 6 |
| 4 | TDM Isotonic | IN | 6 |
| 5 | 1XPDF 1% Tween (1% PG) | IN | 6 |
| 6 | 1XPDF 1% Tween (0.2% Gelatin) | IN | 6 |
| 7 | 1XPDF Oral (−DDPC + PG) | Oral | 6 |
| 8 | 1XPDF Oral (−DDPC − PG − Tween) | Oral | 6 |
| 9 | 1XPDF Oral (+DDPC + PG) | Oral | 6 |
| 10 | SC Regular Insulin | SC | 0.6 |

The pharmacokinetic data in rabbits for the groups shown in Table 8 are presented in Tables 9, Table 10 and Table 11.

TABLE 9

PK Parameters for IN, Oral and SC Groups (Table 8)

| Formulation | Tmax (min) | Cmax (μIU/mL) | AUClast (min *μIU/mL) | AUCinf (min*μIU/mL) |
|---|---|---|---|---|
| 1XPDF 1% Tween (−PG) | 59 | 125.06 | 5001.45 | 2565.5917 |
| 1XPDF 1% Tween (2.5% PG) | 18 | 95.2 | 3178 | 5192.0496 |

TABLE 9-continued

PK Parameters for IN, Oral and SC Groups (Table 8)

| Formulation | Tmax (min) | Cmax (μIU/mL) | AUClast (min *μIU/mL) | AUCinf (min*μIU/mL) |
|---|---|---|---|---|
| TDM hypotonic | 33 | 206.58 | 3971 | 9828.6486 |
| TDM Isotonic | 23 | 179.52 | 5663 | 9788.9524 |
| 1XPDF 1% Tween (1% PG) | 34 | 108 | 6218 | 62759.0604 |
| 1XPDF 1% Tween (0.2% Gelatin) | 13 | 373.6 | 8755.5 | 9067.4665 |
| 1XPDFOral (−DDPC + PG) | 5 | 24.56 | 111.9 | N/A |
| 1XPDFOral (−DDPC − PG − Tween) | 5 | 6.6 | 16.5 | N/A |
| 1XPDFOral (+DDPC + PG) | 5 | 3.08 | 64 | 408.0042 |
| SC Regular Insulin | 17 | 144.2 | 5885.5 | 3358.285 |

TABLE 10

PK Data (bioavailability) for IN, Oral and SC Groups (Table 8)

| Formulation | AUClast (min *uIU/mL) | bioavailability (insulin) |
|---|---|---|
| 1XPDF 1% Tween (−PG) | 5001.45 | 8.5 |
| 1XPDF 1% Tween (2.5% PG) | 3178 | 5.4 |
| TDM hypotonic | 3971 | 6.7 |
| TDM Isotonic | 5663 | 9.6 |
| 1XPDF 1% Tween (1% PG) | 6218 | 10.6 |
| 1XPDF 1% Tween (0.2% Gelatin) | 8755.5 | 14.9 |
| 1XPDFOral (−DDPC + PG) | 111.9 | 0.2 |
| 1XPDFOral (−DDPC − PG − Tween) | 16.5 | 0.0 |
| 1XPDFOral (+DDPC+ PG) | 64 | 0.1 |
| SC Regular Insulin | 5885.5 | N/A |

TABLE 11

% CV for IN, Oral and SC Groups (Table 8)

| Formulation | Tmax (min) | Cmax (uIU/mL) | AUClast (min *uIU/mL) |
|---|---|---|---|
| 1XPDF 1% Tween (−PG) | 67.4 | 59.9 | 111.1 |
| 1XPDF 1% Tween (2.5% PG) | 87.0 | 75.4 | 77.1 |
| TDM hypotonic | 59.3 | 41.3 | 56.6 |
| TDM Isotonic | 42.4 | 73.4 | 91.4 |
| 1XPDF 1% Tween (1% PG) | 142.0 | 51.7 | 95.9 |
| 1XPDF 1% Tween (0.2% Gelatin) | 34.4 | 21.3 | 35.3 |
| 1XPDFOral (−DDPC + PG) | 0.0 | 164.5 | 190.0 |
| 1XPDFOral (−DDPC − PG − Tween) | 0.0 | 199.2 | 199.2 |
| 1XPDFOral (+DDPC + PG) | 0.0 | 116.6 | 178.3 |
| SC Regular Insulin | 73.8 | 28.7 | 62.5 |

For the intranasal groups containing PDF with or without PG (and no gelatin), as well as for the groups containing TDM, the pharmacokinetic data were similar, with a bioavailability compared to SC regular insulin at about 5.4-10.6% and $T_{max}$ in the range of from about 18 to about 59 minutes. In the case of 1xPDF with 1% Tween in the presence of 0.2% gelatin, bioavailability increased to about 14.9%. % CV for $C_{max}$ and AUC were between 50-111% for the intranasal groups in Table 8 containing PDF with or without PG (and no gelatin), as well as the groups containing TDM. In contrast, for 1xPDF with 1% Tween in the presence of 0.2% gelatin, there was a decrease in % CV for $C_{max}$ and AUC to 21.3% and 35.3%, respectively. It was noted that the % CV for $C_{max}$ and AUC of the 1xPDF with 1% Tween in the presence of 0.2% gelatin formulation were lower than those observed for the SC injection.

Pharmacodynamic data was similar between all intranasal formulations, but SC dosing had an extended pharmacodynamic effect compared to intranasal. No pharmacodynamic effect was observed for the oral dose groups.

The pharmacokinetic and pharmacodynamic data show that regular insulin administered in intranasal PDF is consistent with an ultra-rapid acting insulin profile. It is surprising that an intranasal administration of the pharmaceutical formulations disclosed herein provides a more rapid acting insulin profile than previously attained, for example, following SC administration of a selectively designed insulin analogue or derivative. These data show that the onset (maximum drop in glucose concentration as indicated by $T_{min}$) is faster for intranasally administered regular insulin in the PDF compared to SC formulations. The addition of gelatin, a thickening agent, enhanced the pharmacodynamic and pharmacokinetic (14.9% bioavailability relative to SC control) effect for intranasally administered insulin in PDF.

Example 2

PK and PD Results for Intranasal Administration of Insulin Formulations Containing Thickening Agents in Rabbits Pharmacokinetic and pharmacodynamic data were evaluated for rabbits dosed with intranasal insulin formulations containing different thickening agents. Abbreviations include the following: Me-β-CD=methyl-beta-cyclodextrin, EDTA=disodium edetate, Tween or TW=polysorbate 80, HPMC=hydroxypropyl methylcellulose (100 cps), MC=methylcellulose (15 cps), CMC=carboxymethylcellulose sodium (low viscosity), MP=methylparaben sodium, PP=propylparaben sodium, PG=propylene glycol, NaCl=sodium chloride. Small amounts of 2N HCl or NaOH were added to the formulation when necessary to achieve the desired pH. The regular insulin used in the study was at a concentration of approximately 28 IU/mg. Table 12 shows the intranasal formulations used in this Example.

TABLE 12

Intranasal Insulin Formulations Containing a Thickening Agent

| # | Regular Insulin (IU/mL) | Me-β-CD (mg/mL) | EDTA (mg/mL) | Tween 80 (mg/mL) | Arginine Buffer (mM) | Thickening Agent (mg/mL) | MP (mg/mL) | PP (mg/mL) | PG (mg/mL) | NaCl (mg/mL) | pH |
|---|---|---|---|---|---|---|---|---|---|---|---|
| 1 | 400 | 45 | 1 | 10 | 10 | 0 | 0.33 | 0.17 | 10 | 0 | 7.3 |
| 2 | 400 | 45 | 1 | 10 | 10 | Gelatin (2 mg/mL) | 0.33 | 0.17 | 10 | 0 | 7.3 |
| 3 | 400 | 45 | 1 | 10 | 10 | Gelatin (4 mg/mL) | 0.33 | 0.17 | 10 | 0 | 7.3 |
| 4 | 400 | 45 | 1 | 10 | 10 | HPMC (2.5 mg/mL) | 0.33 | 0.17 | 10 | 0 | 7.3 |
| 5 | 400 | 45 | 1 | 10 | 10 | MC (2.5 mg/mL) | 0.33 | 0.17 | 10 | 0 | 7.3 |
| 6 | 400 | 45 | 1 | 10 | 10 | Carbopol 974 P (2.5 mg/mL) | 0.33 | 0.17 | 10 | 0 | 7.3 |
| 7 | 400 | 45 | 1 | 10 | 10 | CMC (1 mg/mL) | 0.33 | 0.17 | 10 | 0 | 7.3 |
| 8 | 400 | 45 | 1 | 10 | 10 | Gelatin (2 mg/mL) | 0.33 | 0.17 | 10 | 3 | 7.3 |

In this example, 15 mL of each formulation was manufactured and stored in clear non-silanized glass vials at 2-8° C. All formulations were dosed at 6.0 IU/kg. Table 13 describes the dosages for used for the Table 12 formulations.

TABLE 13

Thickening Agent Dosage Groups

| Group # | Formulation | Dose IU/kg |
|---|---|---|
| 1 | 1XPDF 1% Tween | 6.0 |
| 2 | 1XPDF 1% Tween (0.2% Gelatin) | 6.0 |
| 3 | 1XPDF 1% Tween (0.4% Gelatin) | 6.0 |
| 4 | 1XPDF 1% Tween (0.25% HPMC) | 6.0 |
| 5 | 1XPDF 1% Tween (0.25% MC) | 6.0 |
| 6 | 1XPDF 1% Tween (0.25% Carbopol) | 6.0 |
| 7 | 1XPDF 1% Tween (0.1% CMC) | 6.0 |
| 8 | 1XPDF 1% TW (0.2% Gelatin) | 6.0 |

Figure 2:
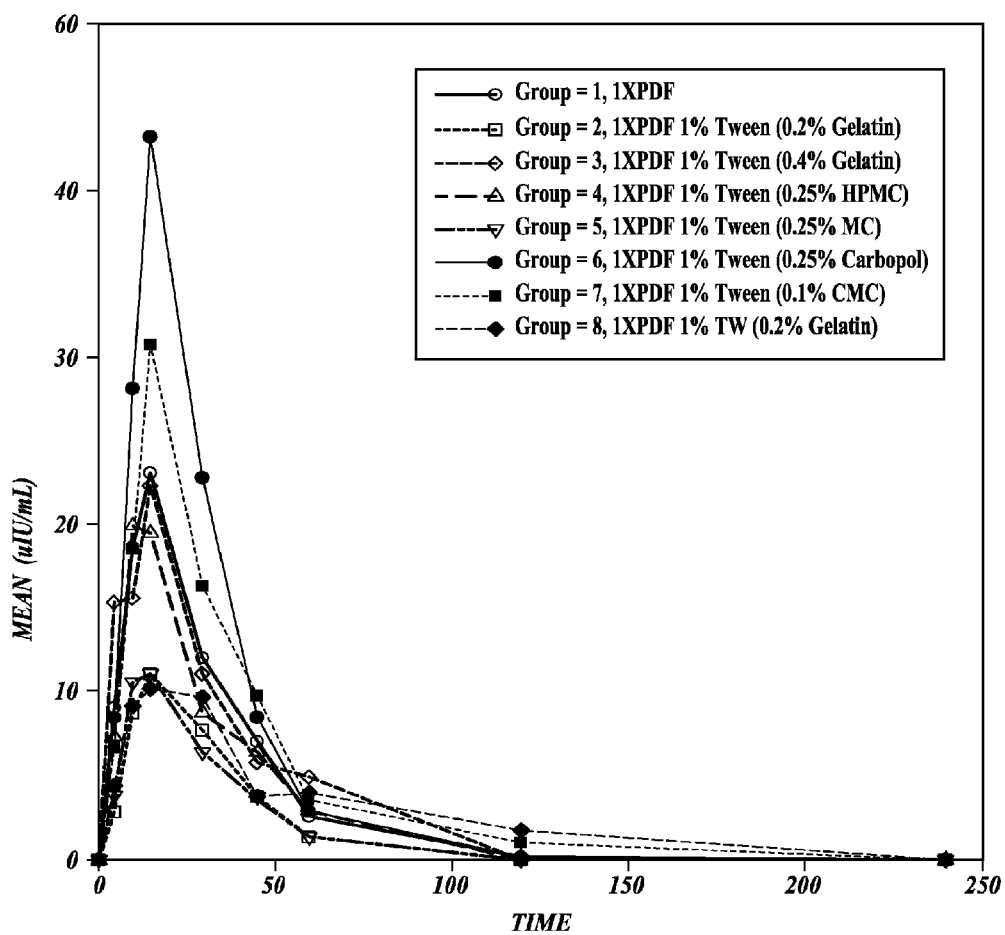
FIG. 2: Pharmacokinetic data, mean insulin levels, for groups dosed in rabbits with formulations containing a thickening agent.

The pharmacokinetic results for the mean concentration of insulin (μIU/mL) over time is shown in FIG. 2. FIG. 2 shows that $C_{max}$ was greatest for Group 6, 1×PDF 1% Tween (25% Carbopol), compared to the other formulations. Peak serum insulin levels for the 8 Groups occurred within 13-37 minutes. The pharmacokinetic parameters are summarized in Table 14.

TABLE 14

PK Parameter Results after Administration of Insulin in Formulations Containing a Thickening Agent (Table 12) in Rabbits

| Group # | Formulation | Tmax (min) | Cmax (μIU/mL) | AUClast (min*μIU/mL) | AUCinf (min*μIU/mL) |
|---|---|---|---|---|---|
| 1 | 1XPDF 1% Tween | 13.00 | 243.68 | 7409.6 | 7546.2311 |
| 2 | 1XPDF 1% Tween (0.2% Gelatin) | 18.00 | 119.28 | 3487.6 | 3756.8904 |
| 3 | 1XPDF 1% Tween (0.4% Gelatin) | 22.00 | 280.64 | 6617.8 | 10094.2851 |
| 4 | 1XPDF 1% Tween (0.25% HPMC) | 37.00 | 212.74 | 6570.05 | 8149.3682 |
| 5 | 1XPDF 1% Tween (0.25% MC) | 14.00 | 114.16 | 3383.2 | 4536.5694 |
| 6 | 1XPDF 1% Tween (0.25% Carbopol) | 15.00 | 460.48 | 11583.6 | 12107.2492 |
| 7 | 1XPDF 1% Tween (0.1% CMC) | 24.00 | 320.2 | 10482.5 | 11361.0313 |
| 8 | 1XPDF 1% TW (0.2% Gelatin) | 29.00 | 231.48 | 6497.95 | 12461.998 |

The % CV results are shown in Table 15.

TABLE 15

% CV Results after Administration of Insulin in Formulations Containing a Thickening Agent (Table 12) in Rabbits

| Group # | Formulation | Tmax | Cmax | AUClast |
|---|---|---|---|---|
| 1 | 1XPDF 1% Tween | 21.1 | 68.4 | 73.2 |
| 2 | 1XPDF 1% Tween (0.2% Gelatin) | 37.3 | 27.5 | 48.1 |
| 3 | 1XPDF 1% Tween (0.4% Gelatin) | 98.5 | 79.3 | 69.1 |
| 4 | 1XPDF 1% Tween (0.25% HPMC) | 127.3 | 74.7 | 84.0 |
| 5 | 1XPDF 1% Tween (0.25% MC) | 16.0 | 48.2 | 60.7 |
| 6 | 1XPDF 1% Tween (0.25% Carbopol) | 0.0 | 62.0 | 47.6 |
| 7 | 1XPDF 1% Tween (0.1% CMC) | 55.9 | 76.4 | 60.0 |
| 8 | 1XPDF 1% TW (0.2% Gelatin) | 76.5 | 95.0 | 76.1 |

The bioavailability results are shown in Table 16.

TABLE 16

Bioavailability (insulin) Results after Administration of Insulin in Formulations Containing a Thickening Agent (Table 12) in Rabbits

| Group # | Formulation | Dose IU/kg | AUClast (min*uIU/mL) | % F |
|---|---|---|---|---|
| 1 | 1XPDF 1% Tween | 6.0 | 7409.6 | 12.6 |
| 2 | 1XPDF 1% Tween (0.2% Gelatin) | 6.0 | 3487.6 | 5.9 |
| 3 | 1XPDF 1% Tween (0.4% Gelatin) | 6.0 | 6617.8 | 11.2 |
| 4 | 1XPDF 1% Tween (0.25% HPMC) | 6.0 | 6570.05 | 11.2 |
| 5 | 1XPDF 1% Tween (0.25% MC) | 6.0 | 3383.2 | 5.7 |
| 6 | 1XPDF 1% Tween (0.25% Carbopol) | 6.0 | 11583.6 | 19.7 |
| 7 | 1XPDF 1% Tween (0.1% CMC) | 6.0 | 10482.5 | 17.8 |
| 8 | 1XPDF 1% TW (0.2% Gelatin) | 6.0 | 6497.95 | 11.0 |
|  | SC Regular Insulin | 0.6 | 5885.5 |  |

Figure 3:
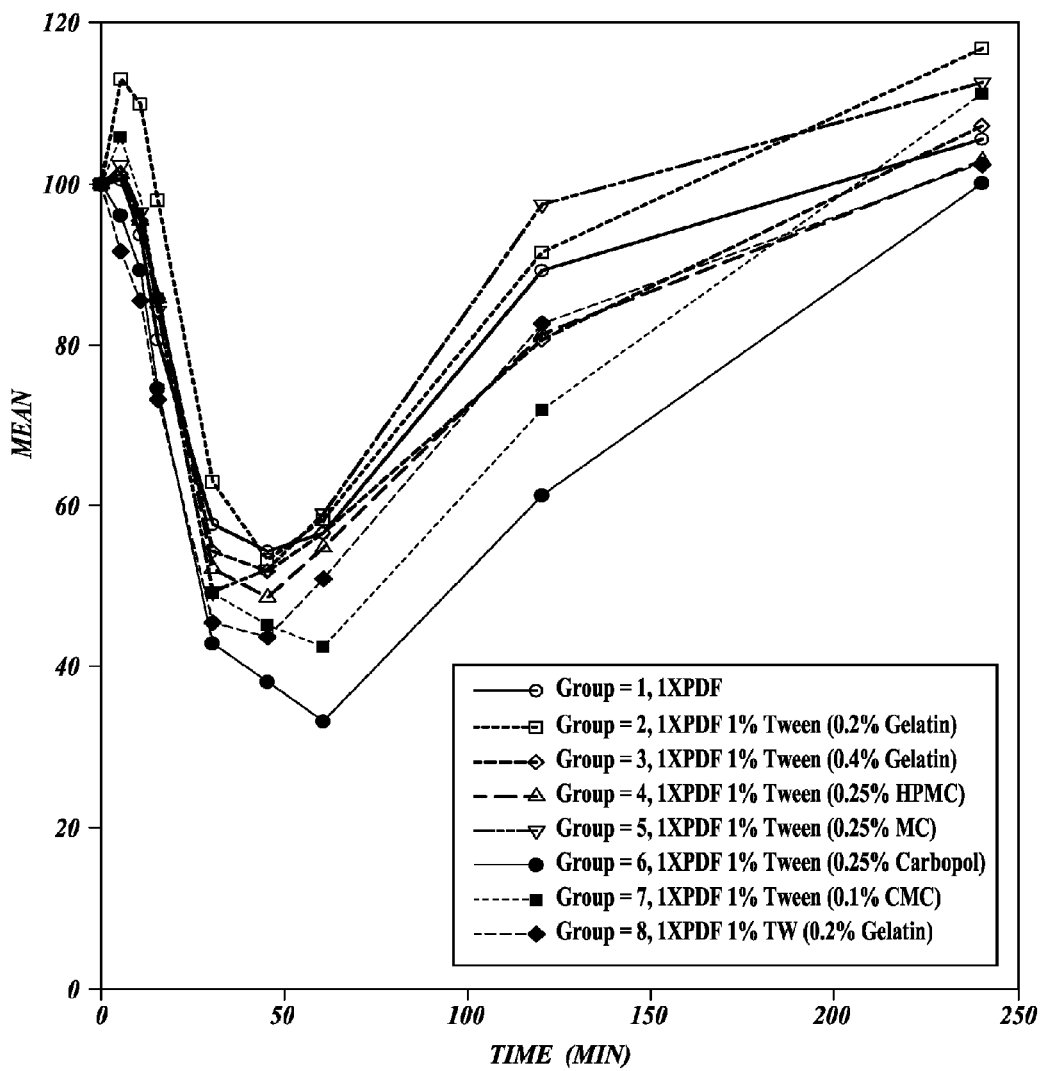
FIG. 3: Pharmacodynamic data, mean % glucose from initial, for groups dosed in rabbits with formulations containing a thickening agent.

The pharmacodynamic results are shown in FIG. 3. Glucose was measured at regular time-points with a Glucometer (One-Touch Ultra). FIG. 3 shows the mean change in % glucose over time for the eight groups tested. Group 6, a formulation consisting of 1×PDF 1% Tween (0.25% Carbopol), showed the greatest reduction in % glucose from initial compared to all other groups. Glucose troughs for the 8 Groups occurred within 60 minutes. Group 8 (which contained a tonicity adjusting agent, NaCl) had the greatest reduction in % glucose from initial compared to the other gelatin formulations. The formulations containing Carbopol and CMC had the greatest reduction in % glucose from initial compared to the other non-gelatin formulations.

The pharmacokinetic and pharmacodynamic results in rabbits show that the intranasal insulin formulations tested had ultra-rapid acting insulin profiles, with peak serum insulin levels in less than 60 minutes and glucose troughs in less than 90 minutes. Bioavailability was increased when thickening agents were added to PDF intranasal insulin formulations. Isotonic formulations containing gelatin showed an increase in bioavailability. The formulation containing gelatin showed improved performance with isotonic conditions (Group #8; 0.2% Gelatin including NaCl) compared to hypotonic conditions (Group #2; 0.2% Gelatin without NaCl). The formulations containing Carbopol and CMC showed the greatest increase in pharmacokinetic and pharmacodynamic results for intranasal insulin formulations (compare to bioavailability shown in Tables 2, 5 and 10). The bioavailability for formulations from Table 12 was 19.7% and 17.8% for Carbopol and CMC, respectively. The pharmacodynamic effect as shown by % glucose from initial was improved with the addition of thickening agents, such as Carbopol and CMC, to the intranasal insulin formulations.

Additional intranasal formulations comprising a thickening agent such as Carbopol or CMC, were tested and are described in Table 17.

TABLE 17

Insulin Formulations Containing Carbopol or CMC as Thickening Agent

| # | Regular Insulin (IU/mL) | Me-β-CD (mg/mL) | EDTA (mg/mL) | Tween 80 (mg/mL) | Arginine Buffer (mM) | Thickening Agent (mg/mL) | MP (mg/mL) | PP (mg/mL) | PG (mg/mL) | pH |
|---|---|---|---|---|---|---|---|---|---|---|
| 1 | 800 | 45 | 1 | 10 | 10 | CMC LV, 1 mg/mL | 0.33 | 0.17 | 10 | 7.3 |
| 2 | 800 | 45 | 1 | 10 | 10 | CMC LV, 10 mg/mL | 0.33 | 0.17 | 10 | 7.3 |
| 3 | 800 | 45 | 1 | 10 | 10 | Carbopol 974P, 2.5 mg/mL | 0.33 | 0.17 | 10 | 7.3 |
| 4 | 800 | 45 | 1 | 10 | 10 | CMC MV, 10 mg/mL | 0.33 | 0.17 | 10 | 7.3 |
| 5 | 800 | 22.5 | 1 | 10 | 10 | 0.25% Carbopol 974P | 0.33 | 0.17 | 10 | 7.3 |
| 6 | 800 | 10 | 1 | 10 | 10 | | 0.33 | 0.17 | 10 | 7.3 |
| 7 | 800 | 45 | 1 | 5 | 10 | | 0.33 | 0.17 | 10 | 7.3 |
| 8 | 800 | 45 | 1 | 1 | 10 | | 0.33 | 0.17 | 10 | 7.3 |

Abbreviations: LV means low viscosity; MV means medium viscosity

The pharmacokinetic and pharmacodynamic results in rabbits testing these alternative carbopol and CMC thickening agent modified formulations, shown in Table 17, are shown in Tables 18, 19, and 20.

TABLE 18

PK Results after Intranasal Administration of Carbopol and CMC Thickening Agent Modified Insulin Formulations (Table 17) in Rabbits

| Formulation | Dose (IU/kg) | Tmax | Cmax | AUClast |
|---|---|---|---|---|
| 1XPDF 1% Tween 0.1% CMCLV | 12 | 22.50 | 573.66 | 25468.22 |
| 1XPDF 1% Tween 1% CMCLV | 12 | 31.88 | 411.46 | 18547.22 |
| 1XPDF 1% Tween 0.25% Carbopol | 12 | 43.13 | 370.40 | 13774.06 |
| 1XPDF 1% Tween 1% CMC MV | 12 | 27.50 | 409.32 | 15797.13 |
| 0.5XPDF 1% Tween 0.25% Carbopol | 12 | 31.88 | 408.66 | 19360.03 |
| 0.22XPDF 1% Tween 0.25% Carbopol | 12 | 29.29 | 340.46 | 16721.11 |
| 1XPDF 0.5% Tween 0.25% Carbopol | 12 | 22.50 | 324.25 | 9595.94 |
| 1XPDF 0.1% Tween 0.25% Carbopol | 12 | 35.00 | 703.69 | 12845.09 |
| SC Regular Saline | 0.6 | 17.00 | 144.20 | 5885.50 |

TABLE 19

% CV Results after Intranasal Administration of Carbopol and CMC Thickening Agent Modified Insulin Formulations (Table 17) in Rabbits

| Formulation | Dose (IU/kg) | Tmax | Cmax | AUClast |
|---|---|---|---|---|
| 1XPDF 1% Tween 0.1% CMCLV | 12 | 35.6 | 63.2 | 79.4 |
| 1XPDF 1% Tween 1% CMCLV | 12 | 113.7 | 90.2 | 83.4 |
| 1XPDF 1% Tween 0.25% Carbopol | 12 | 84.1 | 63.6 | 60.5 |
| 1XPDF 1% Tween 1% CMC MV | 12 | 92.5 | 54.3 | 87.6 |
| 0.5XPDF 1% Tween 0.25% Carbopol | 12 | 58.7 | 86.5 | 103.3 |
| 0.22XPDF 1% Tween 0.25% Carbopol | 12 | 54.4 | 83.7 | 88.0 |
| 1XPDF 0.5% Tween 0.25% Carbopol | 12 | 50.4 | 68.1 | 69.1 |
| 1XPDF 0.1% Tween 0.25% Carbopol | 12 | 106.1 | 154.0 | 74.3 |
| SC Regular Saline | 0.6 | 73.8 | 28.7 | 62.5 |

TABLE 20

Bioavailability after Intranasal Administration of Carbopol and CMC Thickening Agent Modified Insulin Formulations (Table 17) in Rabbits

| Formulation | Dose (IU/kg) | AUClast | % F |
|---|---|---|---|
| 1XPDF 1% Tween 0.1% CMCLV | 12 | 25468.22 | 21.6 |
| 1XPDF 1% Tween 1% CMCLV | 12 | 18547.22 | 15.8 |
| 1XPDF 1% Tween 0.25% Carbopol | 12 | 13774.06 | 11.7 |
| 1XPDF 1% Tween 1% CMC MV | 12 | 15797.13 | 13.4 |
| 0.5XPDF 1% Tween 0.25% Carbopol | 12 | 19360.03 | 16.4 |
| 0.22XPDF 1% Tween 0.25% Carbopol | 12 | 16721.11 | 14.2 |
| 1XPDF 0.5% Tween 0.25% Carbopol | 12 | 9595.94 | 8.2 |
| 1XPDF 0.1% Tween 0.25% Carbopol | 12 | 12845.09 | 10.9 |
| SC Regular Saline | 0.6 | 5885.50 | |

The 0.5×PDF/1% Tween/0.25% Carbopol and 1×PDF 1%/Tween 1%/CMC (LV) formulations resulted in good bioavailability at 16.4% and 15.8%, respectively. The 1×PDF/1% Tween/0.1% CMC (LV) resulted in the highest insulin bioavailability (21.6%). These data indicate that the addition of thickening agents (e.g., carbopol and CMC) significantly and surprisingly enhance the percent bioavailability of an insulin contained within exemplary pharmaceutical formulations disclosed herein. Such an increase in percent bioavailability is also associated with a $T_{max}$ from about 22 to about 30 minutes in rabbits.

A further rabbit study was performed in which blood insulin and glucose levels were determined at specified time points up to 240 minutes. In addition to thickening agents, these formulations also contained the preservatives methylparaben and/or propylparaben and/or phenylethanol. Glucose concentration was measured in duplicate with a glucometer (e.g., One-Touch Ultra). The formulations tested are listed in Table 21.

TABLE 21

PK and PD Rabbit Study Thickening Agents Plus Preservatives

| Group Number | Formulation | Code |
|---|---|---|
| 1 | 0.1% CMC; 0.033% MP; 0.017% PP | IDFCMC-LDMPPP |
| 2 | 0.1% CMC; 0.333% MP; 0.17% PP | IDFCMC-MPPP |
| 3 | 0.1% CMC; 033% MP; 0.017% PP; 0.2% PE | IDFCMC-MPPPPE |
| 4 | Insulin isotonic saline | SC |
| 5 | 0.25% Carbopol; 0.033% MP; 0.017% PP | IDF-0.25% CHLDMPPP |
| 6 | 0.1% Carbopol; 0.033% MP; 0.017% PP | IDF-0.1% CHLDMPPP |
| 7 | 0.25% Carbopol; 0.33% MP; 0.17% PP; 0.2% PE | IDF-0.25% CHMPPPPE |
| 8 | 0.1% Carbopol; 0.33% MP; 0.17% PP; 0.2% PE | IDF-0.1% CHMPPPPE |
| * | 4.5% MBCD; 0.1% EDTA; 1.0% Tween; 1% PG; Arginine | No Thickening Agent Modified Insulin Formulation |

Abbreviations: PP is Propylparaben; MP is Methylparaben; PE is Phenylethanol; IDF is Insulin delivery Formulation which is 4.5% Me-β-CD, 0.1% EDTA, 1.0% Tween, 1% Propylene Glycol, Arginine The pharmacokinetic results for this rabbit experiment are shown in Tables 22 and 23.

TABLE 22

PK Results after Intranasal Administration of Thickening Agent Plus Preservative Insulin Formulations (Table 21) in Rabbits

| Group Number | Formulation | Tmax (min) | AUC$_{Last}$ (min* µIU/ml) | C$_{max}$ (µIU/ml) | % Bioavailability |
|---|---|---|---|---|---|
| 1 | 0.1% CMC; 0.033% MP; 0.017% PP | 23.6 | 17738.8 | 337.7 | 6.9 |
| 2 | 0.1% CMC; 0.333% MP; 0.17% PP | 20.0 | 26481.0 | 448.5 | 10.3 |
| 3 | 0.1% CMC; 033% MP; 0.017% PP; 0.2% PE | 77.5 | 34782.9 | 817.8 | 13.5 |
| 4 | Insulin isotonic saline | 29.4 | 12891.3 | 173.0 | |
| 5 | 0.25% Carbopol; 0.033% MP; 0.017% PP | 29.2 | 42958.7 | 1405.6 | 16.7 |
| 6 | 0.1% Carbopol; 0.033% MP; 0.017% PP | 22.5 | 64953.6 | 1604.0 | 25.2 |
| 7 | 0.25% Carbopol; 0.33% MP; 0.17% PP; 0.2% PE | 41.3 | 60030.2 | 843.4 | 23.3 |
| 8 | 0.1% Carbopol; 0.33% MP; 0.17% PP; 0.2% PE | 31.4 | 50373.7 | 980.9 | 19.5 |

TABLE 23

% CV Results after Intranasal Administration of Thickening Agent Plus Preservative Insulin Formulations (Table 21) in Rabbits

| Group Number | Formulation | Tmax | AUC$_{Last}$ | C$_{max}$ |
|---|---|---|---|---|
| 1 | 0.1% CMC; 0.033% MP; 0.017% PP | 72.2 | 81.6 | 32.9 |
| 2 | 0.1% CMC; 0.333% MP; 0.17% PP | 47.9 | 98.3 | 58.5 |
| 3 | 0.1% CMC; 033% MP; 0.017% PP; 0.2% PE | 116.3 | 42.2 | 47.0 |
| 4 | Insulin isotonic saline | 57.1 | 34.1 | 22.2 |
| 5 | 0.25% Carbopol; 0.033% MP; 0.017% PP | 87.7 | 65.1 | 55.9 |
| 6 | 0.1% Carbopol; 0.033% MP; 0.017% PP | 71.3 | 120.3 | 113.1 |
| 7 | 0.25% Carbopol; 0.33% MP; 0.17% PP; 0.2% PE | 84.2 | 131.5 | 63.5 |
| 8 | 0.1% Carbopol; 0.33% MP; 0.17% PP; 0.2% PE | 46.6 | 80.9 | 60.6 |

The pharmacokinetic results for formulations in Table 21 showed T$_{max}$ ranging from 20.0 minutes to 77.5 minutes, with AUC$_{Last}$ ranging from 12891.3 µIU/ml to 64953.6 µIU/ml. Bioavailability was increased when thickening agents were added to PDF intranasal insulin formulations. The formulation containing 0.1% Carbopol plus the preservatives MP and PP (Group #6), and the formulation containing 0.25% Carbopol plus preservatives MP, PP and PE (Group #7) provided the highest bioavailability, 25.2% and 23.3%, respectively; and, representing a further increase in bioavailability over the data from experiments performed using formulations manufactured without addition of a thickening agent as presented in Tables 2, 5, and 10.

Example 3

PK and PD Results for Intranasal Administration of Insulin in Humans

Human subjects participated in a seven treatment group study in which the treatment groups included the following: one treatment of a nasal placebo, four regular human insulin (25 IU, 50 IU, 100 IU, and 25 IU/1% PG) intranasal formulations without a thickening agent (shown in Table 24), one treatment of 3 mg rapid-acting insulin aspart subcutaneous injection (NovoLog), and one treatment with human insulin inhalation powder (EXUBERA, 3 mg).

IU is the unit of measurement for the amount of insulin based on measured biological effect (1 IU=0.04167 mg or 23.9 IU=1 mg). The intranasal insulin formulations were 250 to 1000 IU/mL and were delivered in a volume of 0.1 mL. For comparison, Exubera was a dose of about 70 IU.

TABLE 24

Intranasal Insulin Formulations Without a Thickening Agent for Human PK/PD Study

| Formulation Component | Nasal Placebo (STD) | Nasal 25 IU (STD) | Nasal 50 IU (STD) | Nasal 100 IU (STD) | Nasal 1% PG 25 IU (STD) |
|---|---|---|---|---|---|
| Insulin (IU/mL) | 0 | 250 | 500 | 1000 | 250 |
| Me-β-CD (mg/mL) | 45 (4.5%) | 45 (4.5%) | 45 (4.5%) | 45 (4.5%) | 45 (4.5%) |

TABLE 24-continued

Intranasal Insulin Formulations Without a Thickening Agent for Human PK/PD Study

| Formulation Component | Nasal Placebo (STD) | Nasal 25 IU (STD) | Nasal 50 IU (STD) | Nasal 100 IU (STD) | Nasal 1% PG 25 IU (STD) |
|---|---|---|---|---|---|
| DDPC (mg/mL) | 1 | 1 | 1 | 1 | 0 |
| EDTA (mg/mL) | 1 (0.1%) | 1 (0.1%) | 1 (0.1%) | 1 (0.1%) | 1 (0.1%) |
| Polysorbate 80 (mg/mL) | 10 (1%) | 10 (1%) | 10 (1%) | 10 (1%) | 10 (1%) |
| Arginine (mM) | 10 | 10 | 10 | 10 | 10 |
| Sodium Chloride (mg/mL) | 4 | 4 | 4 | 4 | 0 |
| Propylparaben Sodium (mg/mL) | 0.17 (0.1%) | 0.17 (0.1%) | 0.17 (0.1%) | 0.17 (0.1%) | 0.17 (1%) |
| Methylparaben Sodium (mg/mL) | 0.33 | 0.33 | 0.33 | 0.33 | 0.33 |
| Propylene Glycol (mg/mL) | 1 | 1 | 1 | 1 | 10 |
| Sodium Hydroxide | TAP | TAP | TAP | TAP | TAP |
| Purified Water | quantity sufficient | quantity sufficient | quantity sufficient | quantity sufficient | quantity sufficient |
| pH | 7.0-7.6 | 7.0-7.6 | 7.0-7.6 | 7.0-7.6 | 7.0-7.6 |

Abbreviation: TAP means to adjust pH

Figure 4:
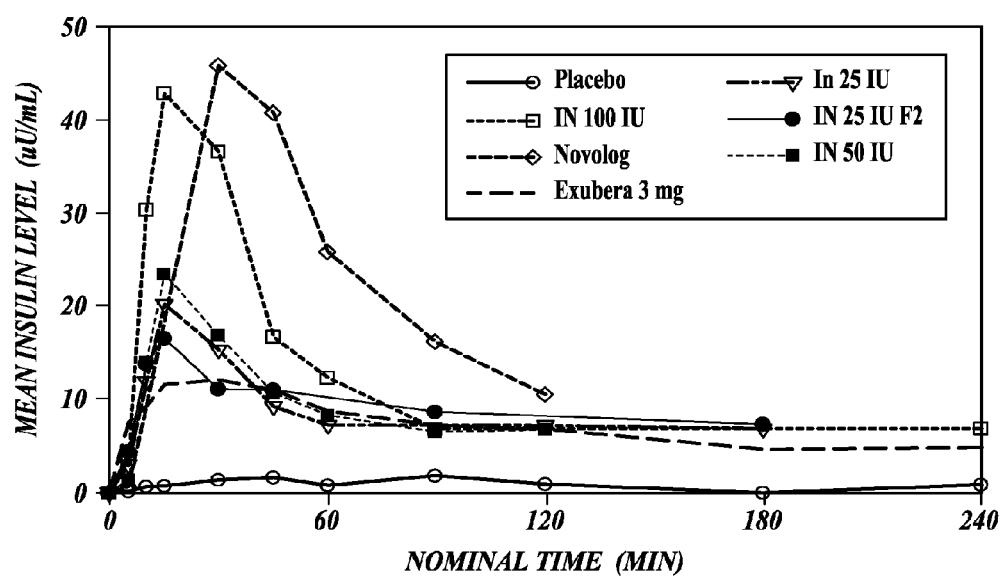
FIG. 4: Pharmacokinetic data, mean insulin levels, for human subjects dosed with 25 IU, 50 IU, and 100 IU intranasal insulin formulations, NOVOLOG (aspart insulin), EXUBERA (inhaled insulin) and placebo.

Plasma insulin and glucose levels were measured at 12 time points up to six hours. Pharmacokinetic parameters, including $T_{max}$, $C_{max}$, and $AUC_{last}$ were calculated based on plasma concentrations of insulin for each subject. FIG. 4 shows the pharmacokinetic profile for the four intranasal doses (25 IU, 50 IU, 100 IU, and 25 IU/1% PG), EXUBERA, NovoLog, and the control (Nasal Placebo). Pharmacokinetic calculations were performed using commercial software (WinNonlin). $AUC_{0-\infty}$, $K_e$, and $t_{1/2}$ were calculated when the data permitted accurate estimation. Statistical analysis of bioavailability data was calculated.

The pharmacokinetic profile (mean serum insulin) and relative percent bioavailability for the IN formulations and EXUBERA compared to NovoLog of the described formulations are shown in FIG. 4 and also embodied below in Table 25.

With respect to time to maximum plasma level for insulin or $T_{max}$, the four intranasal doses (25 IU, 50 IU, and 100 IU, and 25 IU/1% PG insulin) had $T_{max}$ values of about 16 to about 19 minutes, which provided the shortest $T_{max}$ values compared to the rapid-acting insulin aspart (NovoLog) and inhaled insulin (EXUBERA). With respect to plasma insulin levels ($C_{max}$), rapid-acting insulin aspart injection (NovoLog) had the highest concentration, followed by the four nasal formulations, with inhaled insulin (EXUBERA) having the lowest. With respect to the extent of absorption, rapid-acting insulin aspart injection (NovoLog) had the greatest total exposure or $AUC_{last}$, with the highest dose of four nasal formulations next (100 IU), followed by the inhaled insulin (EXUBERA) and then the lower doses of the three nasal spray formulations (25 IU, 25 IU 1% PG and 50 IU). The intranasal formulations resulted in quicker return to baseline insulin levels compared to Exubera.

The bioavailability of the insulin intranasal formulations ranged between about 4.8-14.8% (relative to SC NovoLog).

TABLE 25

Pharmacokinetic Results after Administration of Intranasal Insulin Formulations Without a Thickening Agent to Human Subjects

| | Pharmacokinetic Parameters | | | | |
|---|---|---|---|---|---|
| Formulation | $T_{max}$ (min) (STD) | $C_{max}$ (μU/mL) (STD) | $AUC_{last}$ (min*μU/mL) (STD) | $AUC_{inf}$ (min*μU/mL) | Relative % BA Compared to NovoLog (STD) |
| Nasal Placebo (control) | 63.8 (30.92) | 2.8 (3.98) | 273.1 (452.11) | 5106.7 | — |
| NovoLog | 38.3 (30.92) | 52 (31.35) | 2484.7 (998.4) | 3502.4 | — |
| EXUBERA (3 mg) | 23.4 (14.68) | 14.5 (4.21) | 1194.2 (699.05) | 3703.7 | 7.1 (6.3) |
| Nasal (25 IU) | 19.2 (6.95) | 21 (8.61) | 724.8 (469.55) | 1834.5 | 10.1 (8.0) |
| Nasal (50 IU) | 16.2 (4.94) | 23.5 (16.99) | 670.8 (598.94) | 1366.3 | 5.2 (5.39) |
| Nasal (100 IU) | 16.8 (6.81) | 43.6 (44.66) | 1368 (1898.56) | 2634.5 | 4.8 (4.8) |
| Nasal 25 IU 1% PG | 24.4 (26.52) | 17.8 (10.57) | 724.1 (652.72) | 3494.9 | 14.8 (22.6) |

25 IU and 25 IU/1% PG formulations had a higher mean % bioavailability than Exubera (7.1%) in this study. The highest bioavailability was achieved by the intranasal 25 IU/1% PG formulation (14.8%).

The % CV results are shown in Table 26.

TABLE 26

% CV Results after Administration of Intranasal Insulin Formulations Without a Thickening Agent to Human Subjects

| Formulation | % CV Results | | | |
|---|---|---|---|---|
| | $T_{max}$ (min) | $C_{max}$ (μU/mL) | $AUC_{last}$ (min*μU/mL) | $AUC_{inf}$ (min*μU/mL) |
| Nasal Placebo (control) | 48.5 | 141.5 | 162.5 | — |
| NovoLog | 26.8 | 60.3 | 40.2 | 23.5 |

TABLE 26-continued

% CV Results after Administration of Intranasal Insulin Formulations Without a Thickening Agent to Human Subjects

| Formulation | % CV Results | | | |
|---|---|---|---|---|
| | $T_{max}$ (min) | $C_{max}$ (μU/mL) | $AUC_{last}$ (min*μU/mL) | $AUC_{inf}$ (min*μU/mL) |
| EXUBERA (3 mg) | 62.6 | 29.1 | 58.5 | 87.4 |
| Nasal (25 IU) | 36.3 | 41.1 | 68.8 | 41.7 |
| Nasal (50 IU) | 30.5 | 72.2 | 89.5 | 47.8 |
| Nasal (100 IU) | 40.5 | 102.3 | 140.3 | 85.2 |
| Nasal 25 IU 1% PG | 108.8 | 59.5 | 90.1 | 63.9 |

The AUC intersubject % CV was approximately 70-140% for 25 IU, 50 IU, and 100 IU TN groups, and 90.1% for the 25 IU 1% PG group. The % CV for Exubera was 60%, and NovoLog was 40%.

A glucometer was used to measure glucose levels for the pharmacodynamic data collection. For each sample, the time to maximum % glucose fall from initial (Tmax) and maximum % glucose fall from initial (Cmax or % Fall) were calculated. A summary of the glucose maximum % Fall and Time to maximum % Fall percent reduction in glucose for each treatment group is shown in Table 27. The maximum % glucose fall from initial was approximately 55% for NovoLog and 20-30% for the IN formulations. The incidence of 30%, 20%, and 10% reduction in glucose percent for each treatment group is shown in Table 28.

TABLE 27

Glucose maximum % Fall and Time to Maximum % Fall Results after Administration of Intranasal Insulin Formulations Without a Thickening Agent to Human Subjects

| Treatment Group | Glucose Max % Fall | Time to Max % Fall (min) |
|---|---|---|
| Nasal Placebo | 6.4 | 193.6 |
| NovoLog (SC) | 55.8 | 50.5 |
| Exubera 3 mg | 22.5 | 105 |
| Nasal 25 IU | 19.8 | 43.6 |
| Nasal 50 IU | 24.7 | 109.1 |
| Nasal 100 IU | 30.5 | 69.5 |
| Nasal 25 IU 1% PG | 21.9 | 61.9 |

TABLE 28

Incidence of Human Subjects with 30%, 20%, and 10% Glucose Reduction Results after Administration of Intranasal Insulin Formulations Without a Thickening Agent to Human Subjects

| Treatment Group | # of Subjects | Subjects with Glucose % Reduction | | |
|---|---|---|---|---|
| | | GE 30% N (%) | GE 20% N (%) | GE 10% N (%) |
| Nasal Placebo | 812 | 0 (0%) | 1 (12.58.3%) | 4 (5033%) |
| NovoLog (SC) | 812 | 8 (100%) 10 (83.3%) | 812 (100%) | 812 (100%) |
| Exubera 3 mg Nasal 25 IU | 711 | 1 (14.30 (0%) | 4 (57.1%) 5 (45.5%) | 8 (72.7 (100%) |
| Nasal 2550 IU | 811 | 1 (12.5%) 4 (36.4%) | 4 (506 (54.5%) | 7 (87.5%) 9 (81.8%) |
| Nasal 50100 IU | 811 | 2 (253 (27.3%) | 4 (5036.4%) | 811 (100%) |
| Nasal 100 IU Exubera 3 mg | 86 | 2 (33.3 (37.5%) | 5 (62.5%) 4 (66.7%) | 86 (100%) |
| Nasal 25 IU 1% PG | 8 | 2 (25%) | 4 (50%) | 7 (87.5%) |

The results of this pharmacodynamic study demonstrate that intranasal administration of insulin is effective in reducing a patient's blood glucose level (reflected as % glucose fall). The mean % glucose change from baseline results showed a more rapid glucose fall for intranasally administered insulin compared to EXUBERA and NovoLog.

The pharmacokinetic-pharmacodynamic relationship demonstrated a high correlation between either $C_{max}$ or $AUC_{last}$ and the maximum glucose response. There were no observed side effects (adverse reactions) resulting from intranasal administration of insulin, including clinically significant hypoglycemia. The intranasal insulin doses were well tolerated and post-dose nasal examinations were normal. There were no clinically important changes in vital signs (systolic or diastolic blood pressure and heart rate), ECG, or physical examination during the course of the study.

Example 4

PK and PD Results for Intranasal Administration of Insulin Formulations Containing a Thickening Agent in Humans This example describes intranasal insulin formulations containing various thickening agents that were tested in human subjects. The intranasal insulin formulations containing the thickening agents carboxymethylcellulose sodium—low viscosity (CMC) and carbopol, described in Table 29, were tested.

TABLE 29

Insulin Formulations Containing a Thickening Agent for Human PK/PD Study

| Formulation Component | Nasal Plus CMC (25 IU) | Nasal Plus CMC (50 IU) | Nasal Plus CH (25 IU) | Nasal Plus CH (50 IU) |
|---|---|---|---|---|
| Insulin (IU/mL) | 250 | 500 | 250 | 500 |
| Me-β-CD (mg/mL) | 45 (4.5%) | 45 (4.5%) | 45 (4.5%) | 45 (4.5%) |
| EDTA (mg/mL) | 1 (0.1%) | 1 (0.1%) | 1 (0.1%) | 1 (0.1%) |
| Polysorbate 80 (mg/mL) | 10 (1%) | 10 (1%) | 10 (1%) | 10 (1%) |
| CMC (mg/mL) | 1 (0.1%) | 1 (0.1%) | 0 | 0 |
| Carbopol (mg/mL) | 0 | 0 | 2.5 (0.25%) | 2.5 (0.25%) |
| Arginine (mg/mL) | 2.1 | 2.1 | 2.1 | 2.1 |
| Propylene Glycol (PG) (mg/mL) | 10 (1%) | 10 (1%) | 10 (1%) | 10 (1%) |
| Propylparaben Sodium (PP) (mg/mL) | 0.17 | 0.17 | 0.17 | 0.17 |
| Methylparaben Sodium (MP) (mg/mL) | 0.33 | 0.33 | 0.33 | 0.33 |
| Purified Water | quantity sufficient | quantity sufficient | quantity sufficient | quantity sufficient |
| Sodium Hydroxide | TAP | TAP | TAP | TAP |
| pH | 7 | 7 | 7 | 7 |

Abbreviations: CH means carbomer homopolymer (trade name: Carbopol 974P)

The methyl-β-cyclodextrin used in these intranasal formulations was tested in six and nine month toxicity studies in rats and dogs, respectively with no signs of systemic or nasal toxicity. In addition, these excipients have been administered to humans in other formulations with no signs of systemic or nasal toxicity. The other excipients, i.e., Carbopol 974P (a carbomer homopolymer), carboxy-methylcellulose, and polysorbate 80 are either generally recognized as safe (GRAS), listed in the FDA Inactive Ingredient Guide, or contained in ophthalmic or other nasal products at the same or higher concentrations.

Absorption, tolerance and bioavailability data were collected for insulin (insulin regular) nasal spray formulations containing a thickening agent and compared to subcutaneous insulin (NovoLog) in healthy human subjects. The study included 12 healthy male and female subjects between the ages of 18 and 45 years with no history of diabetes or hypoglycemia, and a body mass index between 20-28 kg/m². Each subject was administered ascending doses of insulin starting with nasal placebo, then subcutaneous administration of NovoLog at a dose of 20% of 0.6 IU/kg (not to exceed 10 IU) followed by the nasal doses of 25 and 50 IU per formulation (50 IU dose was given as 25 IU nasal spray per nostril). Each insulin administration was given at least 24 hours apart. Subjects were fasted overnight and given a standard meal 5 minutes after dosing. The subjects were monitored for symptoms and glucose was monitored by glucometer (finger stick).

Prior to intranasal administration, the assembled nasal spray pump and bottle (applicator) were primed. Subject was instructed to gently blow his/her nose. The primed intranasal applicator was gently inserted into the nostril. The bottle was tilted to be in a straight line with the nasal passage. The pump was firmly pressed down once to spray the medication into the subject's nose while he/she gently inhaled. The subjects were instructed to remain upright for a minimum of 15 minutes following dosing. Subject refrained from blowing his/her nose for 1 hour following intranasal administration.

Figure 5:
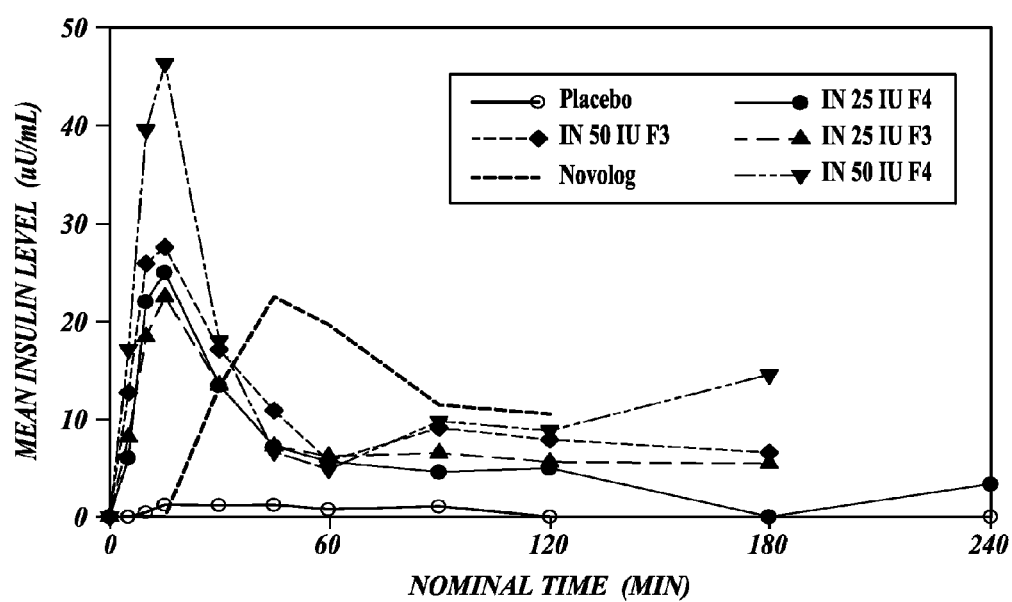
FIG. 5: Pharmacokinetic data, mean insulin levels, for human subjects dosed with 25 IU and 50 IU of intranasal insulin formulations containing a thickening agent and control formulations (placebo and NovoLog).

Blood samples for analysis of insulin, glucose and C-Peptide levels were collected at 0 (pre-first dose), 5, 10, 15, 30, 45, 60, 90 minutes and 2, 3, 4, and 5 hours post-dose. The following pharmacokinetic parameters were calculated based on plasma concentrations of insulin for each subject: $C_{max}$, $t_{max}$, and $AUC_{0-t}$. Pharmacokinetic calculations were performed using commercial software (WinNonlin). $AUC_{0-\infty}$, $K_e$, and $t_{1/2}$ were calculated when the data permitted accurate estimation. Pharmacokinetic data is shown in Table 30, and mean serum insulin levels for the groups tested in this example are shown in FIG. 5. The % CV results are shown in Table 31.

Statistical analysis of pharmacokinetic/pharmacodynamic data (bioavailability) was calculated. Differences for all pharmacokinetic/pharmacodynamic variables, except Tmax between each formulation of insulin nasal spray versus the reference (subcutaneous NovoLog) were evaluated using two-sided pair T-test. A separate analysis was performed for each formulation of insulin nasal spray versus the reference.

TABLE 30

Pharmacokinetic Parameters of Intranasal Insulin Formulations Containing a Thickening Agent Administered to Human Subjects

| Formulation | $T_{max}$ min (STD) | $C_{max}$ μU/mL (STD) | $AUC_{last}$ min*μU/mL (STD) | $AUC_{inf}$ min*μU/mL (STD) | Relative % BA Compared to NovoLog (STD) |
|---|---|---|---|---|---|
| Nasal Placebo (control) | 45 (32.4) | 2.5 (3.81) | 79.6 (163.82) | — | — |
| NovoLog | 51.3 (14.94) | 24.3 (9.96) | 1246.9 (562.46) | 2089.1 (658.55) | — |
| Nasal (25 IU) Plus CMC | 14.6 (5.42) | 23.7 (14.53) | 885.6 (637.66) | 2779.3 (1693.96) | 28.4 (18.8) |
| Nasal (50 IU) Plus CMC | 30 (35.99) | 31.2 (21.98) | 991.6 (964.27) | 1584.8 (1044.42) | 16.8 (15.11) |

TABLE 30-continued

Pharmacokinetic Parameters of Intranasal Insulin Formulations
Containing a Thickening Agent Administered to Human Subjects

| Formulation | $T_{max}$ min (STD) | $C_{max}$ μU/mL (STD) | $AUC_{last}$ min*μU/mL (STD) | $AUC_{inf}$ min*μU/mL (STD) | Relative % BA Compared to NovoLog (STD) |
|---|---|---|---|---|---|
| Nasal (25 IU) Plus Carbopol | 26.7 (22.6) | 28.7 (13.53) | 915.4 (479) | 1468.4 (958.53) | 30.6 (16.43) |
| Nasal (50 IU) Plus Carbopol | 14.6 (1.44) | 47.2 (34.94) | 1319.7 (930.69) | 1529 (872.27) | 21.5 (14.16) |

TABLE 31

% CV Results for Intranasal Insulin Formulations Containing a Thickening Agent Administered to Human Subjects

| | % CV Results | | | |
|---|---|---|---|---|
| Formulation | $T_{max}$ (min) | $C_{max}$ (μU/mL) | $AUC_{last}$ (min*μU/mL) | $AUC_{inf}$ (min*μU/mL) |
| Nasal Placebo (control) | 72 | 151.9 | 205.8 | — |
| NovoLog | 29.2 | 41.1 | 45.1 | 31.5 |
| Nasal (25 IU) Plus CMC | 37.2 | 61.4 | 72 | 60.9 |
| Nasal (50 IU) Plus CMC | 120 | 70.4 | 97.2 | 65.9 |
| Nasal (25 IU) Plus Carbopol | 84.7 | 47.2 | 52.3 | 65.3 |
| Nasal (50 IU) Plus Carbopol | 9.9 | 74 | 70.5 | 57 |

These results show that addition of a thickening agent to the intranasal insulin formulation disclosed herein resulted in an increase in insulin bioavailability compare to formulations without thickening agent, compare to Table 25. The relative % bioavailability of the insulin intranasal formulations containing a thickening agent ranged from about 16.8-30.6%. The highest bioavailability was achieved with intranasal administration of the 25 IU insulin in the 0.25% carbopol formulation.

The AUC intersubject % CV was approximately 70-97% and 50-72% for the CMC and Carbopol IN groups, respectively. The AUC intersubject % CV was approximately 45% for NovoLog. The Cmax intersubject % CV was approximately 61-70% and 46-74% for the CMC and Carbopol IN groups, respectively. The Cmax intersubject % CV was approximately 41% for NovoLog.

When contrasted to the data presented in Table 25, the addition of a thickening agent (as presented in Table 30) increased the extent of insulin absorption. For example, at 50 IU, the extent of absorption (i.e., total exposure or $AUC_{last}$) doubled in the presence of the thickening agent carbopol (1319.7 μU/ml, compared to 670.8 μU/ml). Similar increases in extent of absorption were detected when the thickening agent was CMC. In each case, there is also a corresponding increase in $C_{max}$.

Figure 6:
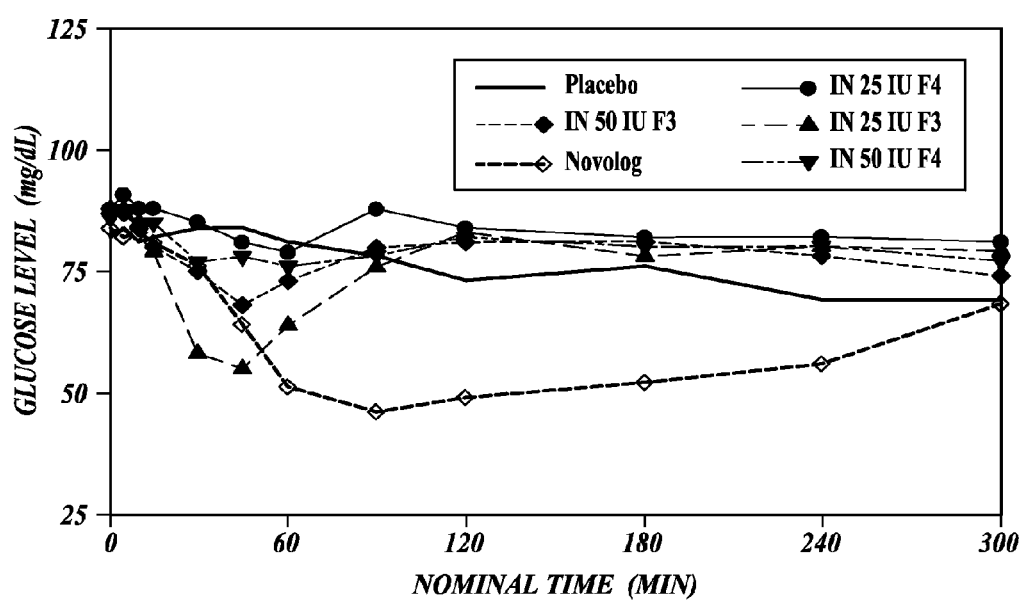
FIG. 6: Pharmacodynamic data, glucose levels, for human subjects dosed with 25 IU and 50 IU of intranasal insulin formulations containing a thickening agent and control formulations (placebo and NovoLog).

Analysis for pharmacodynamic parameters for each dose based on glucose levels was conducted. The mean percent glucose reduction data is shown in FIG. 6. For each sample, the time to maximum % glucose fall from initial (Tmax) and maximum % glucose fall from initial (Cmax or % Fall) were calculated, data is shown in Table 32 and Table 33, respectively.

TABLE 32

Glucose maximum % Fall and Time to Maximum % Fall Results for Intranasal Insulin Formulations Containing a Thickening Agent Administered to Human Subjects

| Treatment Group | Glucose Max % Fall | Time to Max % Fall (min) |
|---|---|---|
| Nasal Placebo (control) | 5.8 (4.93) | 101.3 (90.43) |
| NovoLog | 47.3 (8.54) | 87.5 (50.29) |
| Nasal (25 IU) Plus CMC | 23.7 (16.93) | 88.8 (91.68) |
| Nasal (50 IU) Plus CMC | 33.2 (20.99) | 56.3 (58.31) |
| Nasal (25 IU) Plus Carbopol | 30.6 (17.15) | 75 (77.81) |
| Nasal (50 IU) Plus Carbopol | 37 (17.45) | 42.5 (12.52) |

TABLE 33

Incidence of Human Subjects with 30%, 20%, and 10% Glucose Reduction Results for Intranasal Insulin Formulations Containing a Thickening Agent Administered to Human Subjects

| | | Subjects with Glucose % Reduction | | |
|---|---|---|---|---|
| Treatment Group | # of Subjects | GE 30% N (%) | GE 20% N (%) | GE 10% N (%) |
| Nasal Placebo (control) | 12 | 0 (0%) | 0 (0%) | 6 (50%) |
| NovoLog | 12 | 12 (100%) | 12 (100%) | 12 (100%) |
| Nasal (25 IU) Plus CMC | 12 | 1 (8.3%) | 7 (58.3%) | 12 (100%) |
| Nasal (50 IU) Plus CMC | 12 | 6 (50%) | 8 (66.7%) | 10 (83.3%) |
| Nasal (25 IU) Plus Carbopol | 12 | 5 (41.7%) | 8 (66.7%) | 10 (83.3%) |
| Nasal (50 IU) Plus Carbopol | 12 | 8 (66.7%) | 10 (83.3%) | 12 (100%) |

The mean glucose change results shown in FIG. 6 illustrates more rapid glucose fall for intranasally administered insulin compared to NovoLog. The time to maximum % glucose fall for Nasal Plus CMC and Nasal Plus Carbopol (both at 50 IU) was faster than NovoLog. There was a statistical correlation for AUC and Cmax for maximum % glucose fall levels. The nasal formulations time to return to baseline glucose levels was quicker (90-120 minutes) compared to NovoLog (240-300 minutes) and Exubera (>360 minutes, data not shown).

Figure 7:
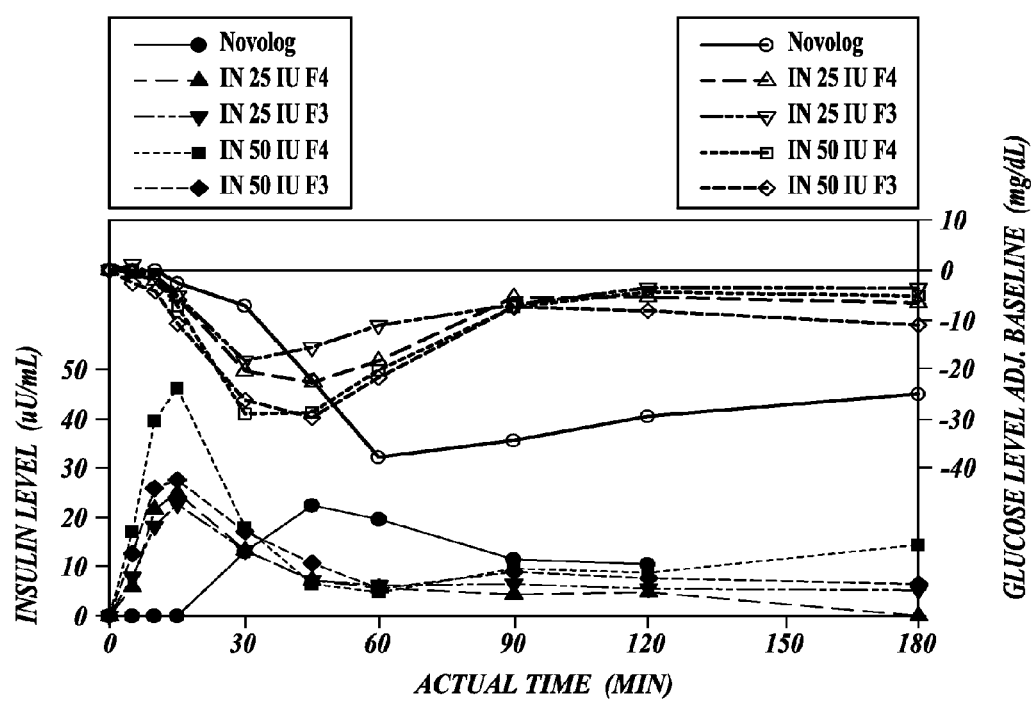
FIG. 7: Insulin levels and mean glucose levels adjusted to baseline for human subjects dosed with 25 IU and 50 IU of intranasal insulin formulations containing a thickening agent and a control formulation (NovoLog).

A summary of the mean serum insulin levels (pharmacokinetic) and mean glucose levels adjusted to baseline (PD) for human subjects dosed with 25 IU and 50 IU doses of intranasal insulin formulations containing a thickening agent and a control formulation (NovoLog) is shown in FIG. 7. This figure illustrates that the intranasal insulin formulations containing a thickening agent result in an ultra-rapid acting insulin profile compared to SC NovoLog in humans.

All IN formulations with a thickening agent were well tolerated with no signs of nasal irritation.

Example 5

Physical and Chemical Stability of Nasal Spray Formulations of Regular Human Insulin Physical and chemical stability of nasal spray formulation were tested. Samples were prepared as described in Tables 34 (formulations without a thickening agent) and 35 (formulations containing a thickening agent). The materials used for manufacture of the formulations are shown in Table 36. Osmolality, appearance, density, viscosity, refractive index and UV absorbance were tested at approximately T=0 for all formulations. Additionally, insulin and preservatives content and purity were tested by HPLC.

TABLE 34

Manufacture of Insulin Formulations Without a Thickening Agent

| # | Regular Insulin (IU/mL) | Me-β-CD (mg/mL) | EDTA | Tween 80 | Arginine (mM) | MP | PP (mg/mL) | PG | pH | Sample Prep |
|---|---|---|---|---|---|---|---|---|---|---|
| 1 | 100 | 0 | 0 | 0 | 10 | 0 | 0 | 0 | 2.0 | 0.22 µm filtered |
| 2 | 100 | 0 | 0 | 0 | 10 | 0 | 0 | 0 | 3.0 | 0.22 µm filtered |
| 3 | 100 | 0 | 0 | 0 | 10 | 0 | 0 | 0 | 7.3 | 0.22 µm filtered |
| 4 | 250 | 45 | 1 | 0 | 10 | 0.33 | 0.17 | 10 | 7.3 | 0.22 µm filtered |
| 5 | 500 | 45 | 1 | 0 | 10 | 0.33 | 0.17 | 10 | 7.3 | 0.22 µm filtered |
| 6 | 250 | 0 | 1 | 10 | 10 | 0.33 | 0.17 | 10 | 7.3 | 0.22 µm filtered |
| 7 | 500 | 0 | 1 | 10 | 10 | 0.33 | 0.17 | 10 | 7.3 | 0.22 µm filtered |
| 8 | 0 | 45 | 1 | 10 | 10 | 0.33 | 0.17 | 10 | 7.3 | 0.22 µm filtered |
| 9 | 250 | 45 | 1 | 10 | 10 | 0.33 | 0.17 | 10 | 7.3 | 0.22 µm filtered |
| 10 | 500 | 45 | 1 | 10 | 10 | 0.33 | 0.17 | 10 | 7.3 | 0.22 µm filtered |
| 11 | Humulin ® R, 100 U | | | | | | | | | 0.22 µm filtered |
| 12 | Humulin ® R, 500 U | | | | | | | | | 0.22 µm filtered |
| 13 | NovoLog ®, 100 U | | | | | | | | | 0.22 µm filtered |

TABLE 35

Manufacture of Viscosity Enhanced Insulin Formulations

| # | Regular Insulin (IU/mL) | Me-β-CD (mg/mL) | Tween 80 | Arginine Buffer (mM) | Carbopol 974P | NaCl | CMC LV (mg/ml) | MP | PP | PG |
|---|---|---|---|---|---|---|---|---|---|---|
| 1 | 0 | 0 | 0 | 10 | 0 | 4 | 0 | 0 | 0 | 0 |
| 2 | 0 | 0 | 0 | 10 | 0 | 4 | 0 | 0.33 | 0.17 | 0 |
| 3 | 0 | 0 | 10 | 10 | 0 | 4 | 0 | 0.33 | 0.17 | 0 |
| 4 | 0 | 45 | 0 | 10 | 0 | 4 | 0 | 0.33 | 0.17 | 0 |
| 5 | 0 | 0 | 0 | 10 | 0 | 0 | 0 | 0.33 | 0.17 | 10 |
| 6 | 250 | 0 | 0 | 10 | 0 | 0 | 0 | 0.33 | 0.17 | 10 |
| 7 | 500 | 0 | 0 | 10 | 0 | 0 | 0 | 0.33 | 0.17 | 10 |
| 8 | 0 | 0 | 0 | 10 | 0 | 4 | 1 | 0 | 0 | 0 |
| 9 | 0 | 0 | 0 | 10 | 0 | 0 | 1 | 0.33 | 0.17 | 10 |
| 10 | 0 | 0 | 10 | 10 | 0 | 0 | 1 | 0.33 | 0.17 | 10 |
| 11 | 0 | 45 | 0 | 10 | 0 | 0 | 1 | 0.33 | 0.17 | 10 |
| 12 | 250 | 45 | 10 | 10 | 0 | 0 | 1 | 0.33 | 0.17 | 10 |
| 13 | 500 | 45 | 10 | 10 | 0 | 0 | 1 | 0.33 | 0.17 | 10 |
| 14 | 0 | 0 | 0 | 10 | 2.5 | 4 | 0 | 0 | 0 | 0 |
| 15 | 0 | 0 | 0 | 10 | 2.5 | 0 | 0 | 0.33 | 0.17 | 10 |
| 16 | 0 | 0 | 10 | 10 | 2.5 | 0 | 0 | 0.33 | 0.17 | 10 |
| 17 | 0 | 45 | 0 | 10 | 2.5 | 0 | 0 | 0.33 | 0.17 | 10 |
| 18 | 250 | 45 | 10 | 10 | 2.5 | 0 | 0 | 0.33 | 0.17 | 10 |
| 19 | 500 | 45 | 10 | 10 | 2.5 | 0 | 0 | 0.33 | 0.17 | 10 |

TABLE 35-continued

Manufacture of Viscosity Enhanced Insulin Formulations

| # | Regular Insulin (IU/mL) | Me-β-CD (mg/mL) | Tween 80 (mg/mL) | Arginine Buffer (mM) | Carbopol 974P | NaCl | CMC LV (mg/ml) | MP | PP | PG |
|---|---|---|---|---|---|---|---|---|---|---|
| 20 | 0 | 45 | 10 | 10 | 0 | 0 | 0 | 0.33 | 0.17 | 10 |
| 21 | 250 | 45 | 10 | 10 | 0 | 0 | 0 | 0.33 | 0.17 | 10 |
| 22 | 500 | 45 | 10 | 10 | 0 | 0 | 0 | 0.33 | 0.17 | 10 |

TABLE 36

Materials Used in Manufacture of Insulin Nasal Spray Formulations

| Chemical | Grade | Vendor | Cat # |
|---|---|---|---|
| Human Insulin, Recombinant, GMP | USP | Diosynth | — |
| Methyl-β-Cyclodextrin (Me-β-CD) | Pharma | Wacker | 60007006 |
| Edetate Disodium (EDTA) | USP | J T Baker | 8994 |
| Polysorbate 80 (Tween 80) (INS-019) | USP | J T Baker | 4117 |
| Polysorbate 80 (Tween 80) (INS-111) | NF | Spectrum | P0138 |
| L-Arginine (INS-019) Hydrochloride | USP | J T Baker | 2067 |
| L-Arginine (INS-111) Hydrochloride | USP | J T Baker | 2067 |
| Carboxymethylcellulose, low viscosity | USP | Spectrum | CA193 |
| Carbopol 974P (Carbomer Homopolymer) | USP | Novcon | — |
| Sodium Chloride (NaCl) | USP | Spectrum | S0155 |
| Methylparaben | NF | Nastech (J T Baker) | 6215-18 |
| Propylparaben | NF | Nastech (J T Baker) | 7624-18 |
| Propylene Glycol | USP | JT Baker | 9403 |
| Sterile Water For Irrigation (INS-019) | USP | Spectrum/Braun | S1944 |
| Sterile Water For Irrigation (INS-111) | USP | Spectrum/Braun | S1944 |
| 2N Hydrochloric Acid | Research | J T Baker | 5616-02 |
| 2N Sodium Hydroxide | Research | J T Baker | 5633-02 |
| 12 mm polystyrene cuvette | — | Malvern Corp. | ZEN0112 |
| 1 cc sterile disposable syringes | — | B D Corp. | 309628 |
| 0.22 μm PDVF filter | — | Millipore | SLGV013 SL |

The pH was measured using a Cole Parmer semi-micro NMR tube glass pH probe (cat #05990-30) or equivalent with Orion 520Aplus pH meter, Thermo Electron Corp (USA) or equivalent. The pH specification for insulin nasal spray was 7.3±0.3.

The osmolality of the formulations were measured with an Advanced Micro Osmometer, Model 2020, Advanced Instruments Inc. (Norwood, Mass.). The osmolality specification for insulin nasal spray was 200-280 mOsm/kg $H_2O$.

Density measurements are made using the DMA 5000 Density Meter, Anton Paar USA (Ashland, Va.). The density is measured based on the oscillating U-tube principle.

Formulation viscosities were measured using an AMVn Automated Micro Viscometer, Anton Paar USA (Ashland, Va.). The AMVn determined the dynamic and kinematic viscosity of liquids by the rolling/falling ball principle which is based on Stoke's law.

Refractive Index (RI) measurements were performed using a Palm Abbe PA202 Digital Refractometer, Misco Instruments (Cleveland, Ohio). Light from an LED light was passed through the sample; some of the light is transmitted through the solution and lost while the remaining light is reflected onto a linear array of photodiodes through a sapphire prism. This was then correlated by the internal software to refractive index and displayed on the LCD screen.

UV absorbances of all samples was measured using the Spectramax MS and SoftMax Pro v. 5.0 software, Molecular Devices, Sunnyvale, Calif. The UV absorbance was read at 633 nm (i.e., the wavelength of the Helium-Neon laser used by the Malvern Zetasizer Nano ZS for the purposes of particle sizing).

HPLC analysis was conducted on samples at T=0 to verify insulin and preservative content. The outputs of the analysis include Insulin Identification, Insulin Assay, A-21 Desamido Insulin Content, Total Other Insulin-Related Impurities Content, Methylparaben Identification, Methylparaben Assay, Propylparaben Identification, and Propylparaben Assay. The final product specifications for these measurements for the insulin nasal spray are listed in Table 37.

TABLE 37

Specifications for Insulin Nasal Spray

| Category | Specification |
|---|---|
| Insulin Identification | The retention time of the major peak in the chromatogram corresponds to that of the standard preparation (pH = 7.3 ± 0.3; Osmolality = 200-280 mOsm/kg $H_2O$) |

TABLE 37-continued

Specifications for Insulin Nasal Spray

| Category | Specification |
|---|---|
| Insulin Assay | 80.0-120.0% of Formulation Label Claim |
| Insulin Related Substances Assay | A-21 Desamido Insulin Content: ≤10.0% of Insulin Related Peaks<br>Other Insulin Related Substances: ≤5.0% of Insulin Related Peaks |
| Methylparaben Identification | The retention time of the major peak in the chromatogram corresponds to that of the standard preparation |
| Methylparaben Assay | N/A |
| Propylparaben Identification | The retention time of the major peak in the chromatogram corresponds to that of the standard preparation |
| Propylparaben Assay | N/A |

Summaries of physical analyses of formulations from Tables 34 and 35 are shown in below Table 38 and Table 39, respectively.

TABLE 38

Physical and Chemical Analysis of Insulin Formulations Without a Thickening Agent

| Sample # | pH | Osmolality (mOsm/kg H2O) | Appearance | Density (g/cc) | Viscosity (mPa-s) |
|---|---|---|---|---|---|
| 1 | 2.0 | 42 | clear and colorless solution | 0.999 | 0.888 |
| 2 | 3.0 | 25 | clear and colorless solution | 0.999 | 0.902 |
| 3 | 7.4 | 43 | clear and colorless solution | 0.999 | 0.902 |
| 4 | 7.3 | 242 | clear and colorless solution | 1.014 | 0.901 |
| 5 | 7.2 | 260 | clear and colorless solution | 1.017 | 1.094 |
| 6 | 7.4 | 198 | clear and colorless solution | 1.003 | 1.133 |
| 7 | 7.2 | 211 | clear and colorless solution | 1.005 | 1.006 |
| 8 | 7.3 | 220 | clear and colorless solution | 1.012 | 1.047 |
| 9 | 7.4 | 243 | clear and colorless solution | 1.015 | 1.060 |
| 10 | 7.4 | 264 | clear and colorless solution | 1.017 | 1.287 |
| 11 | 7.5 | 213 | clear and colorless solution | 1.002 | 1.330 |
| 12 | 7.4 | 257 | clear and colorless solution | 1.006 | 0.944 |
| 13 | 7.3 | 267 | clear and colorless solution | 1.004 | 0.991 |

TABLE 39

Physical and Chemical Analysis of Insulin Formulations Containing a Thickening Agent

| # | pH | Osmolality (mOsm/kg H2O) | Appearance | Density (g/cc) | Viscosity (mPa-s) | Refractive Index (nD) | UV Absorbance | Insulin (% LC) Content | Insulin (% LC) Impurities | Preservative (% LC) MP | Preservative (% LC) PP |
|---|---|---|---|---|---|---|---|---|---|---|---|
| 1 | 7.5 | 160 | CC | 1.001 | 0.895 | 1.334 | 0.00 | 0.0 | 0.0 | 0.0 | 0.0 |
| 2 | 7.1 | 154 | CC | 1.001 | 0.927 | 1.335 | 0.00 | 0.0 | 0.0 | 158.2 | 119.2 |
| 3 | 7.4 | 154 | CC | 1.001 | 0.951 | 1.336 | 0.00 | 0.0 | 0.0 | 162.1 | 120.7 |
| 4 | 7.3 | 202 | CC | 1.013 | 0.966 | 1.340 | 0.00 | 0.0 | 0.0 | 107.8 | 117.8 |
| 5 | 7.2 | 171 | CC | 0.999 | 1.045 | 1.335 | 0.00 | 0.0 | 0.0 | 109.1 | 117.4 |
| 6 | 7.2 | 183 | CC | 1.002 | 0.936 | 1.337 | 0.00 | 105.0 | 0.9 | 110.4 | 110.3 |
| 7 | 7.2 | 189 | CC | 1.004 | 0.974 | 1.338 | 0.00 | 102.2 | 0.9 | 108.2 | 122.2 |
| 8 | 7.5 | 150 | CC | 1.001 | 1.013 | 1.334 | 0.00 | 0.0 | 0.0 | 0.0 | 0.0 |
| 9 | 7.4 | 184 | CC | 1.000 | 1.148 | 1.335 | 0.00 | 0.0 | 0.0 | 109.9 | 121.7 |
| 10 | 7.5 | 195 | CC | 1.001 | 1.273 | 1.336 | 0.00 | 0.0 | 0.0 | 111.6 | 122.7 |
| 11 | 7.3 | 232 | CC | 1.012 | 1.349 | 1.341 | 0.00 | 0.0 | 0.0 | 111.7 | 123.4 |
| 12 | 7.3 | 248 | CC | 1.016 | 1.465 | 1.344 | 0.00 | 107.7 | 1.4 | 113.8 | 120.6 |
| 13 | 7.3 | 256 | CC | 1.018 | 1.757 | 1.346 | 0.00 | 107.5 | 1.4 | 112.4 | 134.9 |
| 14 | 7.2 | 237 | ST | 1.004 | 1.810 | 1.335 | 0.00 | 0.0 | 0.0 | 0.0 | 0.0 |
| 15 | 7.2 | 197 | ST | 1.001 | 1.946 | 1.335 | 0.09 | 0.0 | 0.0 | 110.6 | 122.1 |
| 16 | 7.2 | 192 | CC | 1.003 | 9.839 | 1.337 | 0.07 | 0.0 | 0.0 | 111.4 | 152.4 |
| 17 | 7.5 | 232 | CC | 1.013 | 12.103 | 1.341 | 0.01 | 0.0 | 0.0 | 106.2 | 148.5 |
| 18 | 7.2 | 325 | CC | 1.017 | 21.668 | 1.344 | 0.02 | 99.7 | 2.8 | 106.2 | 154.9 |
| 19 | 7.2 | 257 | ST | 1.019 | 4.957 | 1.347 | 0.01 | 106.6 | 2.3 | 113.2 | 160.8 |
| 20 | 7.2 | 228 | CC | 1.012 | 7.693 | 1.342 | 0.11 | 0.0 | 0.0 | 110.4 | 157.4 |
| 21 | 7.5 | 237 | CC | 1.015 | 1.255 | 1.344 | 0.00 | 106.6 | 1.7 | 113.4 | 165.0 |
| 22 | 7.4 | 245 | CC | 1.017 | 1.304 | 1.346 | 0.00 | 106.3 | 1.4 | 111.5 | 174.1 |

CC = a clear and colorless solution was observed; ST = a slightly turbid solution was observed; LC = formulation label claim All formulations manufactured were clear and colorless in appearance except formulations 14, 15 and 19, which contained a thickening agent and were slightly turbid. These formulations contained Carbopol 974P, which is a very large molecule (molecular weight ~150,000) and is therefore may be difficult to solubilize without surfactants (e.g., Tween 80).

All initial and final pH measurements were within the range of 7.3±0.3, with the exception of formulations 1 and 2 which did not contain a thickening agent. The target pH for these two samples, were pH 2.0 and pH 3.0 respectively.

Osmolality measurements were generally within the range from about 200 to about 280 mOsm/kg $H_2O$ (i.e., within the range set forth in the insulin nasal spray final product specification), with the exception of formulations 1, 2 and 3 which did not contain a thickening agent and formulations 1, 2, 3, 5, 8 and 18 which did contain a thickening agent. The osmolality of these formulations was outside the expected range because they did not contain propylene glycol (i.e., the component within the insulin nasal spray formulation that has the largest effect upon tonicity) nor did they contain adequate sodium chloride to compensate for the absence of propylene glycol. the thickening agent modified formulation 18 was measured to have higher than expected osmolality at 325 mOsm/kg H2O. This observation may be attributed to the relative high amounts of sodium hydroxide and hydrochloric acid required to adjust pH and clarify the solution.

A summary of the chemical analyses performed on formulations containing a thickening agent are outlined in Table 39 above. HPLC was conducted on the formulations containing a thickening agent per the finished product specification insulin nasal spray to determine insulin identity, insulin assay, A-21 desamido insulin content, total other insulin related impurities, preservative identification (if appropriate), and preservative quantitation (if appropriate). HPLC analysis was not conducted on formulations that did not contain a thickening agent.

Insulin identification passed the required specification for insulin nasal spray for all formulations containing a thickening agent and insulin.

Insulin assay was measured to be within the 80.0-120.0% of label claim set forth in the finished product specification for all formulations containing a thickening agent and insulin.

The A-21 desamido content as a percent of insulin related peaks were ≤1% for all samples tested, well within the less than or equal to 10% specification. The total other insulin-related impurities were measured to be less than 5%, which is within the specification, for all samples tested.

All formulations that contained methylparaben and propylparaben (i.e., the formulation preservatives) passed the requirements for preservative identification set forth in the finished product specification for insulin nasal spray.

The HPLC analysis for preservative recovery of the formulations containing methylparaben and propylparaben demonstrated a higher level of preservatives for most samples evaluated in formulations containing a thickening agent. The preservative levels trended a bit high within the samples due to how parabens perform within the formulations. Previous studies have consistently yielded relative low (i.e., approximately 80% of label claim) recoveries of methylparaben and propylparaben even though the correct amounts of each component are added to the formulations during the manufacturing process. To compensate for this loss, the formulations containing a thickening agent were manufactured assuming this 20% loss (i.e., the formulations manufactured assuming 0.40 mg/mL methylparaben and 0.2 mg/mL propylparaben in hopes of obtaining final concentrations of 0.33 mg/mL and 0.17 mg/mL of methylparaben and propylparaben respectively).

In addition, as determined herein, the "in use stability" of thickening agent modified formulations and those formulations manufactured without a thickening agent (e.g., with CMC or Carbopol) was evaluated. All such formulations tested were shown to be stable upon spraying, including when evaluated for insulin content, impurities and shot weight. Similarly, formulations containing a thickening agent were shown to be stable after storage for eighty days at 25° C. and 60% relative humidity; and, under accelerated stability conditions of 40° C. and 75% relative humidity. In addition, at 5° C. and ambient humidity (referred to as "as sold" stability), all formulations containing a thickening agent were shown to be stable.

Example 6

Stable Nasal Spray Formulations of Regular Human Insulin in Monomeric/Dimeric Form Particle size characterization studies were conducted to determine the physical (e.g., oligomeric) state of insulin within the insulin nasal spray formulations. Such determinations may be evaluated by determining the particle size distribution of formulations containing insulin in combination with one or more of the various pharmaceutically acceptably excipients disclosed herein (e.g., methyl-β-cyclodextrin, Polysorbate 80, edetate disodium, propylene glycol, arginine, methylparaben, propylparaben, carboxymethylcellulose sodium (CMC), and carbomer (e.g., carbopol 974P) using a subtraction style experimental design. For clarity, as used herein, carbopol is a carbomer; carbopol 974P is also known as Carbomer Homopolymer Type B, or Carbopol® 974P NF Polymer.

Clinically, two relevant dosage strengths of insulin nasal spray, 250 and 500 IU/mL, were evaluated (IU=international units). There are approximately 28 IU per milligram of insulin). The insulin nasal spray formulations without or with a thickening agent (e.g., CMC and Carbopol) that were evaluated in this Example are presented above Table 34 and Table 35. In addition, two different marketed injectable insulin products were also evaluated as comparators. Humulin® R is an injectable product which contains zinc, which has been shown to stabilize regular human insulin in the hexameric form. Humulin is known as an "intermediate acting" injectable insulin. The other marketed injectable product tested, NovoLog (insulin aspart), contains a chemically modified form of insulin designed to favor the monomeric state, and thus providing a rapid acting injectable insulin. The IN formulations including a thickening agent that were tested are shown in Table 40.

TABLE 40

Insulin Nasal Spray Formulations Containing a Thickening Agent

| Component | Carbopol Formulation Concentrations | | CMC Formulation Concentrations | |
|---|---|---|---|---|
| | mg/mL or IU/mL | mM | mg/mL or IU/mL | mM |
| Human Insulin, Recombinant | 250 and 500 IU/mL | — | 250 and 500 IU/mL | — |
| Methyl-β-Cyclodextrin (Me-β-CD) | 45 mg/mL | 33.3 | 45 mg/mL | 33.3 |
| Edetate Disodium Dihydrate (EDTA) | 1 mg/mL | 2.7 | 1 mg/mL | 2.7 |
| L-Arginine Hydrochloride | 2.1 mg/mL | 10 | 2.1 mg/mL | 10 |
| Polysorbate 80 | 10 mg/mL | 7.6 | 10 mg/mL | 7.6 |
| Carboxymethylcellulose Sodium (CMC) | 0 mg/mL | 0 | 1 mg/mL | <0.0† |
| Carbopol 974P (Carbomer) | 2.5 mg/mL | <0.0† | 0 mg/mL | 0 |
| Propylene Glycol | 10 mg/mL | 25 | 10 mg/mL | 25 |
| Methylparaben | 0.33 mg/mL | 2.2 | 0.33 mg/mL | 2.2 |
| Propylparaben | 0.17 mg/mL | 0.9 | 0.17 mg/mL | 0.9 |

†Molecular weights in excess of 100,000 Da

The Malvern Zetasizer Nano ZS was used to measure particle size. The instrument uses a Helium-Neon laser and non-invasive back-scatter technology to determine the hydrodynamic radii of particles. The size of a particle is indirectly proportional to its Brownian motion (through its diffusion co-efficient) and this relation is given by the Stokes-Einstein equation: $d(H) = kT/3\pi\eta D$ where: $d(H)$=hydrodynamic diameter; $D$=translational diffusion coefficient; $k$=Boltzmann's constant; $T$=absolute temperature; and $\eta$=viscosity.

The amount of back-scatter of the particles in Brownian motion is detected by the instrument and is then auto-correlated to give the hydrodynamic radius.

Disposable polystyrene cuvettes (12 mm², low-volume from Malvern Instruments USA, catalog #ZEN0112) are used to read the samples within the instrument. Each cuvette was first air-blown to remove any dust or lint particles. 500 μl of the sample was first loaded into a sterile-packed 1 cc syringe (BD Corp., catalog #309628) and then filtered into the cleaned cuvette through a low protein-binding, 13 mm diameter, 0.22 μm pore size PVDF syringe filter (Millipore Corporation, catalog #SLGV013 SL).

Control cuvettes were loaded with 1.0 mL of sterile filtered water (0.02 μm filtered). The standards used to calibrate the instrument were: lysozyme (~3.8 nm diameter), Bovine Serum Albumin (~7.2 nm diameter) 20, 30 and 40 nm diameter polystyrene Duke Standards. All standards were appropriately diluted in filtered water before testing as highly concentrated samples lead to a large amount of light scattering and an overloaded detector. Each test cuvette was loaded with the appropriate insulin sample and only those samples that were observed to be visually clear and colorless in appearance are assayed.

The instrument chamber was first equilibrated for at least 30 minutes prior to conducting the first measurement in order to stabilize the temperature of the sample/cell chamber. The pre-loaded cuvette was then capped and placed in the cell chamber to conduct the measurements. Approximately three minutes were provided for each sample to equilibrate to 25° C. within the sample chamber before each reading. Three measurements of ten readings each are taken per cuvette. Each sample involved two separate cuvettes to ensure reproducibility of the data.

Standards of known particle size were tested to confirm validity of the assay. The particle size measurements of the standards were close to their theoretical values obtained from literature. Table 41 shows the comparison of the known (theoretical) values and observed (determined) particle size values of the standards.

TABLE 41

Comparison of Theoretical and Determined Particle Sizes of Standards

| Standard | Theoretical Size (nm) | Determined Size (nm) | |
|---|---|---|---|
| | | Study 1 | Study 2 |
| Lysozyme | 3.8[a] | 3.83 ± 0.7 | Not measured |
| BSA | 7.2[a] | 6.31 ± 1.0 | 6.3 ± 1.0 |
| Duke 20 nm | 21.0 ± 1.5[b] | 19.2 ± 3.0 | 19.5 ± 3.1 |
| Duke 30 nm | 33.0 ± 1.4[b] | 33.0 ± 4.4 | 32.2 ± 4.4 |
| Duke 40 nm | 40.0 ± 1.8[b] | 42.3 ± 5.4 | 41.0 ± 5.1 |

[a]from Malvern technical notes: www.malvern.co.uk/LabEng/industry/protein/protein_solutions.htm
[b]Duke standards' specifications sheet The control samples of insulin in saline at various pH levels provided results in agreement with previously published data. As depicted in Table 42 the marketed products tested, insulin in both the strengths of Humulin® R appear to be in the monomer/dimer form, whereas NovoLog appears to be stabilized in the hexameric state. In addition, the formation of insulin complexes (i.e., dimer or hexamer) is known to be dependent upon solution pH. At pH 2.0, the insulin is thought to be stabilized predominantly in the monomeric form; at pH 3.0, the dimeric form is thought to be dominant; and at pH 7.0 the molecules are thought to be stabilized in the hexameric state. These values are based upon the theoretical monomer, dimer and hexamer sizes obtained from literature. Table 42 compares the observed and theoretical particle sizes of the controls.

TABLE 42

Comparison of Theoretical and Determined Particle Sizes of Insulin Controls

| Formulation | Theoretical Size (nm) | Determined Size (nm) | Perceived Insulin Oligomeric State |
|---|---|---|---|
| No Thickening agent 1 (pH 2) | 2.7 | 2.6 ± 0.5 | Monomer |

TABLE 42-continued

Comparison of Theoretical and Determined
Particle Sizes of Insulin Controls

| Formulation | Theoretical Size (nm) | Determined Size (nm) | Perceived Insulin Oligomeric State |
|---|---|---|---|
| Humulin 100 U/ml | N/A | 2.8 ± 0.5 | Monomer |
| Humulin 500 U/ml | N/A | 2.9 ± 0.5 | Monomer |
| No Thickening Agent 2 (pH 3) | 3.4 | 2.7 ± 0.5 | Dimer |
| No Thickening Agent 3 (pH 7) | 5.2 | 4.3 ± 0.7 | Hexamer |
| NovoLog 100 U/ml | N/A | 4.4 ± 0.7 | Hexamer |

N/A = not available

Particle sizes consistent with those of insulin monomer, dimer and hexamer sizes presented in the literature were experimentally confirmed via the dynamic light scattering evaluation of samples that contain insulin, saline, and buffers appropriate for the various pH levels tested (i.e., pH 2, 3, and 7).

The control formulations, Humulin R and NovoLog, performed as expected via dynamic light scattering. Both the 100 IU/mL and the 500 IU/mL concentration formulations of Humulin were found to contain a single species, likely to be insulin, in the presumed monomeric state (2.8 nm-2.9 nm). The 100 IU/mL NovoLog, insulin was found to probably exist in hexamer state.

In the study of formulations that did not contain a thickening agent from Table 34, the low insulin concentration nasal spray formulation (sample 9) was determined to contain particles, the majority of which (99% by volume) were found to be 3.1±0.7 nm in size, whereas a second population of particles (i.e., the remaining 1% by volume) were measured to be 33.2±7.8 nm. When the same formulation was evaluated in the study of formulations that did contain a thickening agent from Table 35; formulation 21 containing a thickening agent, the particle size distribution was determined to contain a third population (i.e., 41% by volume) of particle size 1.4±0.2 nm. The other particle sizes detected were mostly 3.5±0.6 nm (i.e., 58% by volume) and a small population (i.e., 1% by volume) of size 29.3±12.6 nm.

In case of the high insulin concentration formulation (sample 10 without thickening agent from Table 34 and sample 22 with a thickening agent from Table 35), the particle size distribution was virtually identical in the two studies. Approximately one third of the particles detected by volume were roughly 1.5±0.2 nm in size while the remaining approximate two thirds were determined to be roughly 3.5±0.6 nm in size. As observed in the lower concentration formulation (sample 9 manufactured without a thickening agent and sample 21 manufactured with a thickening agent), approximately 1% by volume was determined to be 33.5±0.5 nm in size.

The average particle size distributions of the two strengths were virtually identical. Three separate species appeared to exist in each of the strengths, approximately one third of the particles by volume were of roughly 1.5 nm diameter while the remaining approximate two-thirds by volume were of roughly 3.5 nm diameter. Finally, a third population of roughly 33 nm diameter was observed, but comprised approximately 1% of the population by volume.

Tables 43 and 44 provide a summary of the particle size distributions of the samples (formulations manufactured without a thickening agent from Table 34 and formulations manufactured with a thickening agent from Table 35, respectively) tested in the two studies.

TABLE 43

Summary of Particle Size Distribution of Insulin Formulations
Manufactured Without a Thickening Agent

| | Determined Size in nm (% Volume) | | |
|---|---|---|---|
| Formulation | Peak 1 | Peak 2 | Peak 3 |
| 4 | 2.2 ± 0.6 | N/A | N/A |
| 5 | 1.0 ± 0.1 (9%) | 3.2 ± 0.7 (91%) | N/A |
| 6 | 5.2 ± 1.0 | N/A | N/A |
| 7 | 5.2 ± 0.9 | N/A | N/A |
| 8 | 8.9 ± 1.6 (27%) | 32.0 ± 8.1 (73%) | N/A |
| 9 | 3.1 ± 0.7 (99%) | 33.2 ± 7.8 (1%) | N/A |
| 10 | 1.5 ± 0.2 (31%) | 3.5 ± 0.6 (68%) | 33.5 ± 0.5 (1%) |

N/A = not applicable (no reading)

TABLE 44

Summary of Particle Size Distribution of Insulin
Formulations Manufactured With a Thickening Agent

| | Determined Size in nm (% Volume) | | |
|---|---|---|---|
| Formulation | Peak 1 | Peak 2 | Peak 3 |
| 1 | 0.8 ± 0.1 | N/A | N/A |
| 2 | 0.8 ± 0.1 | N/A | N/A |
| 3 | 8.0 ± 1.1 | N/A | N/A |
| 4 | 1.2 ± 0.2 | N/A | N/A |
| 5 | 0.7 ± 0.1 | N/A | N/A |
| 6 | 5.1 ± 0.9 | N/A | N/A |
| 7 | 5.0 ± 0.9 | N/A | N/A |
| 8 | 8.8 ± 2.5 | N/A | N/A |
| 9 | 1.9 ± 0.2 (15%) | 6.8 ± 0.9 (85%) | N/A |
| 10 | 6.1 ± 0.9 | N/A | N/A |
| 11 | 1.0 ± 0.2 | N/A | N/A |
| 12 | 2.2 ± 0.5 (99%) | 24.5 ± 6.3 (1%) | N/A |
| 13 | 0.9 ± 0.1 (17%) | 2.5 ± 0.4 (82%) | 19.6 ± 5.7 (1%) |
| 14 | N/A | N/A | N/A |
| 15 | 2.3 ± 0.2 (50%) | 5590.0 ± 323.0 (50%) | N/A |
| 16 | 0.8 ± 0.1 | N/A | N/A |
| 17 | 3080.0 ± 483.5 | N/A | N/A |
| 18 | 1.3 ± 0.2 (98%) | 6.8 ± 2.4 (1%) | N/A |
| 19 | 0.6 ± 0.0 (99%) | 6.5 ± 0.5 (1%) | N/A |
| 20 | 30.4 ± 6.5 (100%) | N/A | N/A |

TABLE 44-continued

Summary of Particle Size Distribution of Insulin
Formulations Manufactured With a Thickening Agent

| | Determined Size in nm (% Volume) | | |
|---|---|---|---|
| Formulation | Peak 1 | Peak 2 | Peak 3 |
| 21 | 1.4 ± 0.2 (41%) | 3.5 ± 0.6 (58%) | 29.3 ± 12.6 (1%) |
| 22 | 1.5 ± 0.2 (33%) | 3.6 ± 0.7 (66%) | 35.7 ± 12.2 (1%) |

N/A = not applicable (no reading)

When the particle size of the formulations without Tween 80 (i.e., sample 4 without a thickening agent from Table 43, cross-referencing Table 34) were evaluated, the low insulin concentration was found to be comprised of a single population of particles sized 2.2±0.6 nm diameter. In contrast, the particle size distribution of the high insulin concentration formulation is found to contain bimodal particle size distribution. The majority (91% by volume) of the particles were of diameter 3.2±0.7 nm while the remaining (9% were by volume) are of diameter 1.0±0.1 nm, and may represent a concentration-dependent effect upon particle formulation in the absence of Tween 80.

In the absence of methyl-β-cyclodextrin (i.e., samples 6 and 7 manufactured without a thickening agent from Table 34) both low and high insulin concentrations yielded a single peak of the same size; 5.2±1.0 nm and 5.2±0.9 nm, respectively.

Formulations that contain insulin but no Tween 80 or methyl-β-cyclodextrin were evaluated. A size distribution similar to that observed in the formulations without methyl-β-cyclodextrin was observed (i.e., 5.0±0.9 nm). This result is consistent with the approximate size of insulin hexamers (i.e., sample 3 manufactured without a thickening agent), which is the likely complexation state of insulin expected to be prevalent in pH 7.3 in arginine buffer. These data may indicate that there is a difference between those formulations that contain insulin, methyl-β-cyclodextrin and Tween 80, but that the formulations that contain insulin and Tween 80 or insulin alone are equivalent. Therefore, it appears that there may be an unexpected molecular interaction between the three components (i.e., Tween 80, methyl-β-cyclodextrin, and insulin) that allows for the formation of particles of a size consistent with insulin monomer/dimer to be formed.

A placebo formulation (sample 20 manufactured with a thickening agent as identified in Table 35) was evaluated and was found to contain a single species of particle size 30.4±6.5 nm. A formulation of identical composition was evaluated, sample 8 without a thickening agent (see Table 34), and was observed to contain two populations of particle sizes 8.9±1.6 nm (27% by volume) and 32.0±8.1 nm (73% by volume). The difference in the results obtained for a formulation of identical composition may be explained by the presence of a potential outlier peak that was observed in a single measurement in the study presented in Table 43 (without a thickening agent) and was included in the average particle size calculation. When this outlier is removed from the average calculation, a monomodal particle size distribution is observed with average particle size 31.5±7.1 nm, which is very similar to the average obtained for the equivalent formulation evaluated in the study presented in Table 35, which includes the addition of a thickening agent.

A placebo formulation that contained methyl-β-cyclodextrin but no Tween 80 showed a single peak at 1.1±0.3 nm, which corresponded with the expected size of methyl-β-cyclodextrin inclusion complexes. Placebo that contained Tween 80 but no methyl-β-cyclodextrin was also found to be comprised of a single species, but of a larger size, 8.1±1.0. This particle size distribution is likely attributed to the formation of Tween 80 micelles. The formulation concentration of 10 mg/mL (i.e., 7.6 mM) is several times higher than the critical micelle concentration of 0.1 mM.

Formulations that contained propylene glycol were compared to those that did not. The particle size distributions remain unchanged in the presence or absence of propylene glycol, indicating that propylene glycol did not have an effect of the formation of methyl-β-cyclodextrin complexes or Tween 80 micelles (or the interaction between methyl-β-cyclodextrin, Tween 80, and insulin interactions) within the formulation.

Formulations containing carboxymethylcellulose sodium, low viscosity (CMC LV) were evaluated in the study presented in Table 35 (thickening agent modified formulations). The formulation containing 1 mg/mL CMC LV in arginine buffer at pH 7.3 was found to contain a single species of particle size 8.8±2.5 nm. When the preservatives and propylene glycol were added to this formulation, the distribution was observed to be bimodal with peaks at particle size 1.9±0.2 nm (15% by volume) and 6.8±0.9 nm (85% by volume). Further, when Tween 80 was included in the formulation (thickening agent containing sample 10, Table 35), a monomodal distribution of particles was regained with average particle diameter 6.1±0.9 nm. However, the presence of methyl-β-cyclodextrin (in the absence of Tween 80) resulted in a single species but of smaller particle diameter; 1.0±0.2 nm. Low and high concentration insulin nasal spray formulations (samples 12 and 13, containing a thickening agent, Table 35) consisted mostly of particles of average size 2.2±0.5 nm (99% by volume) and 2.5±0.4 nm (82% by volume) respectively. The high insulin concentration formulation (sample 13, containing a thickening agent, Table 35) had an additional peak of particle size 0.9±0.1 nm (17% by volume), as a result of an outlier during one measurement.

The sample 17 (see Table 35) containing carbopol 974P as thickening agent and methyl-β-cyclodextrin was comprised of a population of particles greater than 3 μm and other populations that are of size greater than the measuring range of the instrument (i.e., over 10 μm). A single population of particles of size 0.8±0.1 nm diameter was observed in a formulation containing Tween 80 and Carbopol 974P in arginine buffer. This observation is different from the size of Tween 80 micelles observed in the absence of Carbopol 974P (average particle size 8.1±1.0 nm). Low and high concentration insulin nasal spray formulations containing Carbopol 974P had particle sizes 1.3±0.2 nm (98% by volume) and 0.6±0.0 nm (99% by volume) in size, respectively.

In summary, the identified insulin nasal spray formulations, including formulations containing a thickening agent such as CMC or Carbopol 974P, contain particles that are consistent in size with insulin monomers and/or dimers.

According to the data presented herein, there was no difference in particle size distribution when the formulations were either filtered through a 0.22 um polystyrene syringe filter, centrifuged at 100 rpm for 5 minutes, or were unfiltered or not centrifuged.

Tween 80 is known to form micelles at concentrations of at least 5 µM, (note that the Insulin Nasal Spray formulation contains 7 mM Tween 80) and these micelles were observed to be the approximate size of 8 nm. Methyl-β-cyclodextrin is also known to forms complexes that are approximately 1 nm in size within the Insulin Nasal Spray formulation; these approximate 1 nm particles were observed as expected. The presence or absence of propylene glycol does not seem to affect either the Tween 80 micelle formation or the methyl-β-cyclodextrin complex formation.

Insulin at high and low concentrations in arginine buffer (i.e., in the absence of Tween 80 and methyl-β-cyclodextrin) at pH 7.3 was observed to contain particles that are consistent with insulin molecules in the hexameric state (i.e., ~5.2 nm). The addition of Tween 80 to the system does not alter the size of the particles (i.e., the ~5.2 nm particle population is observed, with a second population at ~8 nm, representing the probable population of Tween 80 micelles). The addition of methyl-β-cyclodextrin results in a single peak at approximately 2.2 nm for the low concentration insulin nasal spray formulation (i.e., a particle consistent with the size of an insulin monomer or dimer). A bimodal distribution (i.e., 3.2 nm (91% by volume) and 1.0 nm (9% by volume)) was observed for the high concentration insulin nasal spray formulation. These findings may indicate a concentration dependence for insulin monomer/dimer stabilization; i.e., that the formulation excipients may need to be properly ratioed to account for insulin concentration. The data disclosed may indicate that methyl-β-cyclodextrin and Tween 80 act synergistically to stabilize insulin in the monomeric or dimeric (i.e., rather than hexameric) form. The data indicate that particles consistent in size to the theoretical size of insulin monomer/dimer are formed within certain of the insulin nasal formulations disclosed herein independent of insulin concentration.

Insulin was present in the monomeric/dimeric form within the insulin nasal spray formulation containing CMC and there was a similar size distribution for both low and high concentration formulations. The data also indicate that insulin is present in the monomeric/dimeric form within insulin nasal spray formulations containing Carbopol 974P for both in the low and high concentration formulations.

The dynamic light scattering data show the surprising result that regular human insulin molecules were stabilized in the monomeric or dimeric form within the nasal spray formulations, including formulations containing a thickening agent such as CMC or Carbopol 974P. These results in combination with the biological data in rabbits and humans show ultra-rapid acting insulin is achieved with the described nasal spray formulations.

Example 7

Preservative Optimization of Formulations Comprising a Thickening Agent and Insulin This example summarizes studies performed in order to develop a preservative system for Insulin Nasal Spray formulations suitable for USP Antimicrobial Effectiveness Testing requirements and EP Antimicrobial Effectiveness Testing requirements. A variety of pharmaceutically acceptable preservatives were screened that are known to be used in currently marketed nasal spray products, and all levels selected for this study are within the range of concentrations in those currently marketed products for each preservative. A list of exemplary preservatives evaluated is shown in Table 45.

TABLE 45

| Preservatives used in Insulin Nasal Spray Formulations | |
|---|---|
| Preservative | Levels Evaluated |
| Benzethonium Chloride | 0.1-0.2 mg/mL |
| Methylparaben* | 0.33-4.2 mg/mL |
| Propylparaben* | 0.17-2 mg/mL |
| Phenylethyl Alcohol | 1-2 mg/mL |
| Benzyl Alcohol | 1-5 mg/mL |
| Ethanol | 2 mg/mL |

*Note that both the sodium salts and free base phenols have been evaluated

The antimicrobial effectiveness of a formulation is determined using the USP and EP Antimicrobial Effectiveness Testing (AET) methodologies, which are described in USP <51> and EP <5.4.1>. The requirements for each test are represented in Tables 46 and 47.

TABLE 46

USP AET Requirements, USP <51>
USP AET Requirements, USP <5l>

| | Microorganism | | | | | | | | | |
|---|---|---|---|---|---|---|---|---|---|---|
| | P. aeurginosa | | E. coli | | S. aureus | | C. albicans | | A. niger | |
| Days | 14 | 28 | 14 | 28 | 14 | 28 | 14 | 28 | 14 | 28 |
| Log Reduction (Min) | 2 | no increase | 2 | no increase | 2 | no increase | no increase | no increase | no increase | no increase |

TABLE 47

EP AET Requirements, EP <5.4.1>
EP AET Requirements, EP <5.4.1>

| | Microorganism | | | | | | | | |
|---|---|---|---|---|---|---|---|---|---|
| | P. aeurginosa | | | S. aureus | | | C. albicans | | A. niger | |
| Days | 2 | 7 | 28 | 2 | 7 | 28 | 14 | 28 | 14 | 28 |
| Log Reduction (Min) | 2 | 3 | no increase | 2 | 3 | no increase | 2 | no increase | 2 | no increase |

The quality (physical and chemical analysis) of all formulations to be evaluated was monitored for pH, osmolality, and appearance at the time of manufacturing. In addition, HPLC analysis was performed at T=0 and T=end of study to ensure stability of insulin and of the preservative, as necessary. The data were used to identify a combination of preservatives that are successful in passing USP AET requirements for both the carbomer (e.g., Carbopol 974P) and CMC Insulin Nasal Spray formulations. Table 48 illustrates the tested combinations.

TABLE 48

Effective Preservative Combination Formulations (i.e., Passes USP AET Requirements)

| ID # | Insulin Conc. (IU/mL) | Me-β-CD (mg/mL) | EDTA (mg/mL) | Polysorbate 80 (mg/mL) | Arginine (mg/mL) | Propylene Glycol (mg/mL) | CMC (mg/mL) | CH (mg/mL) | MP/PP | PE (mg/L) | pH |
|---|---|---|---|---|---|---|---|---|---|---|---|
| 1 | 250 | 45 | 1 | 10 | 2.1 | 10 | 0 | 2.5 | 3.3/1.7 | 2 | 7.3 ± 0.3 |
| 2 | 500 | 45 | 1 | 10 | 2.1 | 10 | 0 | 2.5 | 3.3/1.7 | 2 | 7.3 ± 0.3 |
| 3 | 250 | 45 | 1 | 10 | 2.1 | 10 | 1 | 0 | 3.3/1.7 | 2 | 7.3 ± 0.3 |
| 4 | 1000 | 45 | 1 | 10 | 2.1 | 10 | 1 | 0 | 3.3/1.7 | 2 | 7.3 ± 0.3 |

Abbreviations: Me-β-CD: methyl-β-cyclodextrin, EDTA = edetate disodium, Polysorbate 80 = Tween 80, CMC = carboxymethylcellulose sodium, CH = carbomer homopolymer (trade name: Carbopol 974P), MP = methylparaben, PP = propylparaben, PE = phenylethanol The formulations presented in Table 48 underwent release testing that included appearance, pH, osmolality, and quantification of insulin content, methylparaben content, propylparaben content, A-21 desamido insulin content, total other insulin related substances by Reverse Phase HPLC. The formulations underwent post-testing at the end of the assay (i.e., one month post-manufacturing, formulations stored at 2-8° C.) to ensure stability and product quality. The release data are listed in Table 49, and the end of study data are listed in Table 50. The data illustrate that the formulations evaluated are stable over the 1 month duration required for Antimicrobial Effectiveness Testing per the US and European compendia.

TABLE 49

Release Testing of Formulations Passing USP AET Requirements

| Formulation Number | Appearance | pH | Osmolality | Insulin Assay | A-21 desamido insulin content | Total other insulin related substances content | Methyl-paraben content | Propyl-paraben content |
|---|---|---|---|---|---|---|---|---|
| 1 | Slightly turbid solution | 7.3 | 250 | 101.4 | 1.0 | 1.8 | 100.4 | 101.5 |
| 2 | Slightly turbid solution | 7.3 | 258 | 100.9 | 0.6 | 1.3 | 97.6 | 101.1 |
| 3 | Clear and colorless solution | 7.3 | 242 | 102.9 | 0.7 | 1.2 | 97.5 | 100.9 |
| 4 | Clear and colorless solution | 7.3 | 281 | 103.2 | 0.8 | 0.9 | 97.1 | 101.8 |

TABLE 50

Post Testing of Formulations Passing USP AET Requirements

| Formulation Number | Appearance | pH | Osmolality | Insulin Assay | A-21 desamido insulin content | Total other insulin related substances content | Methyl-paraben content | Propyl-paraben content |
|---|---|---|---|---|---|---|---|---|
| 1 | Slightly turbid solution | 7.3 | 245 | 96.4 | 0.6 | 3.2 | 96.1 | 99.6 |
| 2 | Slightly turbid solution | 7.4 | 258 | 99.7 | 0.7 | 2.2 | 95.3 | 102.8 |
| 3 | Clear and colorless solution | 7.4 | 239 | 101.1 | 0.9 | 0.9 | 97.1 | 101.9 |

TABLE 50-continued

Post Testing of Formulations Passing USP AET Requirements

| Formulation Number | Appearance | pH | Osmolality | Insulin Assay | A-21 desamido insulin content | Total other insulin related substances content | Methyl-paraben content | Propyl-paraben content |
|---|---|---|---|---|---|---|---|---|
| 4 | Clear and colorless solution | 7.4 | 269 | 103.3 | 1.0 | 0.8 | 101.1 | 108.1 |

The USP AET results for the formulations presented in Tables 48 are listed in Table 51. The corresponding EP AET results are listed in Table 52.

TABLE 51

Representative USP AET Data (Log Reduction) for Specific Formulations

| | Microorganism | | | | | | | | |
|---|---|---|---|---|---|---|---|---|---|
| | P. aeurginosa | | E. coli | | S. aureus | | C. albicans | | A. niger |
| Days | 14 | 28 | 14 | 28 | 14 | 28 | 14 | 28 | 14 | 28 |
| Formulation 1 | 5.8 | 5.8 | 5.9 | 5.9 | 5.9 | 5.9 | 1.2 | 2.1 | 1.2 | 2.1 |
| Formulation 2 | 5.8 | 5.8 | 5.9 | 5.9 | 5.9 | 5.9 | 1.2 | 2.1 | 1.2 | 2.1 |
| Formulation 3 | 5.5 | 5.5 | 5.8 | 5.8 | 5.7 | 5.7 | 1.1 | 1.9 | 1.8 | 3.3 |
| Formulation 4 | 5.5 | 5.5 | 5.8 | 5.8 | 5.7 | 5.7 | 0.9 | 2.1 | 1.7 | 2.0 |

TABLE 52

Representative EP AET Data (Log Reduction) for Specific Formulations

| | Microorganism | | | | | | | |
|---|---|---|---|---|---|---|---|---|
| | P. aeurginosa | | | S. aureus | | | C. albicans | | A. niger |
| Days | 2 | 7 | 28 | 2 | 7 | 28 | 14 | 28 | 14 | 28 |
| Formulation 1 | 5.8 | 5.8 | 5.8 | 0.2* | 3.1 | 5.9 | 1.2** | 2.1 | 1.2* | 2.1 |
| Formulation 2 | 5.8 | 5.8 | 5.8 | 0.3* | 3.4 | 5.9 | 1.2** | 2.1 | 1.2** | 2.1 |
| Formulation 3 | 5.5 | 5.5 | 5.5 | 0.3* | 3.3 | 5.7 | 1.1** | 1.9 | 1.8** | 3.3 |
| Formulation 4 | 5.5 | 5.5 | 5.5 | 0.6* | 3.5 | 5.7 | 0.9* | 2.1 | 1.7** | 2.0 |

*Indicates failing result
**Passes EP "Category B" Requirements (requires a 1-log reduction of C. albicans and A. niger at T = 14 days rather than the 2-log reduction required by the "Category A" requirements)

As presented in Tables 51 and 52, all four formulations tested pass USP AET requirements. In addition, all formulations are demonstrated to be stable over the course of this study, providing additional confidence in the final AET data.

In summary, a combination of preservatives were evaluated and shown to provide antimicrobial activity within Insulin Nasal Spray formulations sufficient to pass US compendia antimicrobial effectiveness testing requirements. In addition, these formulations were shown to be stable for a least one month based upon physical (i.e., appearance, pH, osmolality) and chemical (i.e., insulin assay, A-21 desamido insulin, total other insulin related substances, methylparaben assay, and propylparaben assay) stability measurements.

All U.S. patents, U.S. patent application publications, U.S. patent applications, foreign patents, foreign patent applications, non-patent publications, figures, tables, and websites referred to in this specification are expressly incorporated herein by reference, in their entirety.

Although the foregoing disclosure has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

What is claimed is:

1. A clinical pharmaceutical formulation comprising an aqueous mixture of an insulin molecule in monomeric or dimeric form, methyl-β-cyclodextrin, a surface active agent, and a thickening agent, wherein the pharmaceutical formulation has a clinically significant ultra-rapid acting insulin profile with Tmax less than 40 min in a patient and bioavailability of insulin in the patient of from 16% to 30%.

2. The pharmaceutical formulation of claim 1, wherein the ultra-rapid acting insulin profile has peak serum levels of the administered human insulin less than about 40 minutes post-administration and glucose troughs less than 60 minutes post-administration.

3. The pharmaceutical formulation of claim 1, wherein the insulin molecule is selected from group consisting of a human insulin; LysB3, GluB29-human insulin; LysB3, IleB28 human insulin; GlyA21, HisB31, HisB32-human insulin; AspB10-human insulin, LysB28, and ProB29-human insulin.

4. The pharmaceutical formulation of claim 1, wherein the surface-active agent is selected from the group consisting of nonionic polyoxyethylene ether, fusidic acid and derivatives thereof, sodium taurodihydrofusidate, L-α-phosphatidylcholine didecanoyl, polysorbate 80, polysorbate 20, polyethylene glycol, cetyl alcohol, polyvinylpyrolidone, polyvinyl alcohol, lanolin alcohol, sorbitan monooleate, and mixtures thereof.

5. The pharmaceutical formulation of claim 1, wherein the thickening agent is selected from a group consisting of gelatin, hydroxypropyl methylcellulose, methylcellulose, a carbomer, carboxymethylcellulose, and mixtures thereof.

6. The pharmaceutical formulation of claim 1, wherein the formulation has a pH of about 7.

7. A method for decreasing blood glucose or for treating conditions related to elevated blood glucose in a human comprising administering the pharmaceutical formulation of claim 1 to the human, wherein the condition related to elevated blood glucose is selected from the group consisting of Type 2 diabetes, Type 1 diabetes, impaired glucose tolerance, hyperglycemia, insulin resistance syndrome, and glucosuria.

8. The pharmaceutical formulation of claim 1, wherein the solubilizing agent is methyl-β-cyclodextrin, the surface active agent is polysorbate 80, and the thickening agent is carboxymethylcellulose.

* * * * *